United States Patent
Briskin et al.

(10) Patent No.: US 7,038,018 B2
(45) Date of Patent: May 2, 2006

(54) ANTIBODIES AND LIGANDS FOR "BONZO" CHEMOKINE RECEPTOR

(75) Inventors: Michael J. Briskin, Lexington, MA (US); Kristine E. Murphy, Wakefield, MA (US); Alyson M. Wilbanks, Cambridge, MA (US); Lijun Wu, Reading, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 322 days.

(21) Appl. No.: 09/940,063

(22) Filed: Aug. 27, 2001

(65) Prior Publication Data

US 2002/0090657 A1 Jul. 11, 2002

Related U.S. Application Data

(62) Division of application No. 09/449,437, filed on Nov. 24, 1999, now Pat. No. 6,319,675.

(51) Int. Cl.
| | |
|---|---|
| C07K 16/00 | (2006.01) |
| C07K 16/18 | (2006.01) |
| C07K 16/28 | (2006.01) |
| C12N 5/12 | (2006.01) |
| G01N 33/53 | (2006.01) |

(52) U.S. Cl. ............... 530/387.1; 530/387.3; 530/388.1; 530/388.22; 435/7.1; 435/325; 435/326; 435/329; 435/334; 435/810

(58) Field of Classification Search ............. 530/387.1, 530/387.2, 387.9, 388.1, 388.2, 388.22, 388.7; 435/325, 326, 329, 331, 332, 334, 343, 346, 435/810
See application file for complete search history.

(56) References Cited

U.S. PATENT DOCUMENTS

| | | | |
|---|---|---|---|
| 5,739,103 | A | 4/1998 | Rollins et al. |
| 5,767,260 | A | 6/1998 | Whitlow et al. |
| 5,824,504 | A | 10/1998 | Elshourbagy et al. |
| 5,824,782 | A | 10/1998 | Hölzer et al. |
| 5,889,157 | A | 3/1999 | Pastan et al. |
| 5,948,647 | A | 9/1999 | Ring |
| 5,985,276 | A | 11/1999 | Lindhofer et al. |
| 6,037,454 | A * | 3/2000 | Jardieu et al. |
| 6,232,084 | B1 | 5/2001 | MacPhee et al. |
| 6,251,582 | B1 | 6/2001 | Littman et al. |
| 2002/0076694 | A1 | 6/2002 | Littman et al. |
| 2003/0165995 | A1 | 9/2003 | Briskin et al. |

FOREIGN PATENT DOCUMENTS

| | | |
|---|---|---|
| EP | 0834563 A2 | 4/1998 |
| WO | WO 98/44098 | 10/1998 |
| WO | WO 99/03888 | 1/1999 |
| WO | WO 99/27078 | 6/1999 |
| WO | WO 99/50670 | 10/1999 |
| WO | WO 01/64752 A2 | 9/2001 |

OTHER PUBLICATIONS

Brussel et al. AIDS Res Hum Retroviruses. Sep. 20, 1999;15(14):1315-1319.*

Lu, P.H. and R.S. Negrin, "A Novel Population of Expanded $CD3^+CD56^+$ Cells Derived from T Cells with Potent *In Vivo* Antitumor Activity in Mice with Severe Combined Immunodeficiency," *J. Immunol.* 153(4): 1687-1696 (1994).

Liao, F. et al., "STRL33, a Novel Chemokine Receptor-like Protein, Functions as a Fusion Cofactor for Both Macrophage-tropic and T Cell Line-tropic HIV-1," *J. Exp. Med.* 185(11): 2015-2023 (1997).

Clapham, P.R. and R.A. Weiss, "Spoilt for Choice of Co-Receptors," *Nature* 388: 230-231 (1997).

Alkhatib, G. et al., "A New SIV Co-receptor, STRL33," *Nature* 388: 238 (1997).

Scarlatti, G. et al., "*In Vivo* Evolution of HIV-1 Co-receptor Usage and Sensitivity to Chemokine-Mediated Suppression," *Nature Medicine* 3(11): 1259-1265 (1997).

Edinger, A.L. et al., "CD4-independent, CCR5-dependent Infection of Brain Capillary Endothelial Cells by a Neurovirulent Simian Immunodeficiency Virus Strain," *Proc. Natl. Acad. Sci., USA* 94: 14742-14747 (1997).

(Continued)

*Primary Examiner*—Lorraine Spector
*Assistant Examiner*—Jon M Lockard
(74) *Attorney, Agent, or Firm*—Hamilton, Brook, Smith & Reynolds, P.C.

(57) ABSTRACT

The invention relates to an antibody or antigen-binding fragment thereof which binds to the CXC chemokine receptor Bonzo (also referred to as STRL33, TYMSTR, HBMBU14 and CXCR6) and blocks the binding of a ligand (e.g., SExCkine (also referred to as chemokine alpha-5 and CXCL16) to the receptor. The invention also relates to a method of identifying agents (molecules, compounds) which can bind to Bonzo and inhibit the binding of a ligand (e.g., SExCkine) and/or modulate a function of Bonzo. The invention further relates to a method of modulating a function of Bonzo, and to the use of the antibodies, antigen-binding fragments, targeting molecules and agents identified by the method of the invention in research, therapeutic, prophylactic and diagnostic methods.

60 Claims, 40 Drawing Sheets

OTHER PUBLICATIONS

Edinger, A.L. et al., "Use of GPR1, GPR15, and STRL33 as Coreceptors by Diverse Human Immunodeficiency Virus Type 1 and Simian Immunodeficiency Virus Envelope Proteins," *Virology* 249(2): 367-378 (1998).

Mörner, A. et al., "Primary Human Immunodeficiency Virus Type 2 (HIV-2) Isolates, Like HIV-1 Isolates, Frequently Use CCR5 but Show Promiscuity in Coreceptor Usage," *J. Virol.* 73(3): 2343-2349 (1999).

Zhang, Y-J. and J.P. Moore, "Will Multiple Coreceptors Need to be Targeted by Inhibitors of Human Immunodeficiency Virus Type 1 Entry?," *J. Virol.* 73(4): 3443-3448 (1999).

Deng, H. et al., "Expression Cloning of New Receptors Used by Simian and Human Immunodeficiency Viruses," *Nature* 388: 296-300 (1997).

Zhang, Y-J. et al. "Use of Coreceptors Other than CCR5 by Non-Syncytium-Inducing Adult and Pediatric Isolates of Human Immunodeficiency Virus Type 1 is Rare *In Vitro*," *J. Virol.* 72(11): 9337-9344 (1998).

Littman, D.R., "Chemokine Receptors: Keys to AIDS Pathogenesis?," *Cell* 93: 677-680 (1998).

Owen, S.M. et al., "Genetically Divergent Strains of Human Immunodeficiency Virus Type 2 Use Multiple Coreceptors for Viral Entry," *J. Virol.* 72(7): 5425-5432 (1998).

Ponath, P.D. et al., "Molecular Cloning and Characterization of a Human Eotaxin Receptor Expressed Selectively on Eosinophils," *J. Exp. Med.* 183: 2437-2448 (1996).

Wu, L. et al., "Discrete Steps in Binding and Signaling of Interleukin-8 with Its Receptor," *J. Biol. Chem.* 271 (49): 31202-31209 (1996).

Wu, L. et al., "CD4-Induced Interaction of Primary HIV-1 gp120 Glycoproteins with the Chemokine Receptor CCR-5," *Nature* 384:179-183 (1996).

Loetscher, M. et al., "TYMSTR, A Putative Chemokine Receptor Selectively Expressed in Activated T Cells Exhibits HIV-1 Coreceptor Function," *Current Biology* 7(9):652-660 (1997).

Jin, Y. et al., "The Regulation of Phenotype and Function of Human Liver CD3$^+$/CD56$^+$ Lymphocytes, and Cells That Also Co-Express CD8 by IL-2, IL-12 and Anti-CD3 Monoclonal Antibody," *Human Immunology* 59: 352-362 (1998).

Goldman, L.A. et al., "Modifications of Vectors pEF-BOS, pcDNA1 and pcDNA3 Result in Improved Convenience and Expression," *Biotechniques* 21(6):1013-1015 (1996).

Sornasse, T. et al., "Differentiation and Stability of T Helper 1 and 2 Cells Derived from Naive Human Neonatal CD4$^+$ T Cells, Analyzed at the Single-cell Level," *J. Exp. Med.* 184:473-483 (1996).

Wu, L., et al. "CCR5 Levels and Expression Pattern Correlate with Infectability by Macrophage-tropic HIV-1, In Vitro," *J. Exp. Med.* 185(9):1681-1691 (1997).

Yoshie, O., et al. "Novel Lymphocyte-Specific CC Chemokines and Their Receptors," *J. Leukoc. Biol.*, 62:634-644 (1997).

GenBank Accession No. AA290712, "zt18a10.r1 Soares Ovary Tumor NbHOT *Homo sapiens* cDNA Clone IMAGE:713466 5', mRNA Sequence," (1997) [online], [retrieved on Jul. 14, 1999]. Retrieved from the Internet: <URL:://www.ncbi.nlm.nih.gov>.

GenBank Accession No. AA283690, "zt18a10.s1 Soares Ovary Tumor NbHOT *Homo sapiens* cDNA Clone IMAGE:713466 3' Similar to Contains Element LTR8 Repetitive Element; mRNA Sequence," (1997) [online], [retrieved on Jul. 14, 1999]. Retrieved from the Internet: <URL:://www.ncbi.nlm.nih.gov>.

GenBank Accession No. AI312518, "qp10a09.xl NCI_CGAP_Kid5 *Homo sapiens* cDNA Clone IMAGE:1917592 3' Similar to Contains Alu Repetitive Element; Contains Element MSR1 Repetitive Element; mRNA Sequence," (1999) [online], [retrieved on Jul. 14, 1999]. Retrieved from the Internet: <URL:://www.ncbi.nlm.nih.gov>.

GenBank Accession No. AA366329, "EST77447 Pancreas Tumor III *Homo sapiens* cDNA 5' End, mRNA Sequence," (1997) [online], [retrieved on Jul. 14, 1999]. Retrieved from the Internet: <URL//www.ncbi.nlm.nih.gov>.

GenBank Accession No. AA146672, "zo33b12.r1 Stratagene Colon (#937204) *Homo sapiens* cDNA Clone IMAGE:588671 5', mRNA Sequence," (1996) [online], [retrieved on Jul. 14, 1999]. Retrieved from the Internet: <URL:://www.ncbi.nlm.nih.gov>.

GenBank Accession No. F14505, "SSC1C52 Porcine Small Intestine cDNA Library Sus scrofa cDNA, mRNA Sequence," (1996) [online], [retrieved on Jul. 14, 1999]. Retrieved from the Internet: <URL:://www.ncbi.nlm.nih.gov>.

GenBank Accession No. F23105, "SSC21H07 Porcine Small Intestine cDNA Library Sus scrofa cDNA Clone c21h07 5', mRNA Sequence," (1998) [online], [retrieved on Jul. 14, 1999]. Retrieved from the Internet: <URL:://www.ncbi.nlm.nih.gov>.

GenBank Accession No. AI019535, "ua90a07.r1 Soares Mouse Mammary Gland NbMMG Mus musculus cDNA Clone IMAGE:1364724 5', mRNA Sequence," (1998) [online], <URL:://www.ncbi.nlm.nih.gov>.

GenBank Accession No. AA121716, "zn95c09.r1 Stratagene Fetal Retina 937202 *Homo sapiens* cDNA Clone, IMAGE:565936 5', mRNA Sequence" (1997) [online], [retrieved on Jul. 14, 1999]. Retrieved from the Internet: <URL:://www.ncbi.nlm.nih.gov>.

GenBank Accession No. AA130776, "zo13d05.r1 Stratagene Colon (#937204) *Homo sapiens* cDNA Clone IMAGE:586761 5', mRNA Sequence," (1997) [online], [retrieved on Jul. 14, 1999]. Retrieved from the Internet: <URL:://www.ncbi.nlm.nih.gov>.

GenBank Accession No. AA130627, "zo13d05.s1 Stratagene Colon (#937204) *Homo sapiens* cDNA Clone IMAGE:586761 3' Similar to gb:M91159 !!!! ALU Class E Warning Entry !!!! (Human); Contains Element PTR5 Repetitive Element; mRNA Sequence," (1997) [online], [retrieved on Jul. 14, 1999]. Retrieved from the Internet: <URL:://www.ncbi.nlm.nih.gov>.

Chuntharapai, A. and Kim, K.J., "Generation of Monoclonal Antibodies to Chemokine Receptors," *Methods in Enzymology*, 288:15-27 (1997).

STRL 33/Bonzo Monoclonal Antibody MAB699, *de novo, New Products from R&D Systems*, p. 7 (1999).

Monoclonal Anti-human STRL 33/Bonzo Antibody, Technical Information, R&D Systems, Inc. (1999).

Shimaoka, T. et al., "Molecular Cloning of a Novel Scavenger Receptor for Oxidized Low Density Lipoprotein, SR-PSOX, on Macrophages," *J. Biol. Chem.* 275(52):40663-40666 (2000).

GenBank Accession No. AW347794, "32031 MARC 2PIG Sus scrofa cDNA 5', mRNA Sequence gi|6845504|gb|AW347794.1|AW347794 [6845504]," (2000) [online], [retrieved on Nov. 28, 2000]. Retrieved from the internet: <URL:://www.ncbi.nlm.nih.gov>.

GenBank Accession No. AW261653, "um90c04.x1 Sugano Mouse Kidney mkia Mus musculus cDNA Clone IMAGE:2332038 3', mRNA Sequence gi|6638469|gb|AW261653 [6638469]," (2000) [online], [retrieved on Nov. 28, 2000]. Retrieved from the internet: <URL//www.ncbi.nlm.nih.gov>.

Matloubian M. et al., "A Transmembrane CXC Chemokine is a Ligand for HIV-Coreceptor Bonzo," *Nature Immunol.* 1(4):298-304 (2000).

Sharron, M. et al., "Expression and Coreceptor Activity of STRL33/Bonzo on Primary Peripheral Blood Lymphocytes," *Blood* 96(1):41-49 (2000).

Unutmaz, D. et al., "The Primate Lentiviral Receptor Bonzo/STRL33 is Coordinately Regulated with CCR5 and its Expression Pattern is Conserved Between Human and Mouse," *J. Immunol.* 165 (6):3284-3292 (2000).

Ignatius, R. et al., "The Immunodeficiency Virus Coreceptor, Bonzo/STRL33/TYMSTR, is Expressed by Macaque and Human Skin- and Blood-Derived Dendritic Cells," AIDS Research and Human Retroviruses 16(11):1055-1059 (2000).

Copy of Priority Document for WO 99/27078, U.S. Appl. No. 60/066,369 entitled "Chemokine Alpha-5", by Wei, Y-F. et al., filed Nov. 21, 1997.

GenBank Accession No. M25897, "Human Platelet Factor 4 (PF4) mRNA, Complete Cds," (1995) [online], [retrieved on Mar. 30, 2001]. Retrieved from the internet: <URL://www.ncbi.nlm.nih.gov>.

GenBank Accession No. AF007545, "*Homo sapiens* SIV/HIV Receptor Bonzo (Bonzo) mRNA, Complete Cds," (1997) [online], [retrieved on Mar. 30, 2001]. Retrieved from the internet: <URL://www.ncbi.nlm.nih.gov>.

GenBank Accession No. U73531, "Human G Protein-Coupled Receptor STRL33.1 (STRL33) mRNA, Complete Cds," (1997) [online], [retrieved on Nov. 24, 1999]. Retrieved from the internet: <URL://www.ncbi.nlm.nih.gov>.

GenBank Accession No. NM_006564, "*Homo sapiens* G Protein-Coupled Receptor (TYMSTR) mRNA," (1999) [online], [retrieved on Nov. 24, 1999]. Retrieved from the internet: <URL://www.ncbi.nlm.nih.gov>.

GenBank Accession No. U73529, "Human G Protein-Coupled Receptor STRL33.3 (STRL33) mRNA, Complete Cds," (1997) [online], [retrieved on Nov. 24, 1999]. Retrieved from the internet: >URL://www.ncbi.nlm.nih.gov>.

Lee, B., et al., "Epitope Mapping of CCR5 Reveals Multiple Conformational States and Distinct but Overlapping Structures Involved in Chemokine and Coreceptor Function," *J. Biol. Chem.*, 274(14):9617-9626 (1999).

Wu, L., et al., "Interaction of Chemokine Receptor CCR5 with its Ligands: Multiple Domains for HIV-1 gp120 Binding and a Single Domain for Chemokine Binding," *J. Exp. Med.*, 186(8):1373-1381 (1997).

Yoshimura, A., et al., "Negative Regulation of Cytokine Signaling Influences Inflammation," *Curr. Opin. Immunol.*, 15:704-708 (2003).

Choy, E. H. S. and Panayi, G. S., "Cytokine Pathways and Joint Inflammation in Rheumatoid Arthritis," *N. Engl. J. Med.*, 344(12):907-916 (2001).

Doranz, B. J., et al., "Identification of CXCR4 Domains That Support Coreceptor and Chemokine Receptor Functions," *J. Virol.*, 73(4):2752-2761 (1999).

Hesselgesser, J., et al., "Identification and Characterization of Small Molecule Functional Antagonists of the CCR1 Chemokine Receptor," *J. Biol. Chem.*, 273(25):15687-15692 (1998).

\* cited by examiner

FIG. 1

```
   1 atggcagagc atgattacca tgaagactat gggttcagca gtttcaatga cagcagccag
  61 gaggagcatc aagacttcct gcagttcagc aaggtctttc tgccctgcat gtacctggtg
 121 gtgtttgtct gtggtctggt ggggaactct ctggtgctgg tcatatccat cttctaccat
 181 aagttgcaga gcctgacgga tgtgttcctg gtgaacctac ccctggctga cctggtgttt
 241 gtctgcactc tgccottctg ggcctatgca ggcatccatg aatgggtgtt tggccaggtc
 301 atgtgcaaga gcctactggg catctacact attaacttct acacgtccat gctcatcctc
 361 acctgcatca ctgtggatcg tttcattgta gtggttaagg ccaccaaggc ctacaaccag
 421 caagccaaga ggatgacctg gggcaaggtc accagcttgc tcatctgggt gatatccctg
 481 ctggtttcct tgccccaaat tatctatggc aatgtcttta gctcgacaa gctcatatgt
 541 ggttaccatg acgaggcaat tccactgtg gttcttgcca cccagatgac actggggttc
 601 ttcttgccac tgctcaccat gattgtctgc tattcagtca taatcaaaac actgcttcat
 661 gctggaggct tccagaagca cagatctcta aagatcatct tcctggtgat ggctgtgttc
 721 ctgctgacca gatgccctt caacctcatg aagttcatcc gcagcacaca ctgggaatac
 781 tatgccatga ccagctttca ctacaccatc atggtgacag aggccatcgc atacctgagg
 841 gcctgcctta accctgtgct ctatgccttt gtcagcctga gtttcgaaa gaacttctgg
 901 aaacttgtga aggacatgg ttgcctccct tacctggggg tctcacatca atggaaatct
 961 tctgaggaca attccaagac tttttctgcc tcccacaatg tggaggccac cagcatgttc
1021 cagttatag
```

FIG. 2

```
MAEHDYHEDY GFSSFNDSSQ EEHQDFLQFS KVFLPCMYLV VFVCGLVGNS LVLVISIFYH KLQSLIDVFL
VNLPLADLVF VCTLPFWAYA GIHEWVFGQV MCKSLLGIYT INFYTSMLIL TCITVDRFIV VVKATKAYNQ
QAKRMTWGKV TSLLIWVISL LVSLPQIIYG NVFNLDKLIC GYHDEAISTV VLATQMTLGF FLPLLTMIVC
YSVIIKTLLH AGGFQKHRSL KIIFLVMAVF LLTQMPFNLM KFIRSTHWEY YAMTSFHYTI MVTEAIAYLR
ACLNPVLYAF VSLKFRKNFW KLVKDIGCLP YLGVSHQWKS SEDNSKTFSA SHNVEATSMF QL
```

```
1.
    CGGCGACTCTCTCCACCGGGCCGCCCGGGAGGCTCATGCAGCGCGGCTGGGTCCCGCGGC
61
    GCCCGGATCGGGGAAGTGAAAGTGCCTCGGAGGAGGAGGGCCGGTCCGGCAGTGCAGCCG
121
    CCTCACAGGTCGGCGGACGGGCCAGGCGGGCGGCCTCCTGAACCGAACCGAATCGGCTCC
181
    TCGGGCCGTCGTCCTCCCGCCCCTCCTCGCCCGCCGCCGGAGTTTTCTTTCGGTTTCTTC
241
    CAAGATTCCTGGCCTTCCCTCGACGGAGCCGGGCCCAGTGCGGGGCGCAGGGCGCGGGA
301
    GCTCCACCTCCTCGGCTTTCCCTGCGTCCAGAGGCTGGCATGGCGCGGGCCGAGTACTGA
361
    GCGCACGGTCGGGGCACAGCAGGGCCGGTGGGTGCAGCTGGCTCGCGCCTCCTCTCCGGC
421
    CGCCGTCTCCTCCGGTCCCCGGCGAAAGCCATTGAGACACCAGCTGGACGTCACGCGCCG
481
    GAGCATGTCTGGGAGTCAGAGCGAGGTGGCTCCATCCCCGCAGAGTCCGCGGAGCCCCGA
541
    GATGGGACGGGACTTGCGGCCCGGGTCCCGCGTGCTCCTGCTCCTGCTTCTGCTCCTGCT
       M  G  R  D  L  R  P  G  S  R  V  L  L  L  L  L  L  L  L  L         20
601
    GGTGTACCTGACTCAGCCAGGCAATGGCAACGAGGGCAGCGTCACTGGAAGTTGTTATTG
     V  Y  L  T  Q  P  G  N  G  N  E  G  S  V  T  G  S  C  Y  C          40
661
    TGGTAAAAGAATTTCTTCCGACTCCCCGCCATCGGTTCAGTTCATGAATCGTCTCCGGAA
      G  K  R  I  S  S  D  S  P  P  S  V  Q  F  M  N  R  L  R  K         60
721
    ACACCTGAGAGCTTACCATCGGTGTCTATACTACACGAGGTTCCAGCTCCTTTCCTGGAG
      H  L  R  A  Y  H  R  C  L  Y  Y  T  R  F  Q  L  L  S  W  S         80
781
    CGTGTGTGGAGGCAACAAGGACCCATGGGTTCAGGAATTGATGAGCTGTCTTGATCTCAA
      V  C  G  G  N  K  D  P  W  V  Q  E  L  M  S  C  L  D  L  K        100
```

FIG. 4B

```
841
     AGAATGTGGACATGCTTACTCGGGGATTGTGGCCCACCAGAAGCATTTACTTCCTACCAG
      E  C  G  H  A  Y  S  G  I  V  A  H  Q  K  H  L  L  P  T  S    120
901
     CCCCCCAACTTCTCAGGCCTCAGAGGGGGCATCTTCAGATATCCACACCCCTGCCCAGAT
      P  P  T  S  Q  A  S  E  G  A  S  S  D  I  H  T  P  A  Q  M    140
961
     GCTCCTGTCCACCTTGCAGTCCACTCAGCGCCCCACCCTCCCAGTAGGATCACTGTCCTC
      L  L  S  T  L  Q  S  T  Q  R  P  T  L  P  V  G  S  L  S  S    160
1021
     GGACAAAGAGCTCACTCGTCCCAATGAAACCACCATTCACACTGCGGGCCACAGTCTGGC
      D  K  E  L  T  R  P  N  E  T  T  I  H  T  A  G  H  S  L  A    180
1081
     AGTTGGGCCTGAGGCTGGGGAGAACCAGAAGCAGCCGGAAAAAAATGCTGGTCCCACAGC
      V  G  P  E  A  G  E  N  Q  K  Q  P  E  K  N  A  G  P  T  A    200
1141
     CAGGACATCAGCCACAGTGCCGGTCCTGTGCCTCCTGGCCATCATCTTCATCCTCACCGC
      R  T  S  A  T  V  P  V  L  C  L  L  A  I  I  F  I  L  T  A    220
1201
     AGCCCTTTCCTATGTGCTGTGCAAGAGGAGGAGGGGGCAGTCACCGCAGTCCTCTCCAGA
      A  L  S  Y  V  L  C  K  R  R  R  G  Q  S  P  Q  S  S  P  D    240
1261
     TCTGCCGGTTCATTATATACCTGTGGCACCTGACTCTAATACCTGAGCCAAGAATGGAAG
      L  P  V  H  Y  I  P  V  A  P  D  S  N  T  *                   254
1321
     CTTGTGAGGAGACGGACTCTATGTTGCCCAGGCTGTTATGGAACTCCTGAGTCAAGTGAT
1381
     CCTCCCACCTTGGCCTCTGAAGGTGCGAGGATTATAGGCGTCACCTACCACATCCAGCCT
1441
     ACACGTATTTGTTAATATCTAACATAGGACTAACCAGCCACTGCCCTCTCTTAGGCCCCT
```

FIG. 4C

```
1501
       CATTTAAAAACGGTTATACTATAAAATCTGCTTTTCACACTGGGTGATAATAACTTGGAC
1561
       AAATTCTATGTGTATTTTGTTTTGTTTTGCTTTGCTTTGTTTTGAGACGGAGTCTCGCTC
1621
       TGTCATCCAGGCTGGAGTGCAGTGGCATGATCTCGGCTCACTGCAACCCCCATCTCCCAG
1681
       GTTCAAGCGATTCTCCTGCCTCCTCCTAAGTAGCTGGGACTACAGGTGCTCACCACCACA
1741
       CCCGGCTAATTTTTTGTATTTTTAGTAGAGACGGGGTTTCACCATGTTGACCAGGCTGGT
1801
       CTCGAACTCCTGACCTGGTGATCTGCCCACCCAGGCCTCCCAAAGTGCTGGGATTAAAGG
1861
       TGTGAGCCACCATGCCTGGCCCTATGTGTGTTTTTAACTACTAAAAATTATTTTTGTAA
1921
       TGATTGAGTCTTCTTTATGGAAACAACTGGCCTCAGCCCTTGCGCCCTTACTGTGATTCC
1981
       TGGCTTCATTTTTTGCTGATGGTTCCCCCTCGTCCCAAATCTCTCTCCCAGTACACCAGT
2041
       TGTTCCTCCCCCACCTCAGCCCTCTCCTGCATCCTCCTGTACCCGCAACGAAGGCCTGGG
2101
       CTTTCCCACCCTCCCTCCTTAGCAGGTGCCGTGCTGGGACACCATACGGGTTGGTTTCAC
2161
       CTCCTCAGTCCCTTGCCTACCCCAGTGAGAGTCTGATCTTGTTTTTATTGTTATTGCTTT
2221
       TATTATTATTGCTTTTATTATCATTAAAACTCTAGTTCTTGTTTTGTCTCTCAAAAAAAA
2281
       AAAAAAAAAAAAAAAAAAAAAAAAAAAA
```

FIG. 5

```
  1 ccgcagcatg agctccgcag ccgggttctg cgcctcacgc cccgggctgc tgttcctggg
 61 gttgctgctc ctgccacttg tggtcgcctt cgccagcgct gaagctgaag aagatggggga
121 cctgcagtgc ctgtgtgtga agaccacctc ccaggtccgt cccaggcaca tcaccagcct
181 ggaggtgatc aaggccggac cccactgccc cactgcccaa ctgatagcca cgctgaagaa
241 tggaaggaaa atttgcttgg acctgcaagc cccgctgtac aagaaaataa ttaagaaact
301 tttggagagt tagctactag ctgcctacgt gtgtgcattt gctatatagc atacttcttt
361 tttccagttt caatctaact gtgaaagaaa cttctgatat ttgtgttatc cttatgattt
421 taaataaaca aaataaatc
```

FIG. 6

MSSAAGFCAS RPGLLFLGLL LLPLVVAFAS AEAEEDGDLQ CLCVKTTSQV RPRHITSLEV IKAGPHCPTA
QLIATLKNGR KICLDLQAPL YKKIIKKLLE S

4A11
(IgG2b)

7A2
(IgG2a)

7F3
(IgG2a)

9G2
(IgM)

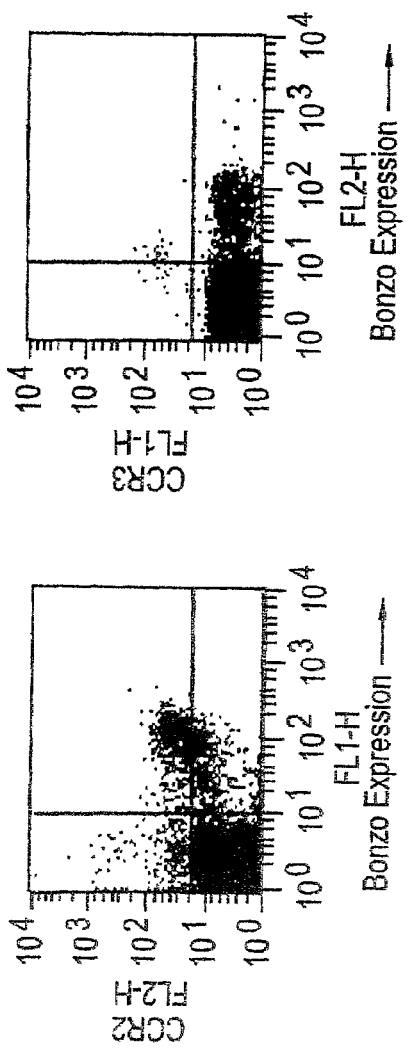
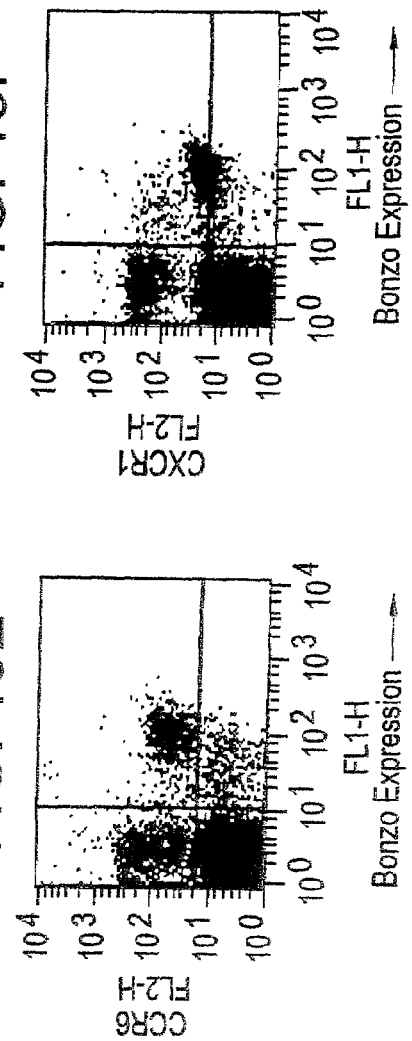

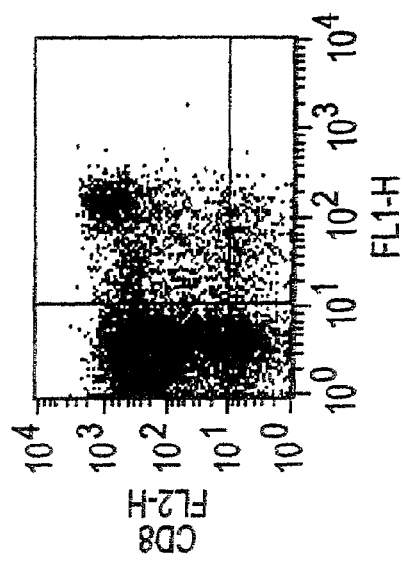
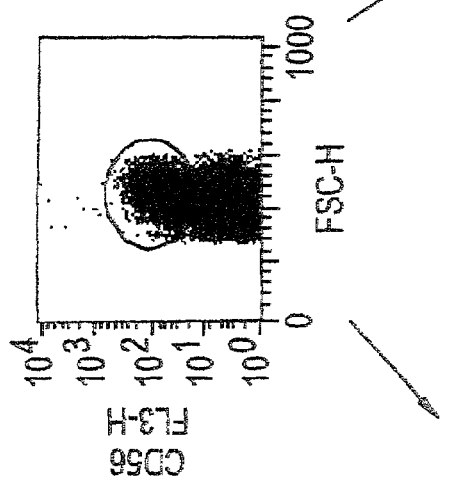
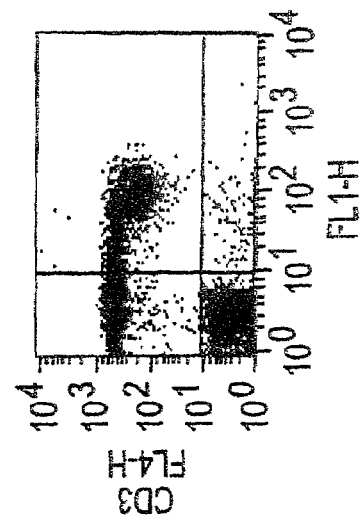

4A11-30-8
anti-Bonzo
(IgG2b)

7F3-8-1
anti-Bonzo
(IgG2a)

7A2-32-1
anti-Bonzo
(IgG2a)

7H12-12-2
anti-CCR7
(IgG2b)

CD3 Blasts

LAK Cells

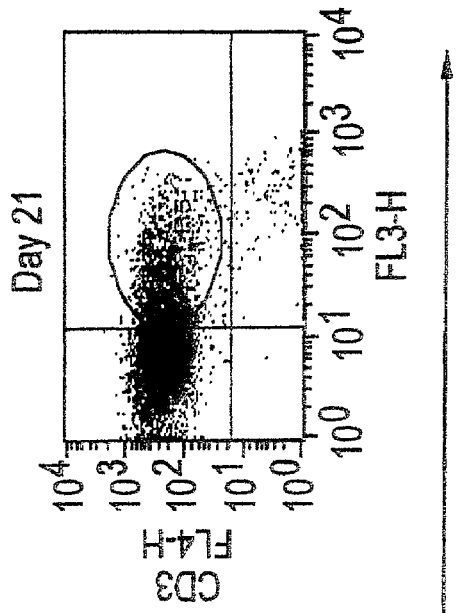
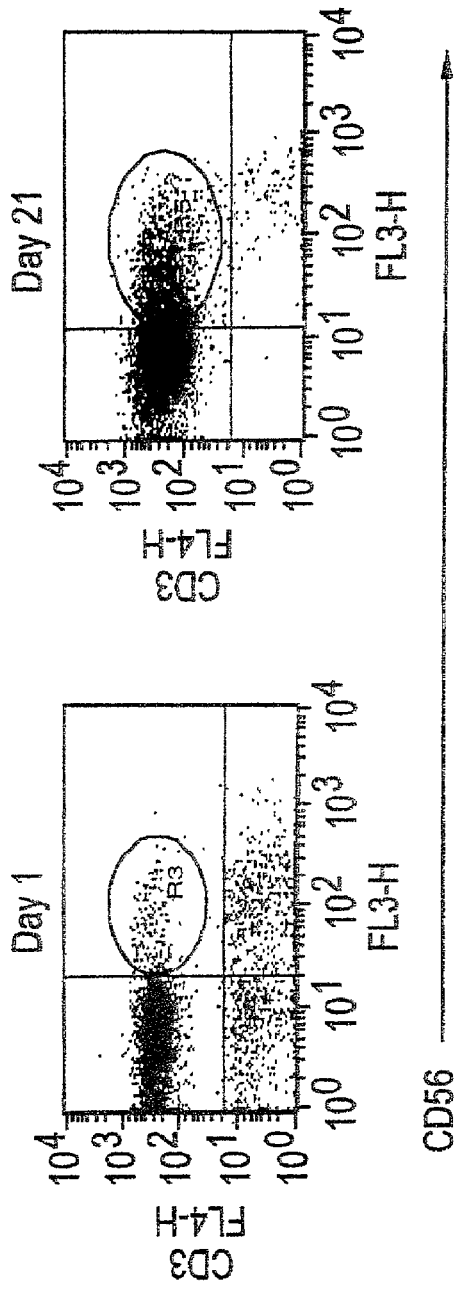
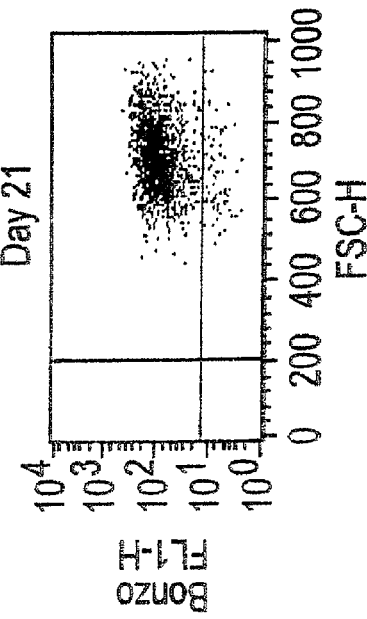
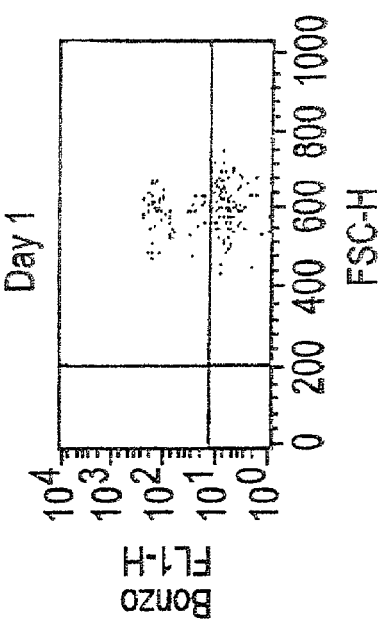

MOPC

4A11 anti-Bonzo

7F3
anti-Bonzo

1G1
anti-CCR4

$T_H 1$ — CCR4

$T_H 1$ — CCR4

$T_H 1$ — Bonzo $T_H 1$ — Bonzo $T_H 1$ — CCR7

$T_H 1$ — CCR7

T$_H$2 / CCR4

T$_H$2 / CCR4

T$_H$2 / Bonzo

T$_H$2 / Bonzo

T$_H$2 / CCR7

T$_H$2 / CCR7

$T_R^1$ $T_R^1$ $T_R^1$ $T_R^1$ $T_R^1$ $T_R^1$

US 7,038,018 B2

ANTIBODIES AND LIGANDS FOR "BONZO" CHEMOKINE RECEPTOR

RELATED APPLICATIONS

This application is a divisional of U.S. application Ser. No. 09/449,437, filed Nov. 24, 1999 (now U.S. Pat. No. 6,319,675 B1), the entire teachings of which are incorporated herein by reference.

BACKGROUND OF THE INVENTION

Chemokines are a large and growing family of 6–14 kD (non-glycosylated) proteins that mediate a wide range of biological functions (Taub, D. D. and Openheim, J. J., *Ther. Immunol.*, 1:229–246 (1994)). The chemokines can be divided into families based on the position of four cysteine residues that form two disulfide bonds (Kelner, G. S., et al., *Science*, 266:12395–1399 (1994); Bazan, J. F., et al., *Nature*, 385:640–644 (1997); Pin, Y., et al., *Nature*, 385:611–617 (1997)). Chemokine receptors can also be divided into families based on the type of chemokine they bind, although, no clear structural differences have been identified that distinguish the receptor sub-families (Mackay, C. R., *J. Exp. Med.*, 184:799–802 (1996)). In addition, there are a number of so-called "orphan" chemokine receptors (e.g., Bonzo) which share sequence homology with well-characterized chemokine receptors, but for which the biological functions and specific receptor agonists remain unknown.

Chemokines play a vital role in leukocyte adhesion and extravasation. For example, in various in vitro assays, chemokines can induce the chemotaxis or transendothelial migration of leukocytes (Taub, D. D. and Oppenheim, J. J., *Ther. Immunol.*, 1:229–246 (1994)), while in vivo injection (Taub, D. D., et al. *J. Clin. Invest.*, 97:1931–1941 (1996)) or over-expression of chemokines (Fuentes, M. E., et al., *J. Immunol.*, 155:5769–5776 (1995)) can result in leukocyte accumulation at the site of chemokine injection or expression. Antagonists of chemokines can prevent leukocyte trafficking (Bargatze, R. F. and Butcher, E. C., *J. Exp. Med.*, 178:367–372 (1993)) and may have beneficial effects in several models of acute and chronic inflammation (Sekido, N., et al., *Nature*, 365:654–657 (1993); Karpus, W. J., et al., *J. Immunol*, 155:5003–5010 (1995)). Chemokines have also been reported to modulate angiogenesis (Gupta, S. K., et al., *Proc. Natl. Acad. Sci. USA*, 92:7799–7803 (1995) and hematopoiesis (Taub, D. D. and Openheim, J. J., *Ther. Immunol.*, 1:229–246 (1994)), as well as T lymphocyte activation (Zhou, Z., et al., *J. Immunol* 151:4333–4341 (1993); Taub, D. D., et al., *J. Immunol.*, 156:2095–2103 (1996)). In addition, several chemokine receptors act as co-receptors, along with CD4, for entry of M tropic and T tropic HIV-1 (Choe, H., et al., *Cell*, 85:1135–1148 (1996); Feng, Y., et al., *Science*, 272:872–877 (1996)).

Leukocyte adhesion to endothelium is thought to involve several overlapping steps including rolling, activation and arrest. Rolling leukocytes are exposed to factors expressed at the adhesion site resulting in activation of the leukocyte and up-regulation of integrin-mediated adhesion. As a consequence of such integrin-mediated interactions, leukocytes arrest on the endothelium (Bargatze, R. F. and Butcher, E. C., *J. Exp. Med.*, 178:367–372 (1993); Bargatze, R. F., et al., *Immunity*, 3:99–108 (1995)). Leukocyte activation and up-regulation of integrin molecules occurs via a pertussis toxin sensitive mechanism that is thought to involve chemokine receptors (Bargatze, R. F. and Butcher, E. C., *J. Exp. Med.*, 178:367–372 (1993); Campbell, J. J., et al., *Science*, 279: 381–383 (1998)).

Memory $CD4^+$ lymphocytes can be grouped based upon the expression of certain chemokine receptors. For example, CXCR3, CCR2 and CCR5 (Qin, S., et al., *Eur. J. Immunol.*, 26:640–647 (1996); Qin, S., et al., *J. Clin. Invest.*, 101: 746–754 (1998); Liao, F., et al., *J. Immunol.*, 162:186–194 (1999)) are all expressed on subsets of memory CD4 lymphocytes, and certain chemokines act selectively on naive T cells (Adema, G. J., et al., *Nature*, 387:713–717 (1997)). Furthermore, several chemokines which are ligands for such receptors have been shown to be expressed in inflammatory sites (Gonzalo, J. A., et al., *J. Clin. Invest.*, 98:2332–2345 (1996)) and in some cases in lymph nodes draining a challenged site (Tedla, N., et al., *J. Immunol.*, 161:5663–5672 (1998)). In vitro derived $T_H1/T_H2$ lymphocyte lines have also been shown to differentially express chemokine receptors. Specifically, $T_H1$ lymphocytes have been shown to selectively express CXCR3 and CCR5, while $T_H2$ lymphocytes selectively express CCR4, CCR8 and CCR3 (Bonecchi, R. G., et al., *J. Exp. Med.*, 187:129–134 (1998); Sallusto, F. D., et al., *J. Exp. Med.*, 187:875–883 (1998); Sallusto, F., *Science*, 277:2005–2007 (1997); Andrew, D. P., et al., *J. Immunol* 161:5027–5038 (1998); Zingoni, A., et al., *J. Immunol.*, 161:547–555 (1998)). Interestingly, in some cases the chemokines for these respective chemokine receptors, such as MDC for CCR4 and IP-10 for CXCR3, are induced by cytokines associated with a $T_H1/T_H2$ environment (Andrew, D. P., et al., *J. Immunol* 161: 5027–5038(1998); Luster, A. D., et al., *Nature*, 315:672–676 (1985)).

SUMMARY OF THE INVENTION

The invention relates to antibodies (immunoglobulins) and antigen-binding fragments thereof which bind mammalian Bonzo or portion of the receptor. In one embodiment, the antibody or antigen-binding fragment thereof binds human Bonzo. In another embodiment, the antibody or antigen-binding fragment thereof can inhibit the binding of ligand (e.g., SExCkine (Spleen Extracted Chemokine) also referred to as chemokine alpha-5 (WO 99/27078)) to a mammalian Bonzo. In a preferred embodiment, the antibody or antibody-binding fragment can bind human Bonzo and inhibit the binding of SExCkine to the receptor. In another embodiment, the antibody or antigen-binding fragment can bind Bonzo expressed on the membrane of a cell and inhibit a cellular response to binding of ligand to Bonzo.

In another embodiment, the antibody or antigen-binding fragment of the invention binds to an epitope which is the same as or is similar to the epitope recognized by mAb 4A11, mAb 7A2, mAb 7F3, mAb 9G2 or an antigen-binding fragment of any of the foregoing. In another embodiment, the binding of the antibody or antigen-binding fragment of the invention to human Bonzo can be inhibited by mAb 4A11, mAb 7A2 or mAb 7F3. In another embodiment, the antibody is mAb 4A11, mAb 7A2, mAb 7F3, mAb 9G2 or an antigen-binding fragment of any of the foregoing.

The invention also relates to an isolated cell that produces an antibody or antigen-binding fragment of the present invention, including those which bind to mammalian Bonzo and inhibit the binding of a ligand to the receptor. In one embodiment, the isolated cell is murine hybridoma 4A11 (also referred to as murine hybridoma LS212-4A11-30-8) deposited under ATCC Accession No. PTA-991. In another embodiment, the isolated cell is murine hybridoma 7A2

(also referred to as murine hybridoma LS212-7A2-32-1) deposited under ATCC Accession No. PTA-992. In another embodiment, the isolated cell is murine hybridoma 7F3 (also referred to as murine hybridoma LS212-7F3-8-7) deposited under ATCC Accession No. PTA-990. In another embodiment, the isolated cell is murine hybridoma 9G2 (also referred to as murine hybridoma LS212-9G2-7-2).

The invention also relates to antibodies (immunoglobulin) and antigen-binding fragments thereof (e.g., an antigen-binding fragment) which bind mammalian SExCkine. In one embodiment, the antibody or antigen-binding fragment thereof binds human SExCkine. In another embodiment, the antibody or antigen-binding fragment thereof can inhibit the binding of SExCkine to receptor. In a preferred embodiment, the antibody or antibody-binding fragment can bind human SExCkine and inhibit the binding of SExCkine to Bonzo.

The invention also relates to a method of detecting or identifying an agent (i.e., molecule or compound) which binds to mammalian Bonzo. In one embodiment, an agent which can bind to mammalian Bonzo and inhibit (reduce or prevent) the binding of a ligand (e.g., SExCkine) to Bonzo is identified in a competitive binding assay. In other embodiments, agents for use in therapy are identified in a direct binding assay. Thus, the invention encompasses methods of identifying agents which modulate Bonzo function, such as ligands or other substances which bind a mammalian Bonzo, including inhibitors (e.g., antagonists) or promoters (e.g., agonists) of receptor function. A suitable source of a mammalian Bonzo or a ligand-binding variant thereof can be used to identify a Bonzo binding agent in accordance with the method of the invention. In one embodiment, a cell (e.g., cell line, recombinant cell) that expresses a mammalian Bonzo or a ligand binding variant thereof is used. In another embodiment, a membrane preparation of a cell that expresses a mammalian Bonzo or a ligand binding variant thereof is used.

The invention also relates to therapeutic methods in which agents which can bind to a mammalian Bonzo and modulate (inhibit or promote) a Bonzo function are administered to a subject in need of such therapy. In one embodiment, the therapeutic method is a method of treating a subject having an inflammatory disease. In another embodiment, the subject has a cancer or an infection (e.g., viral, bacterial, fungal). In another embodiment, the therapeutic method is a method of inhibiting a cellular response (e.g., $Ca^{2+}$ flux, chemotaxis, exocytosis, respiratory burst). In another embodiment, the method is a method of modulating a Bonzo function. In another embodiment, SExCkine is locally administered to a subject to recruit Bonzo$^+$ cells to the area of administration.

The invention also relates to therapeutic methods in which antibodies or antigen-binding fragments thereof which bind to SExCkine and inhibit binding of SExCkine to receptor are administered to a subject in need of such therapy. In one embodiment, the therapeutic method is a method of treating a subject having an inflammatory disease.

The invention also relates to targeting molecules that can effectuate the interaction of a Bonzo$^+$ cell with a target cell. The targeting molecule can include a first binding moiety which binds Bonzo expressed on the surface of a cell and a second binding moiety which binds an antigen expressed on the surface of a target cell. In one embodiment, the first binding moiety is SExCkine or a receptor-binding variant thereof, and the second binding moiety is an antibody or antigen-binding fragment thereof which binds a tumor antigen or a viral antigen.

The invention also relates to therapeutic methods in which targeting molecules are administered to a subject in need of such therapy. In one embodiment, the therapeutic method is a method of treating a subject having a tumor or a viral infection.

The invention further relates to a method for detecting or quantifying a mammalian Bonzo or a portion thereof in a biological sample. The method comprises combining a biological sample and an agent which binds mammalian Bonzo (e.g., SExCkine, anti-Bonzo antibody or antigen-binding fragment of the invention) under conditions suitable for binding, and detecting a complex formed between Bonzo and the agent. In one embodiment, the biological sample comprises human cells or a fraction of said cells (e.g., membrane preparation).

The invention further relates to a method for detecting or quantifying a mammalian SExCkine or portion thereof in a biological sample. The method comprises contacting a biological sample and an antibody or antigen-binding fragment of the invention under conditions suitable for binding, and detecting a complex formed between SExCkine and the antibody or antigen-binding fragment.

The invention also relates to a test kit for identifying or quantifying a mammalian Bonzo or a portion thereof in a biological sample. In one embodiment, the kit comprises an antibody of the invention and suitable ancillary reagents.

The invention also relates to a test kit for identifying or quantifying a mammalian SExCkine or a portion thereof in a biological sample. In one embodiment, the kit comprises an antibody of the invention and suitable ancillary reagents.

The present invention further relates to an antibody, antigen-binding fragment, targeting molecule or agent as described herein for use in therapy (including prophylaxis) or diagnosis, and to the use of such an antibody, antigen-binding fragment, targeting molecule or agent for the manufacture of a medicament for the treatment of a particular disease or condition as described herein (e.g., an inflammatory disease, cancer, infection (e.g., viral, bacterial, fungal)).

The invention further relates to isolated nucleic acids encoding the antibodies and targeting molecules of the invention, and to recombinant constructs and host cells comprising nucleic acids encoding the antibodies and targeting molecules of the invention.

BRIEF DESCRIPTION OF THE DRAWINGS

FIG. 1 illustrates the nucleic acid sequence of a cDNA encoding human (*Homo sapiens*) Bonzo (SEQ ID NO:1) deposited in GenBank under Accession Number AF007545, having an open-reading frame beginning at position 1.

FIG. 2 illustrates the amino acid sequence of human Bonzo polypeptide (SEQ ID NO:2) encoded by the DNA sequence shown in FIG. 1 (SEQ ID NO:1).

FIG. 3 illustrates the nucleic acid sequence of a cDNA encoding human SExCkine (SEQ ID NO:3) and the amino acid sequence of the encoded human SExCkine polypeptide (SEQ ID NO:4). The cloned cDNA consists of 1763 nucleotides with an open reading frame encoding 254 amino acids. The open reading frame includes a predicted signal peptide of 29 amino acids (amino acid residues 1–29 of SEQ ID NO:4, underlined), a predicted membrane proximal mucin domain (amino acid residues 118–201 of SEQ ID NO:4, boxed), a predicted transmembrane segment (amino acid residues 202–226 of SEQ ID NO:4, underlined) and a cytoplasmic tail (amino acid residues 227–254 of SEQ ID NO:4).

FIGS. 4A–4C illustrate the nucleic acid sequence of a cDNA encoding human chemokine alpha-5 (SEQ ID NO:5)

(WO 99/27078) and the amino acid sequence (FIGS. 4A and 4B) of the encoded human chemokine alpha-5 polypeptide (SEQ ID NO:6).

FIG. 5 illustrates the nucleic acid sequence of a cDNA encoding human platelet factor-4 (SEQ ID NO:7) deposited in GenBank under Accession Number M25897, having an open-reading frame beginning at position 8.

FIG. 6 illustrates the amino acid sequence of human platelet factor-4 precursor polypeptide (SEQ ID NO:8) encoded by the DNA sequence shown in FIG. 5 (SEQ ID NO:7). Mature human platelet factor-4 consists of amino acid residues 32–101 (Poncz, M., et al., *Blood,* 69:219–223 (1987)).

Figure 7:
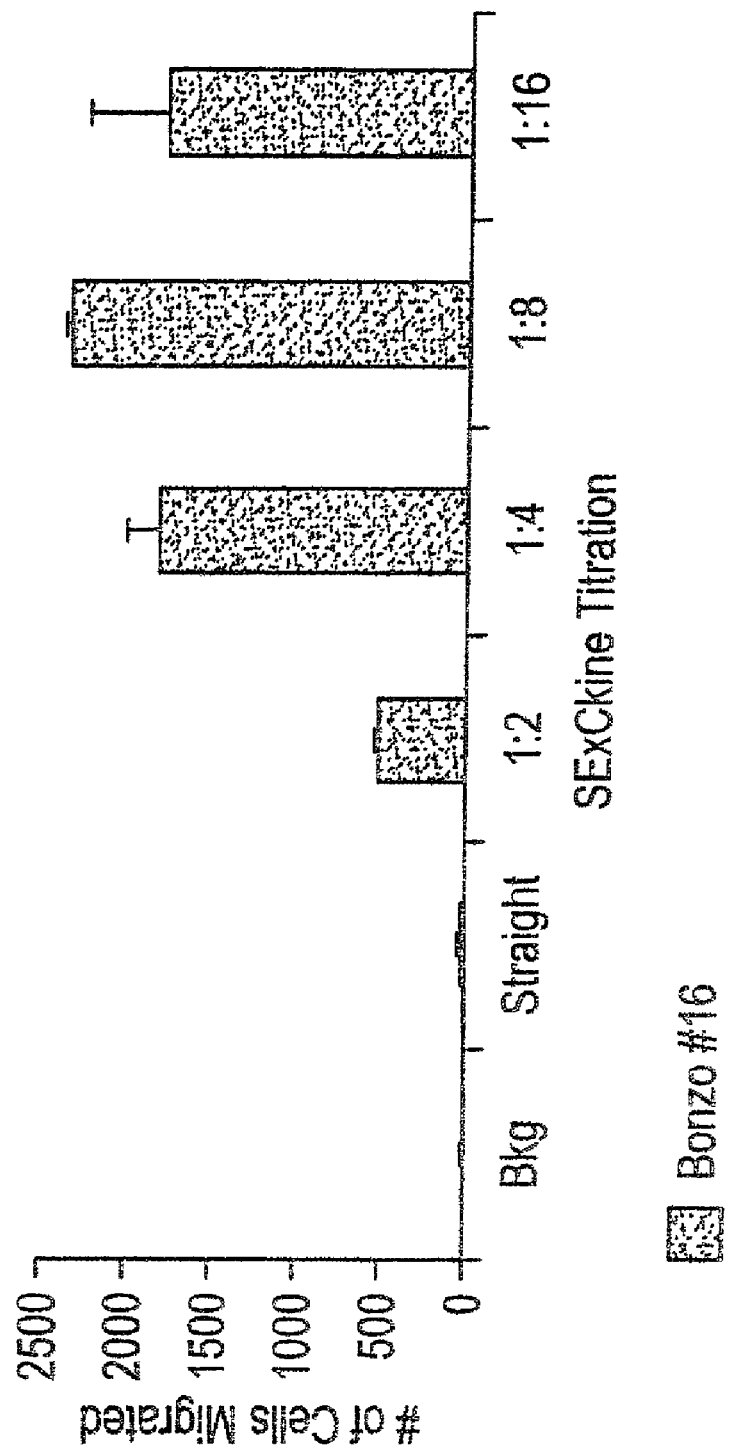
Figure 8A:
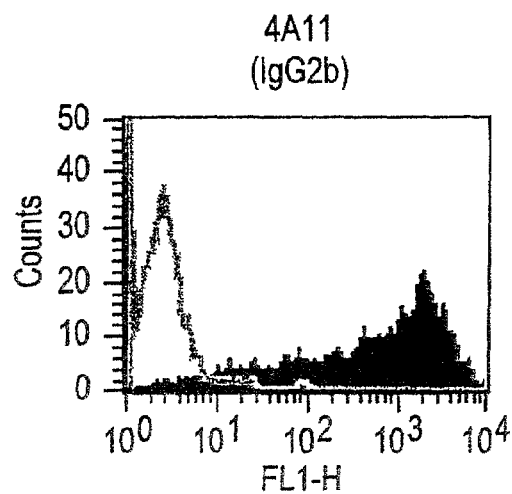
Figure 8B:
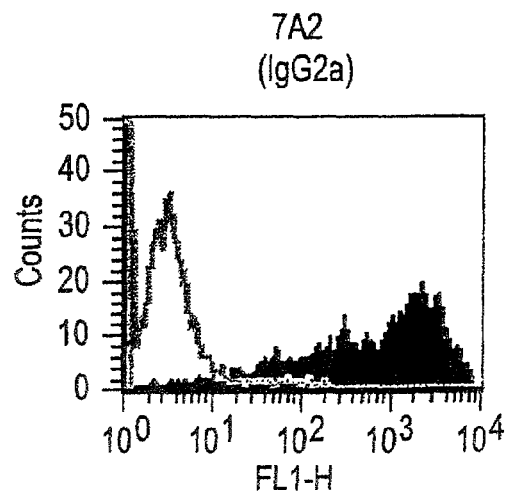
Figure 8C:
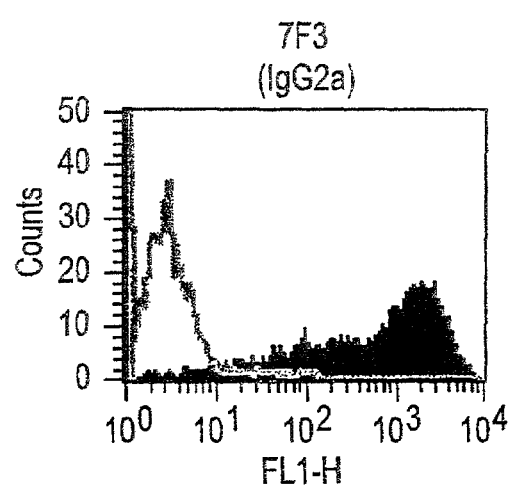
Figure 8D:
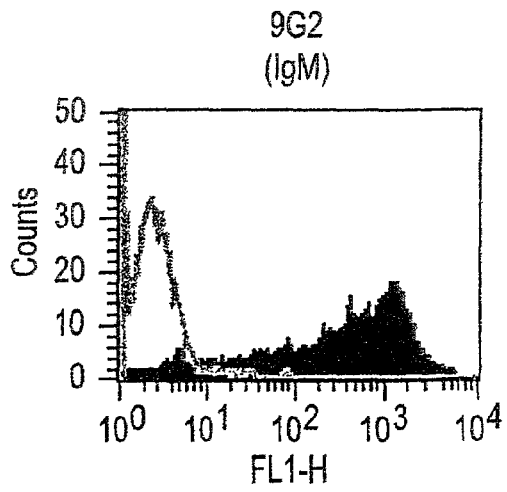
Figure 9A:
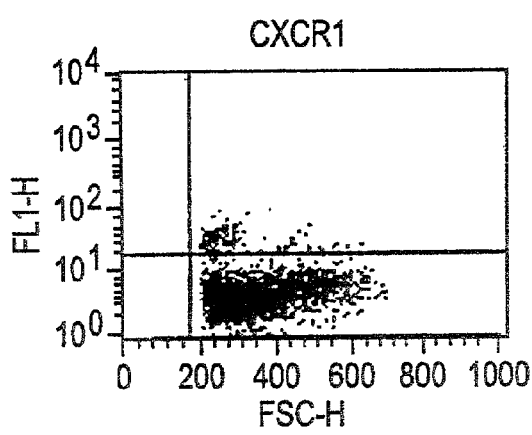
Figure 9C:
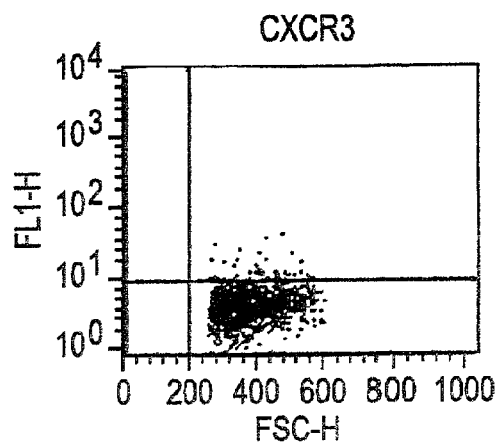
Figure 9B:
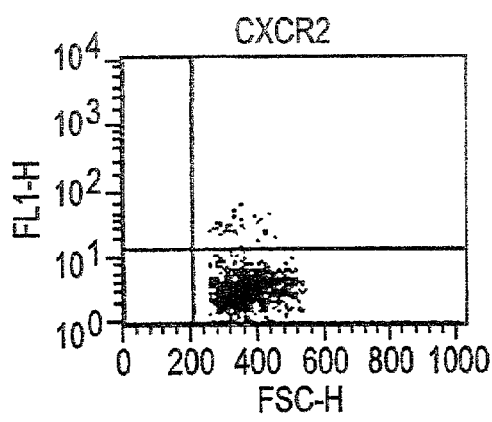
Figure 9D:
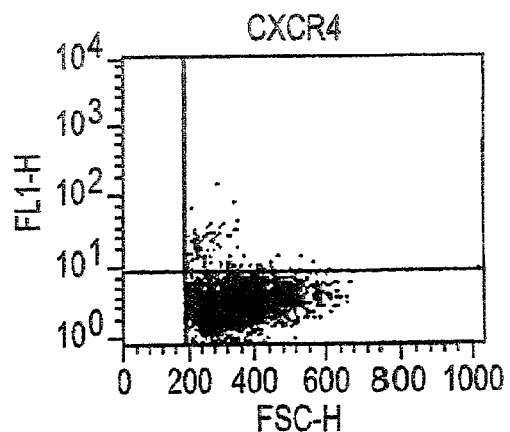
Figure 9E:
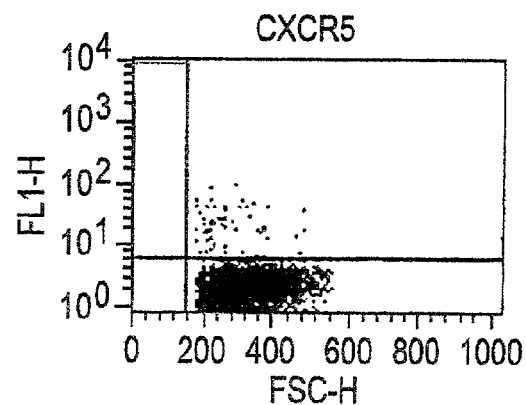
Figure 9F:
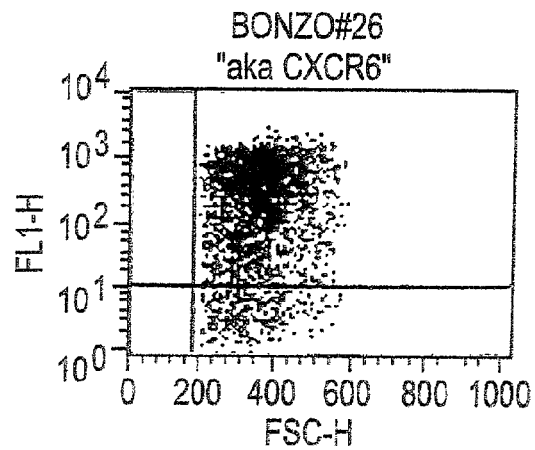
Figure 9G:
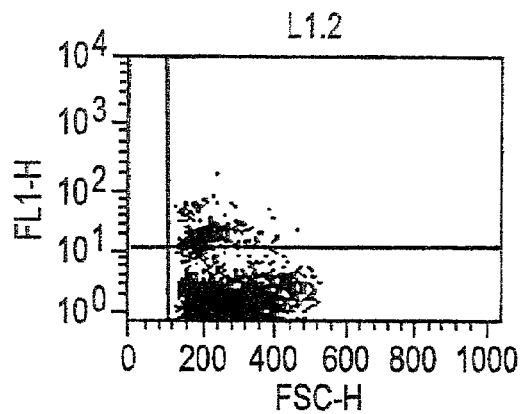

FIG. 7 is a histogram showing that transfected L1.2 cells which express Bonzo (Bonzo/L1.2) undergo SExCkine-induced chemotaxis. Bonzo/L1.2 cells were assayed for chemotactic response to undiluted culture supernatant of 293T cells transiently transfected with SExCkine (Straight) or to various dilutions of the supernatant (1:2, 1:4, 1:8 and 1:16). Bkg: chemotaxis in the presence of assay media without chemokine.

FIGS. 8A–8D are fluorescence plots showing that mAb 4A11, mAb 7A2, mAb 7F3 and mAb 9G2 each bind to Bonzo/L1.2 cells.

FIGS. 9A–9G are fluorescence plots showing that mAb 7F3 binds to Bonzo/L1.2 cells but not to L1.2 cells that express CXCR1, CXCR2, CXCR3, CXCR4, CXCR5 or to untransfected L1.2 cells. No binding was detected in further staining studies using transfected L1.2 cells which expressed CCR1, CCR2, CCR3, CCR4, CCR5, CCR6, CCR7, CCR8, CCR9, hemagglutinin-tagged (Ha-) Bob, Ha-LyGpr, Ha-AJP, Ha-RDC, V28, GPR5, GPR-9-6 or Ha-Af.

Figure 10:
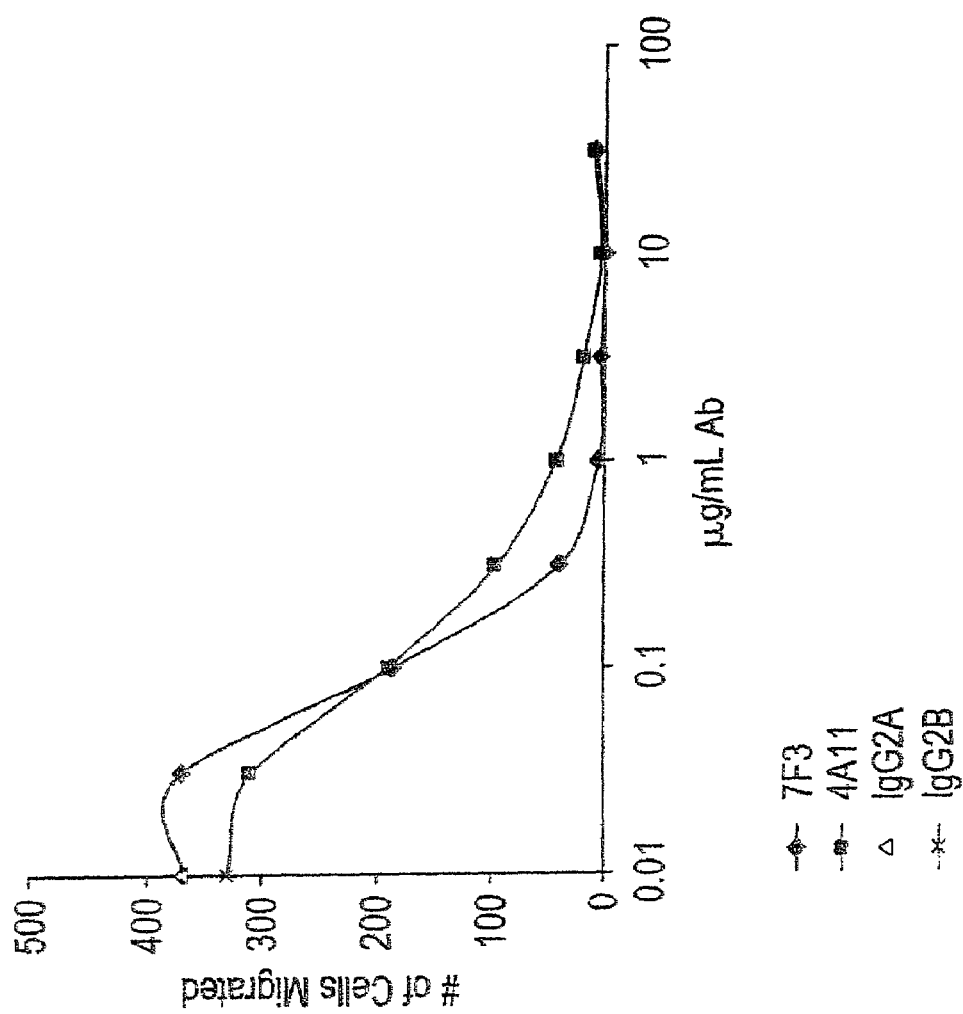
Figure 11A:
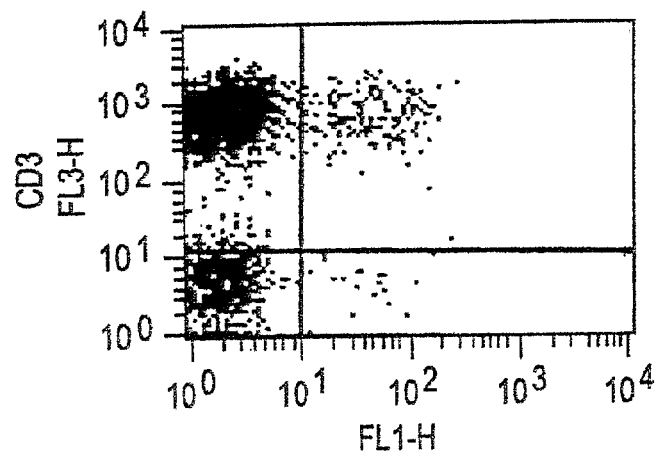
Figure 11B:
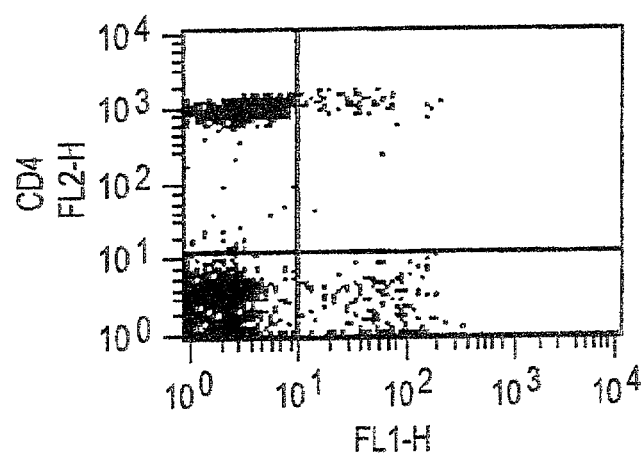
Figure 11C:
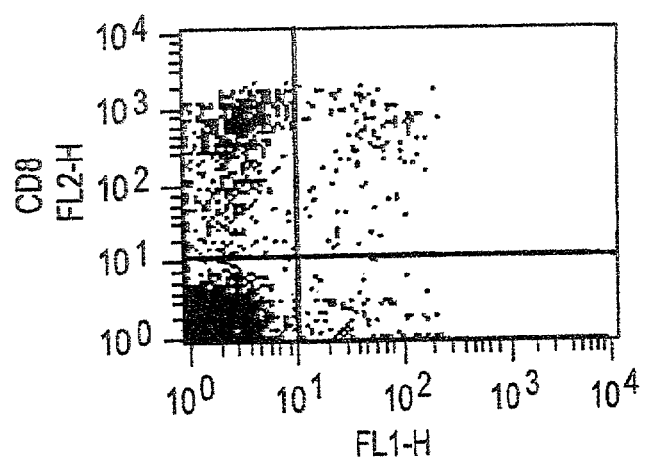
Figure 11D:
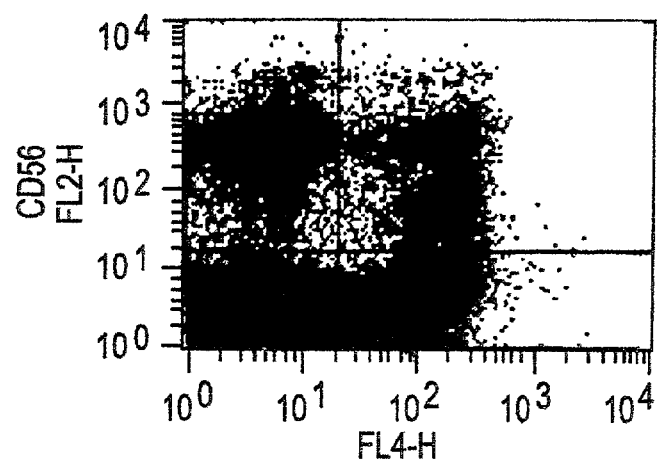
Figure 11E:
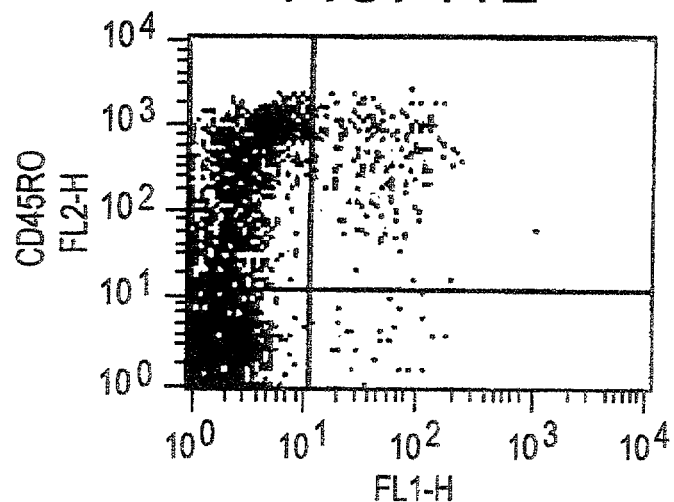
Figure 11F:
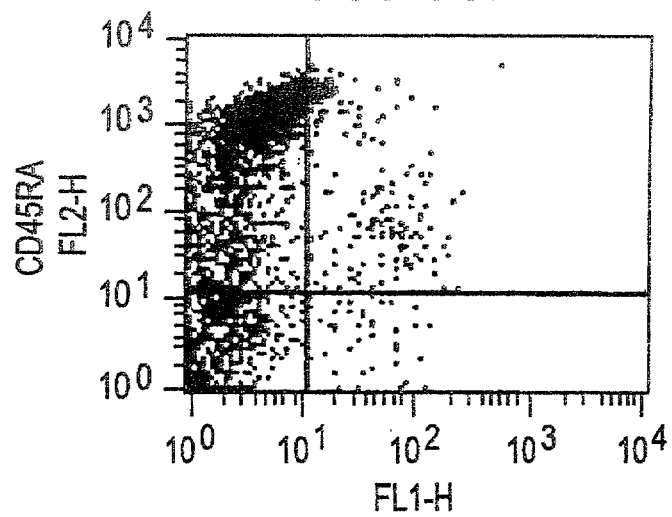
Figure 11G:
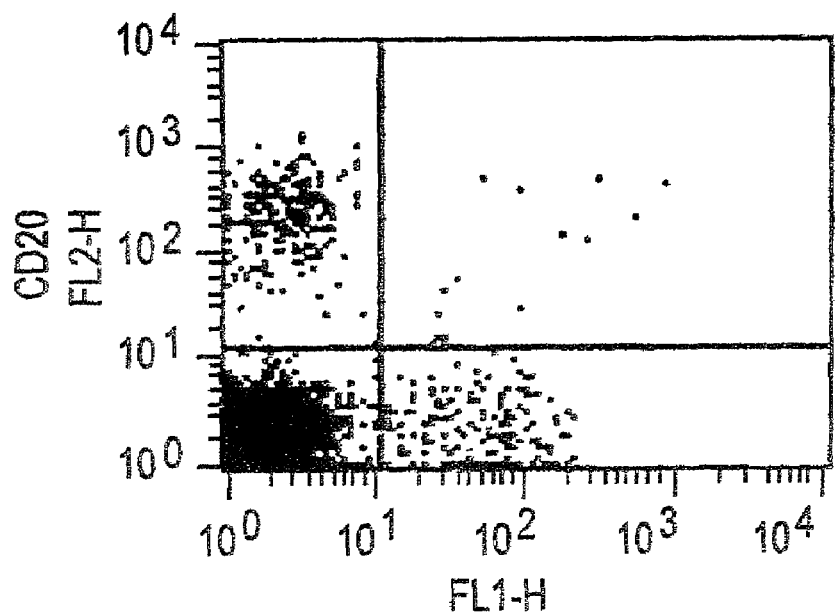
Figure 11H:
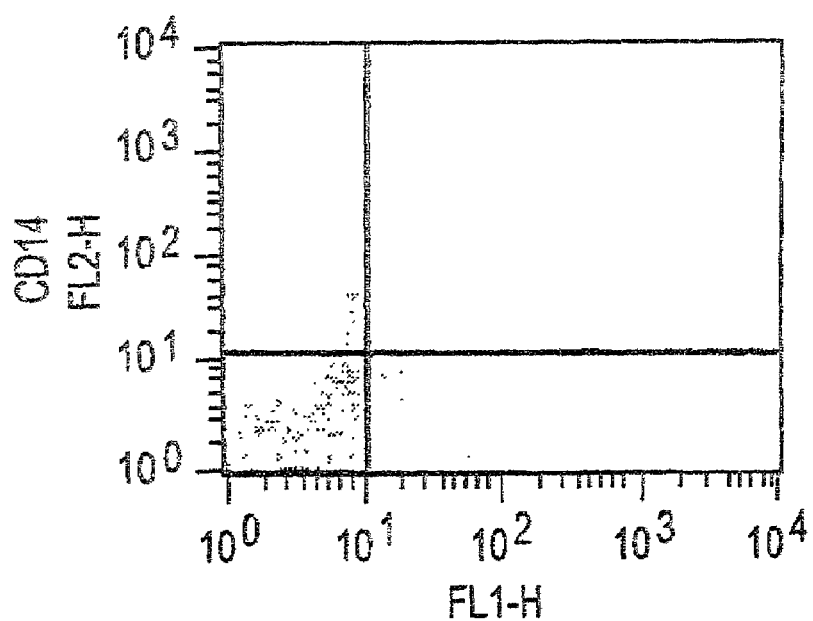
Figure 12A:
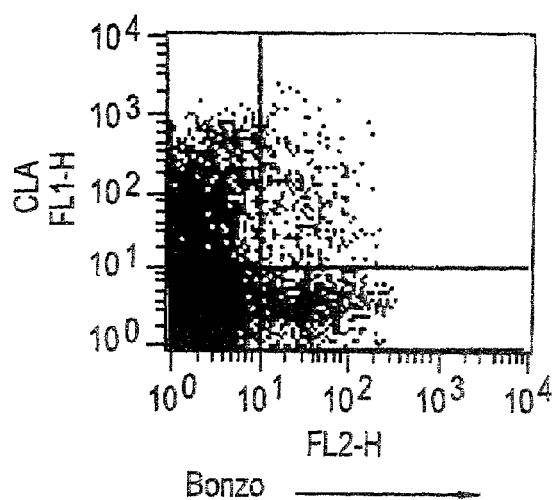
Figure 12B:
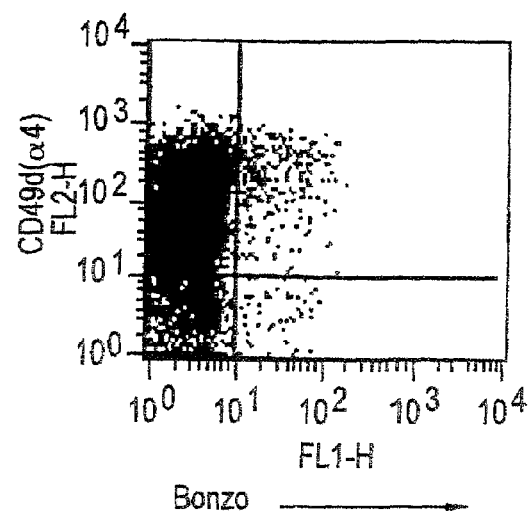
Figure 12C:
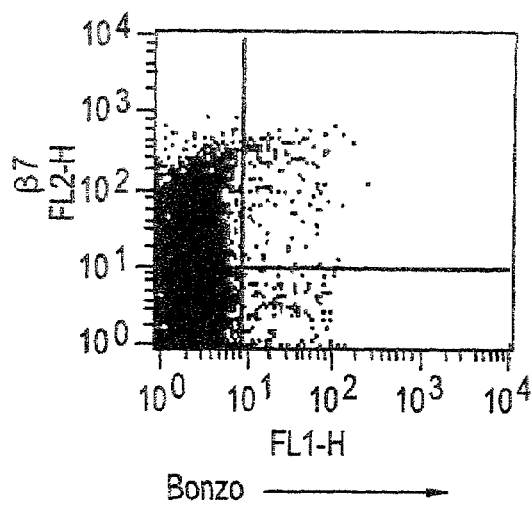
Figure 12D:
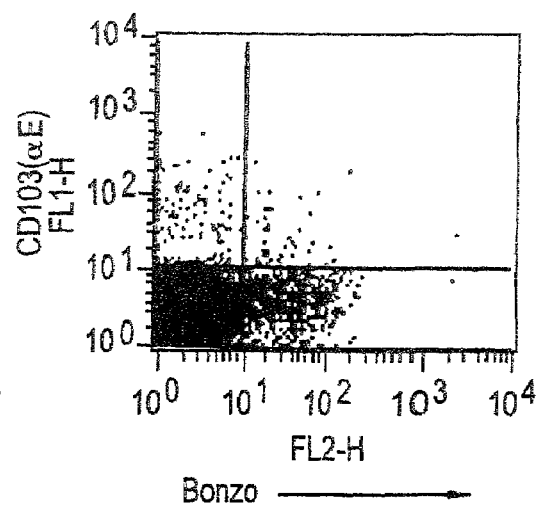
Figure 13G:
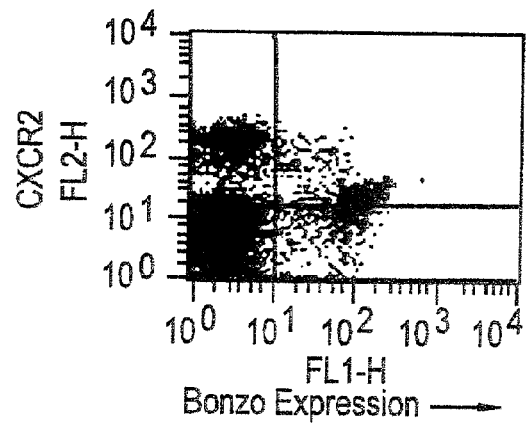
Figure 13H:
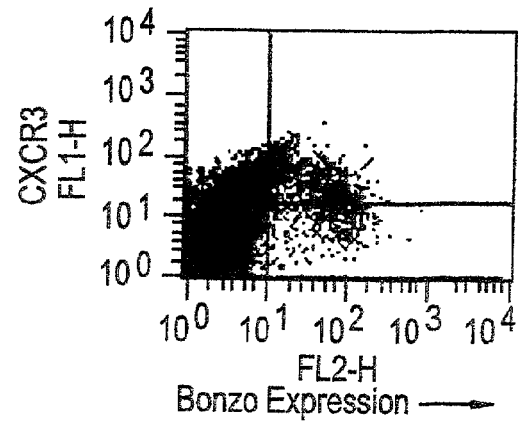
Figure 13I:
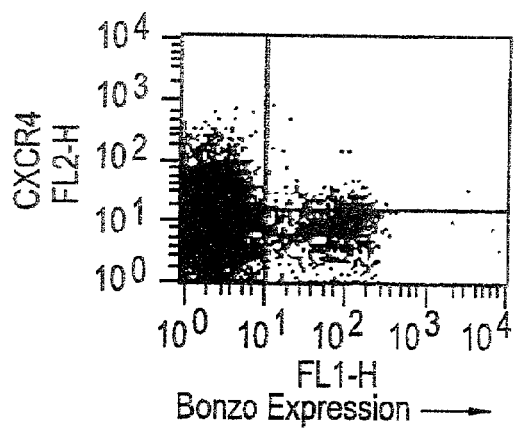
Figure 13J:
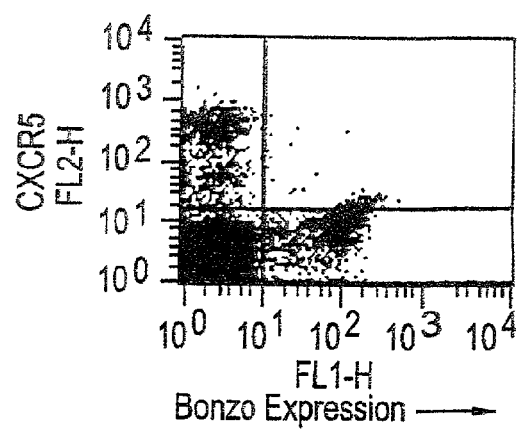

FIG. 10 is a graph showing dose dependent inhibition of SExCkine-induced chemotaxis of Bonzo/L1.2 cells by mAb 7F3 or mAb 4A11. Bonzo/L1.2 cells were incubated with concentrated supernatant from murine hybridoma 7F3 which produces mAb 7F3, from murine hybridoma 4A11 which produces mAb 4A11, or from a murine hybridoma which produces an isotype control antibody (IgG2a or IgG2b), prior to exposure to SExCkine.

FIGS. 11A–11H are fluorescence plots showing Bonzo expression on various populations of human peripheral blood mononuclear lymphocytes. Expression of Bonzo (x-axis) and lymphocyte subset markers (y-axes) CD3 (FIG. 11A), CD4 (FIG. 11B), CD8 (FIG. 11C), CD56 (FIG. 11D), CD45RO (FIG. 11E), CD45RA (FIG. 11F), CD20 (FIG. 11G) and CD14 (FIG. 11H) on human peripheral blood lymphocytes were assessed by two-color staining. Quadrants were set according to staining of isotype control mAbs (IgG2a). The data are representative of multiple donors analyzed.

FIGS. 12A–12D are fluorescence plots showing Bonzo expression on subsets of human peripheral blood CD4+ T lymphocytes. Expression of Bonzo (x-axis) and lymphocyte subset markers (y-axes) CLA (FIG. 12A), CD49d (α4 integrin, FIG. 12B), β7 integrin (FIG. 12C) and CD103 (αE integrin, FIG. 12D) on human peripheral blood CD4+ T lymphocytes were assessed by three-color staining, gating on CD4+ cells. Quadrants were set according to staining of isotype control mAbs (IgG2a). The data are representative of multiple donors analyzed.

FIGS. 13A–13J are fluorescence plots showing co-expression of Bonzo and other CC or CXC chemokine receptors on human peripheral blood lymphocytes. Expression of Bonzo (x-axis) and CC or CXC chemokine receptors (y-axes) CCR1 (FIG. 13A), CC. (FIG. 13B), CCR3 (FIG. 13C), CCR5 (FIG. 13D)), CCR6 (FIG. 13E)), CXCR1 (FIG. 13F), CXCR (FIG. 13G), CXCR3 (FIG. 13H), CXCR4 (FIG. 13I) and CXCR5 (FIG. 13J) on human peripheral blood lymphocytes were assessed by two-color staining. Quadrants were set according to staining of isotype control mAbs (IgG2a). The data are representative of multiple donors analyzed.

Figure 14A:
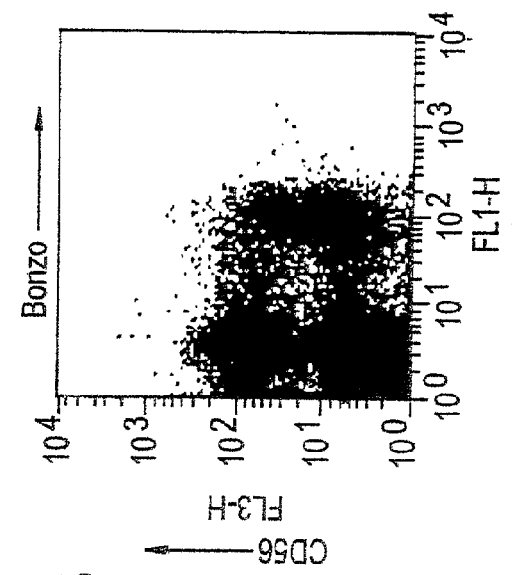
Figure 14B:
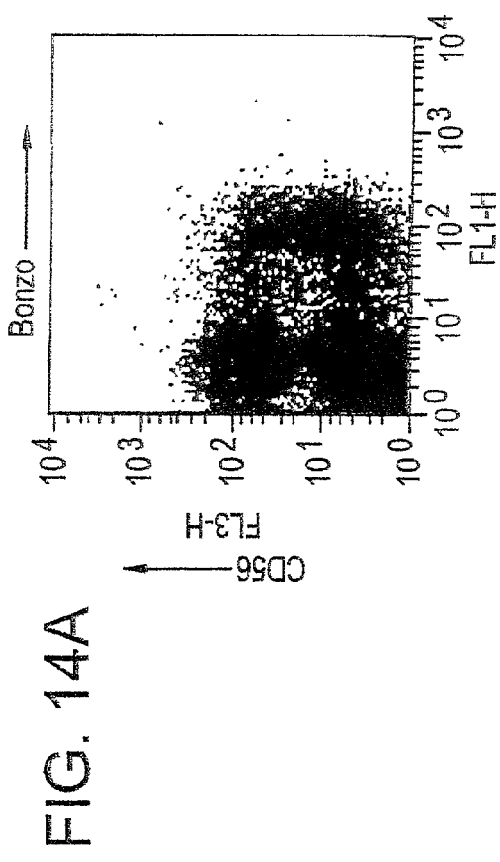
Figure 14E:
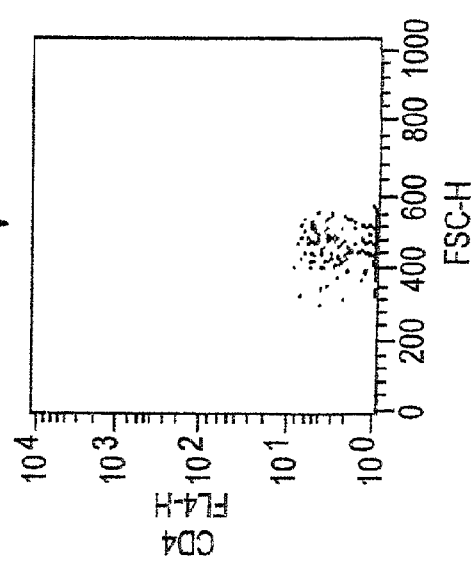
Figure 14F:
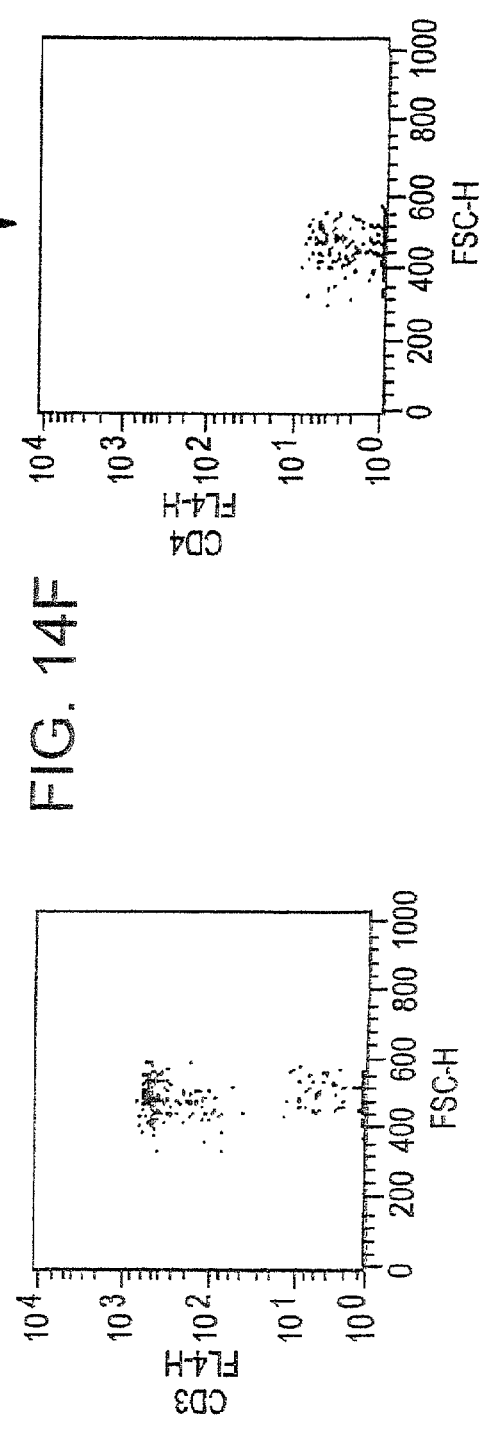
Figure 14C:
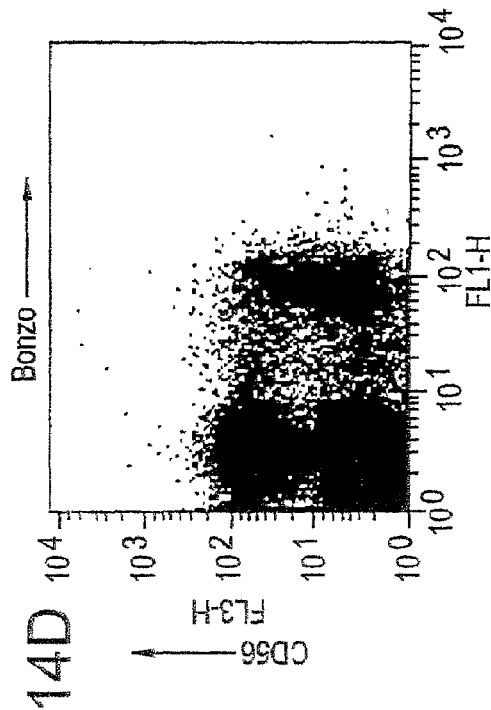
Figure 14D:
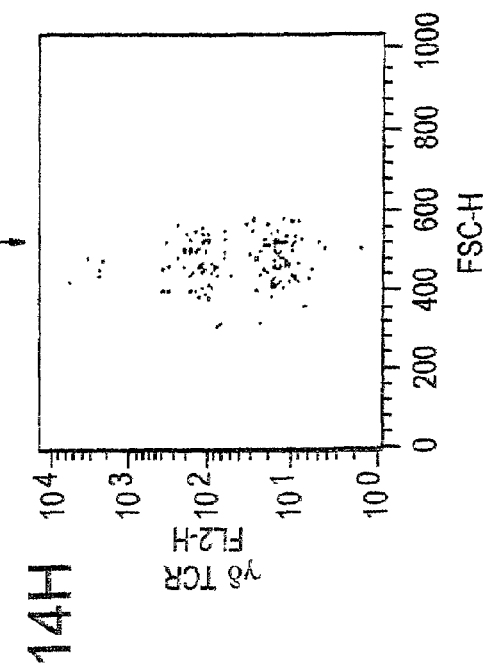
Figure 14G:
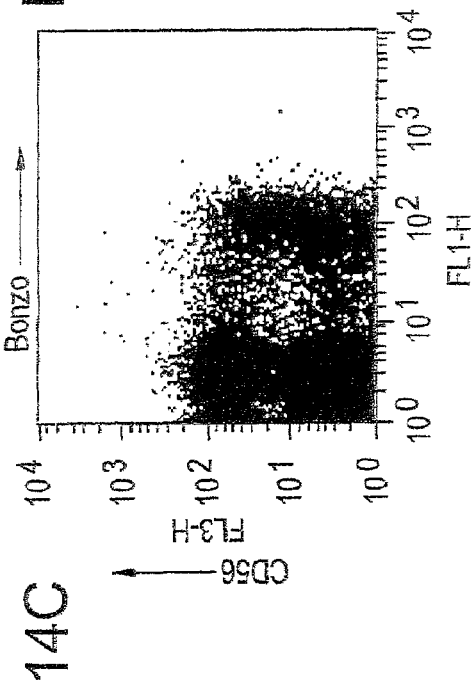
Figure 14H:
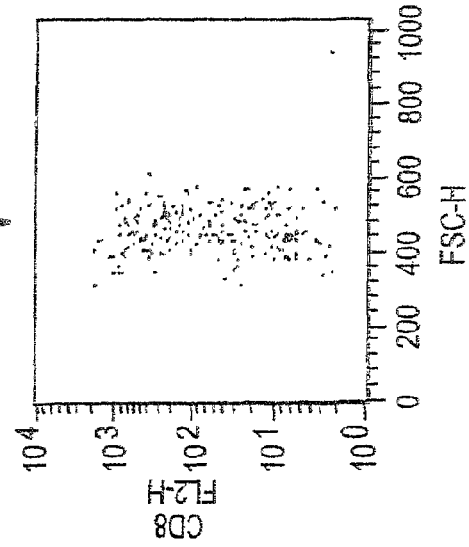
Figure 16A:
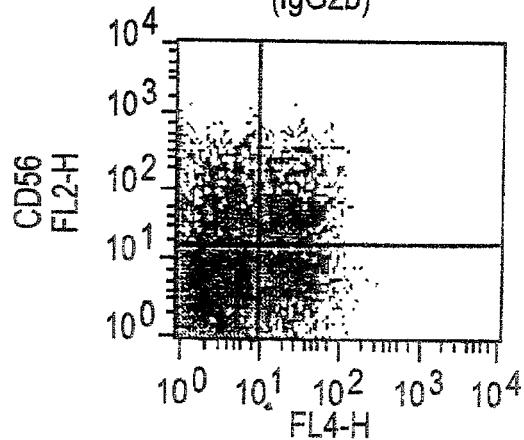
Figure 16B:
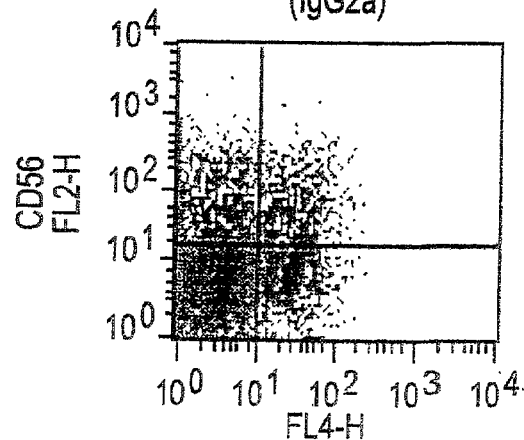
Figure 16C:
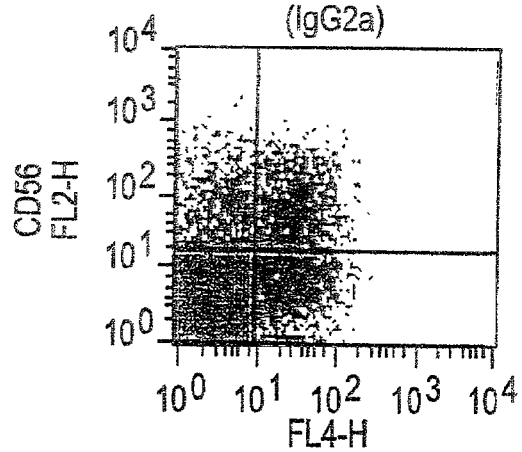
Figure 16D:
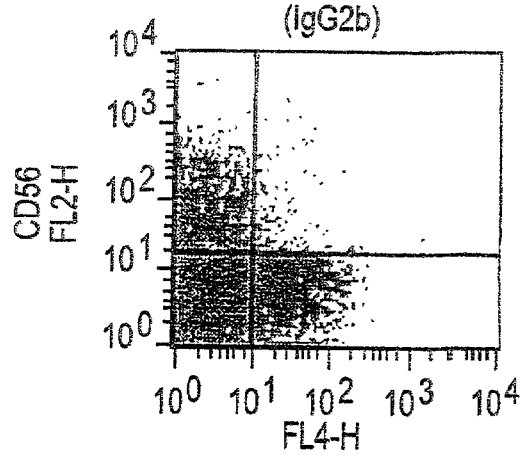

FIGS. 14A–14H are fluorescence plots showing expression of lymphocyte subset markers on Bonzo+CD56+ lymphocytes. Expression was analyzed in a three color study gating on Bonzo+CD56+ cells (FIGS. 14A–14D). The gated cells were analyzed for expression of CD3 (FIG. 14E), CD4 (FIG. 14F), CD8 (FIG. 14G) or γδ T cell receptor (TCR) (FIG. 14H).

FIGS. 15A–15C are fluorescence plots showing Bonzo expression on CD3+CD56+ and on CD8+CD56+ human cytotoxic effector cells from peripheral blood. Expression of Bonzo and CD56, CD3 and CD8 was analyzed in a four-color study, gating on CD56+ cells. FIG. 15A is a fluorescence plot showing the population of CD56+ which were gated on. The gated CD56+ cells were analyzed for the expression of Bonzo (x-axis) and CD3 (y-axis, FIG. 15B) or CD8 (y-axis, FIG. 15C). Quadrants were set according to staining of isotype control mAbs (IgG2a). The data are representative of multiple donors analyzed.

FIGS. 16A–16D are fluorescence plots showing Bonzo expression on CD8$^{hi}$, CD45RA$^{lo}$, CD56+ human peripheral blood T cells. Expression was analyzed in a four-color study gating on CD8$^{hi}$CD 45RA$^{lo}$ cells. The gated cells were analyzed for expression of CD56 (y-axis) and Bonzo (x-axis) using mAb 4A11 (FIG. 16A), mAb 7F3 (FIG. 16B) and mAb 7A2 (FIG. 16C). mAb 7H12 which binds CCR7 served as a negative control.

Figure 17A:
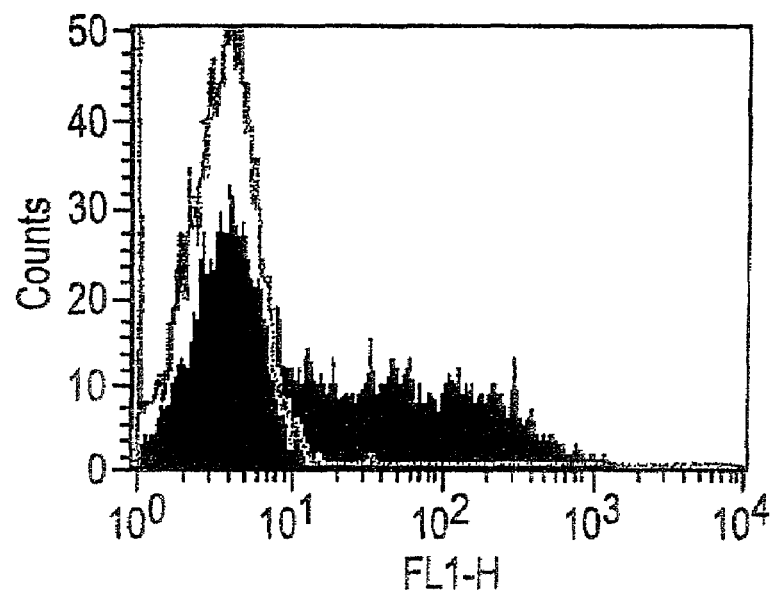
Figure 17B:
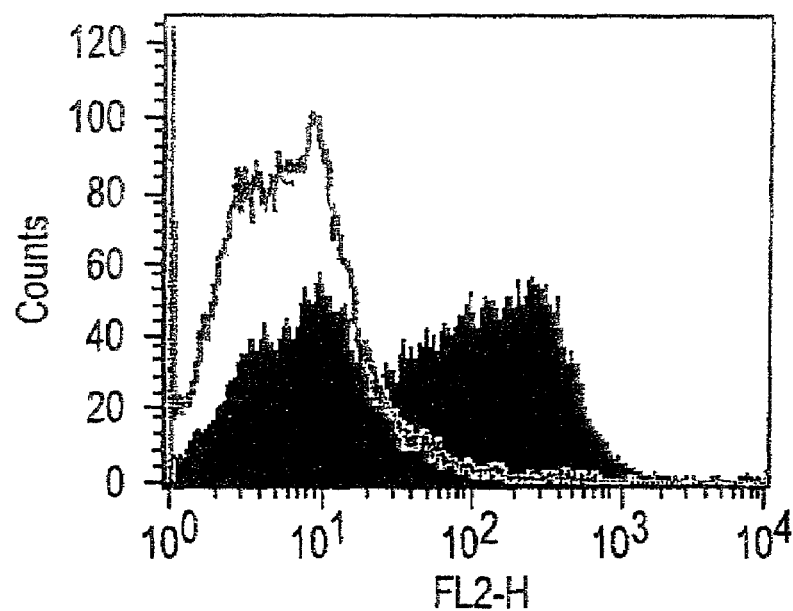

FIGS. 17A and 17B are fluorescence histograms showing that Bonzo is expressed on activated T cell (CD3 blasts, FIG. 17A) and NK cells (LAK cells, FIG. 17B). Bonzo expression was detected by staining with hybridoma culture supernatant containing mAb 7F3. The CD3 Blasts were maintained in IL2 for 9 days prior to staining. The LAK cells were activated with IL12 for 6 days.

Figure 18:
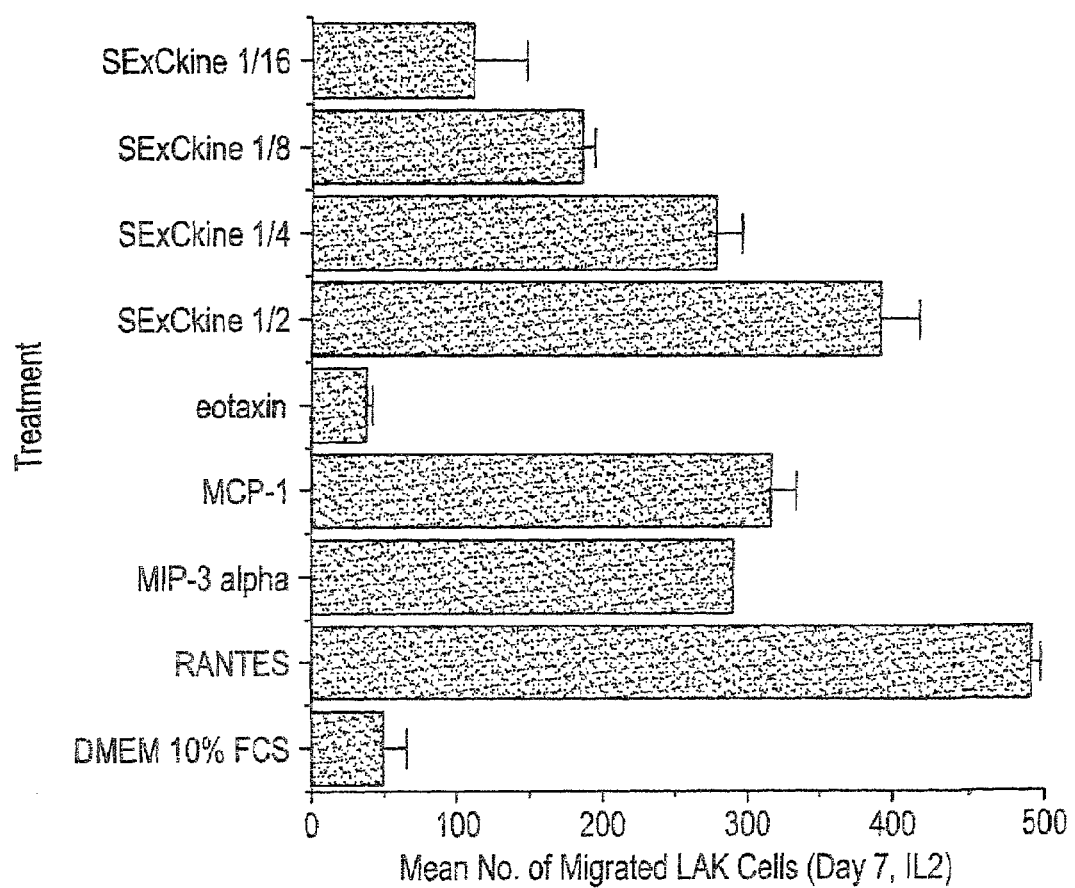

FIG. 18 is a histogram showing that chemotaxis of lymphokine activated killer cells (LAK) was induced by SExCkine. Chemotaxis of LAK cells was also induced by RANTES, MIP-3 alpha and MCP-1. However, eotaxin did not induce chemotaxis of LAK cells, and no migration was seen in assays that did not contain chemokine.

FIGS. 19A–19D are fluorescence plots showing up-regulation of Bonzo expression on in vitro derived cytokine-induced killer (CIK) cells. Cells were removed from in vitro CIK cultures at day 1 (FIGS. 19A and 19C) and day 21 (FIGS. 19B and 19D) and analyzed for expression of Bonzo in a three-color study, gating of CD3+CD56+ cells. FIGS. 19A and 19B are fluorescence plots showing the gated CD3+CD56+ cells. FIGS. 19C and 19D are fluorescence plots showing the expression of Bonzo on the gated cells. Bonzo expression was detected by staining with hybridoma culture supernatant containing mAb 7F3.

Figure 20:
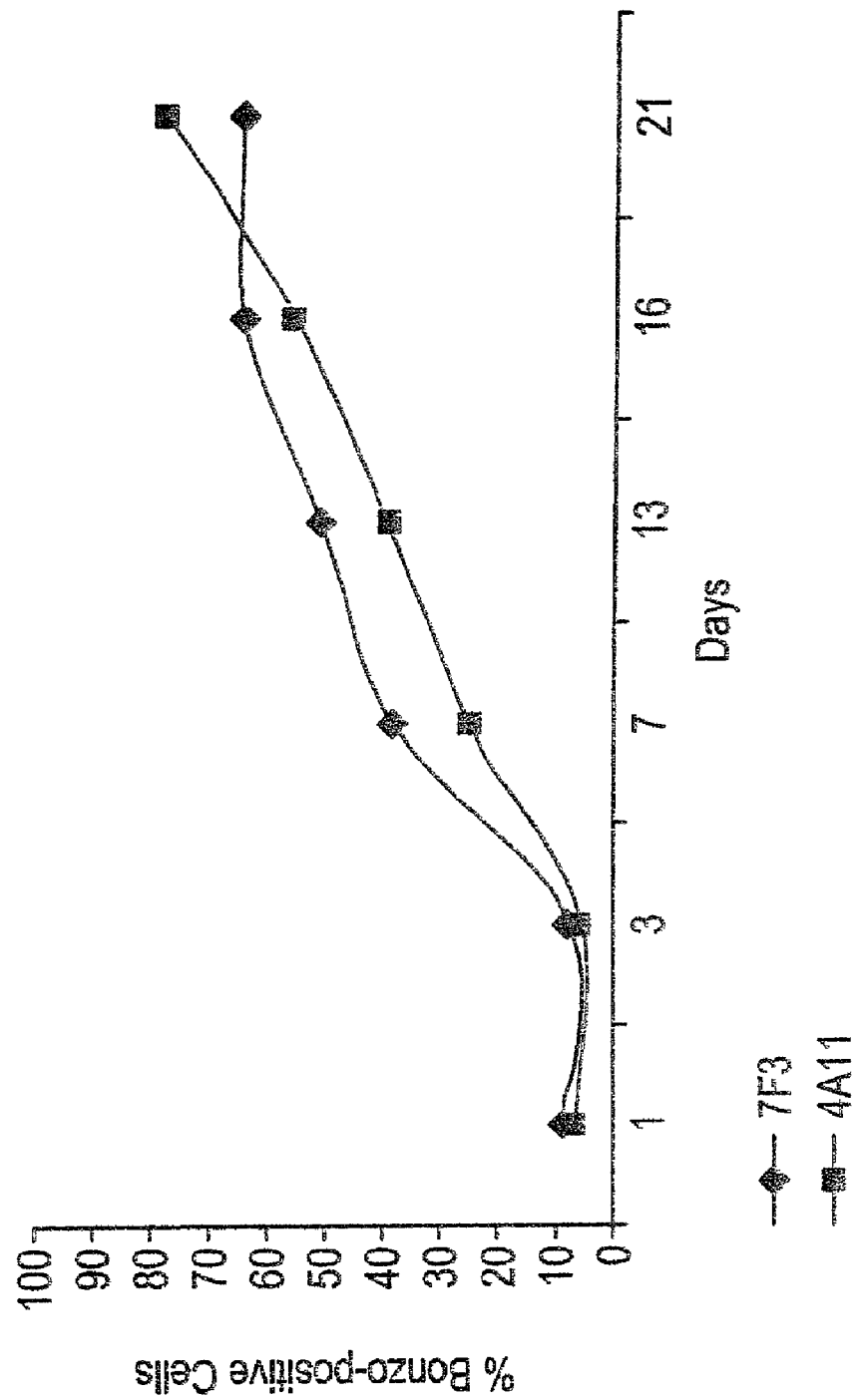

FIG. 20 is a graph showing that expression of Bonzo on in vitro derived CIK cells increases over time. At selected time points, cells were analyzed for expression of Bonzo by staining with mAb 7F3 or mAb 4A11.

Figure 21:
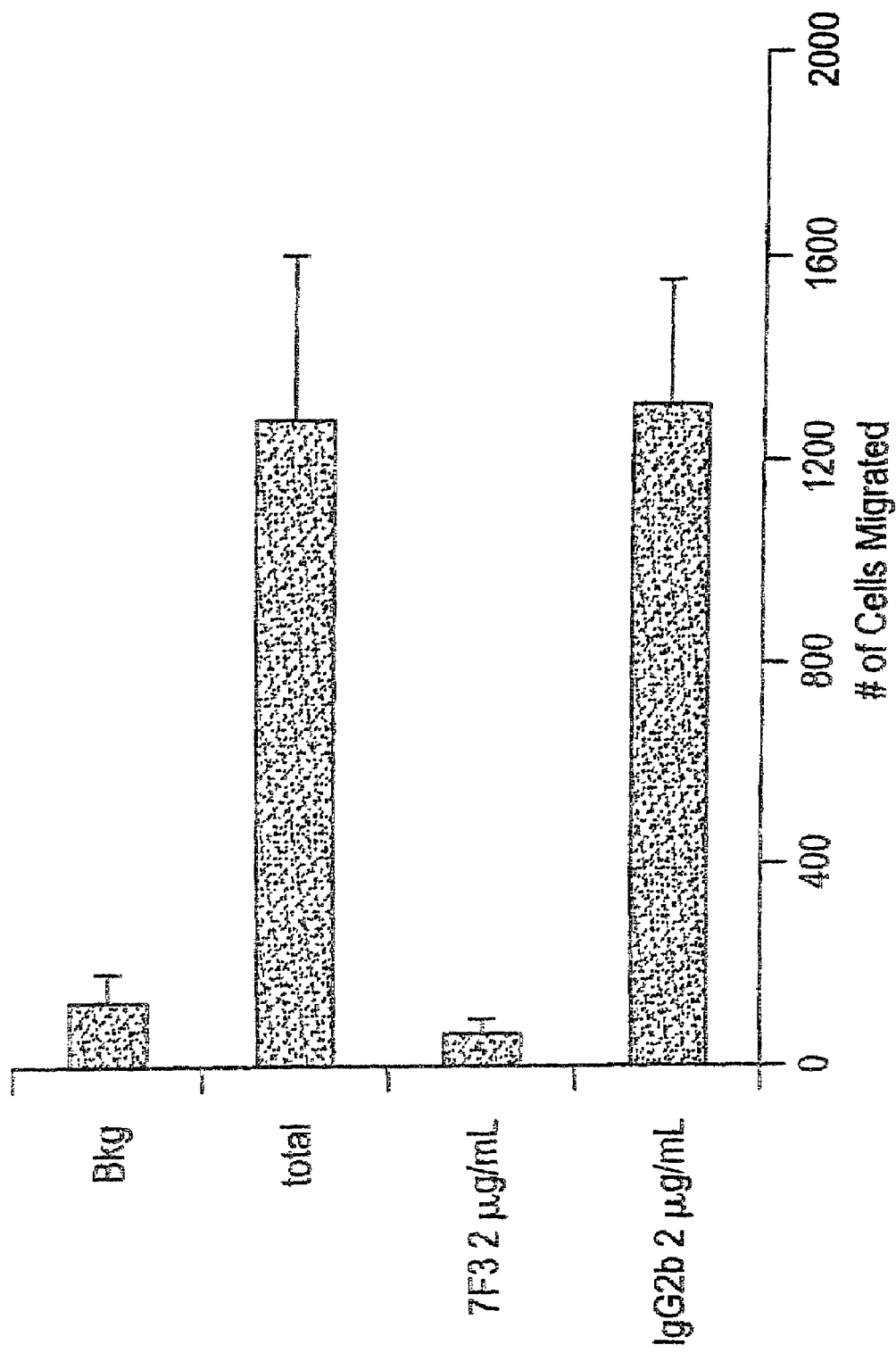

FIG. 21 is a graph showing that SExCkine-induced chemotaxis of CIK cells can be inhibited by mAb 7F3, but is not significantly inhibited by irrelevant control IgG2b. The in vitro derived CIK cells used in the assay were prepared by 17 days of culture. Chemotaxis was measured in control wells that contained no SExCkine (Bkg) and control wells that contained culture supernatant of 293T cells transiently transfected with SExCkine (total). Antibody inhibition was assessed by incubating CIK cells with mAb 7F3 (2 µg/mL) or isotype control mAb IgG2b (2 µg/mL) for 20 minutes at 37° C. prior to exposure to SExCkine.

Figure 22:
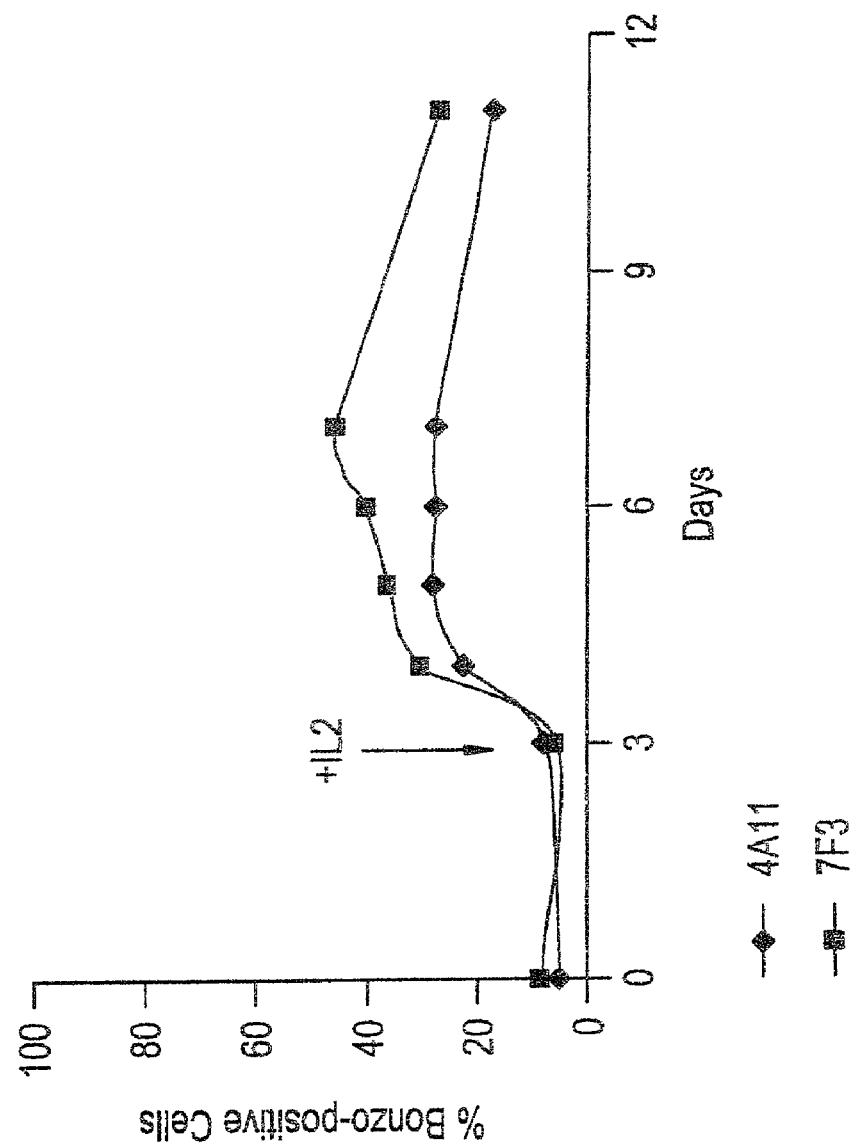

FIG. 22 is a graph showing the time course of activation-induced expression of Bonzo on activated human peripheral blood T cells. Human peripheral blood cells were activated by culture with immobilized anti-CD3 (OKT3, 5 µg/mL), on day three interleukin 2 (IL-2, 100 U/mL) was added to the cultures. Expression of Bonzo was assessed at selected times by staining with mAb 4A11 or mAb 7F3.

Figure 23B:
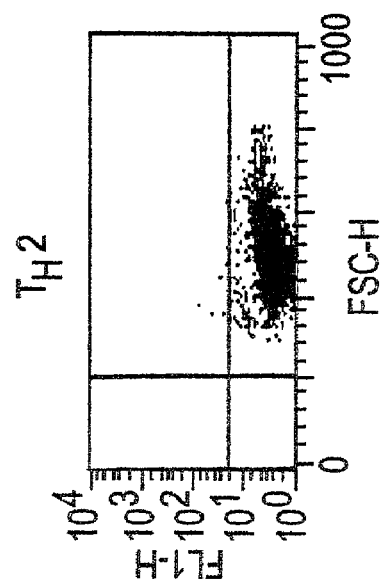
Figure 23D:
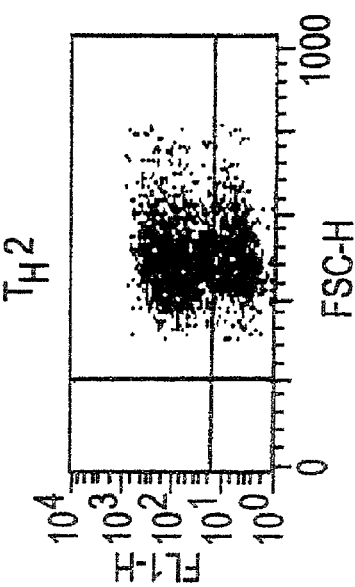
Figure 23A:
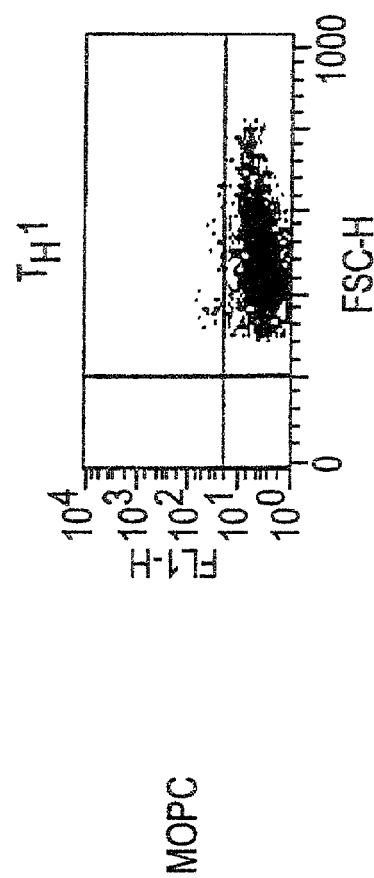
Figure 23C:
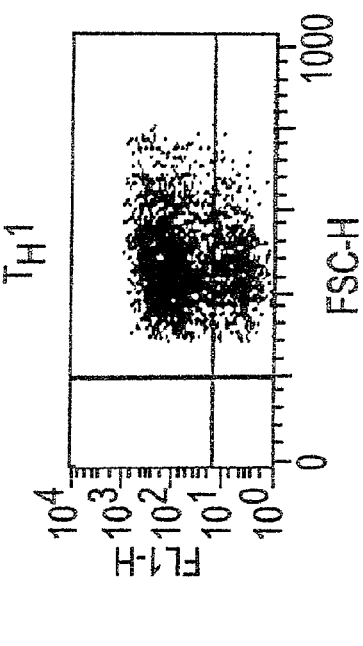
Figure 23E:
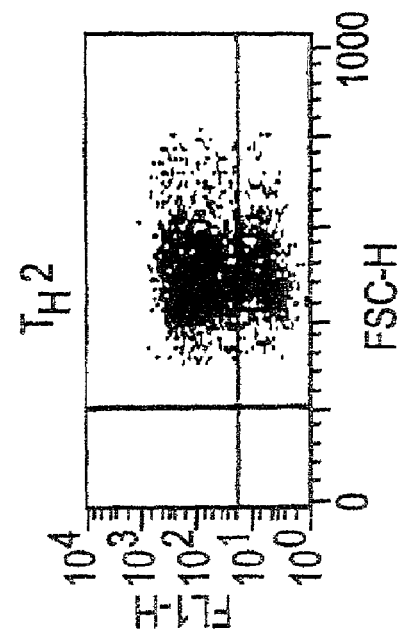
Figure 23F:
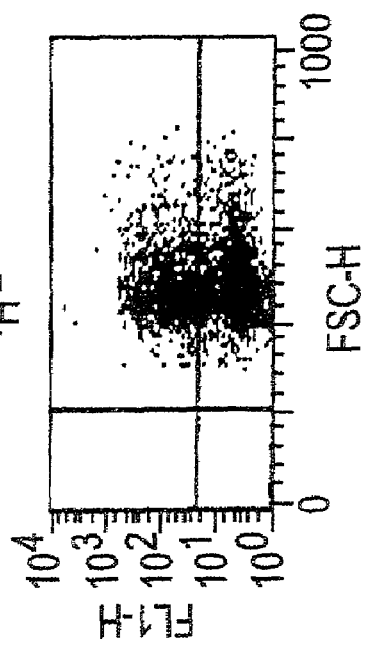
Figure 23G:
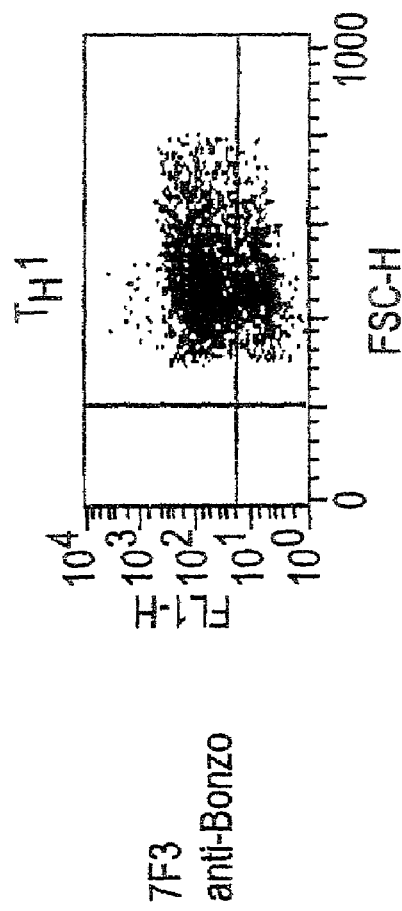
Figure 23H:
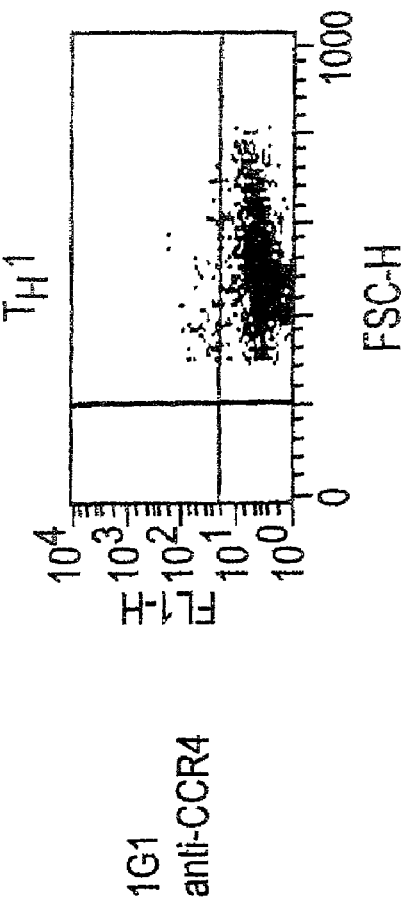
Figure 24A:
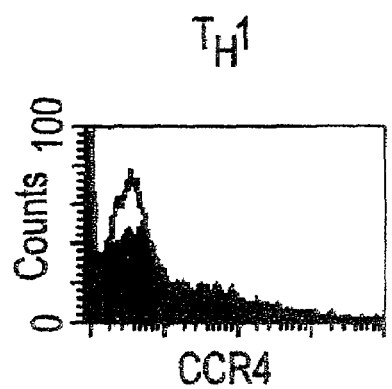
Figure 24D:
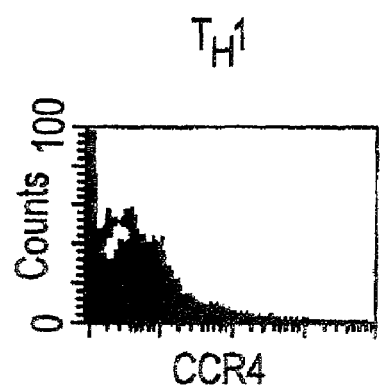
Figure 24B:
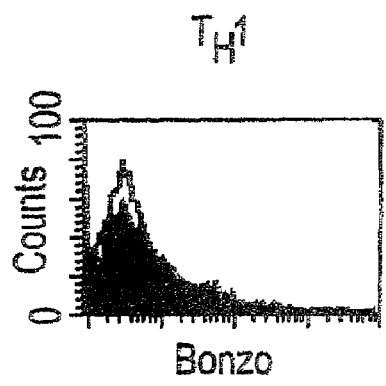
Figure 24E:
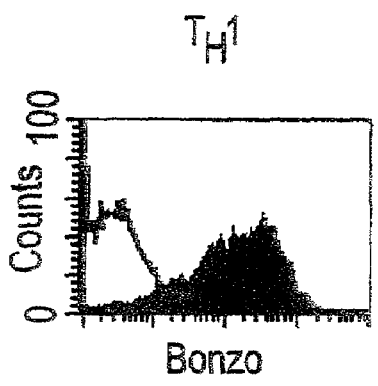
Figure 24C:
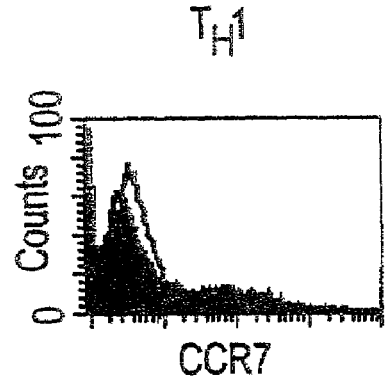
Figure 24F:
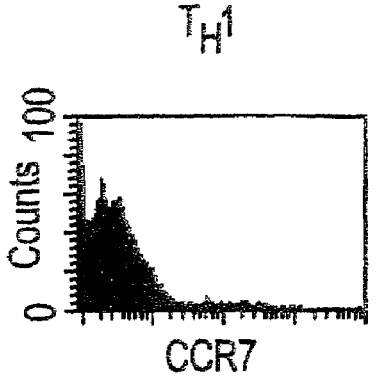

FIGS. 23A–23H are fluorescence plots showing Bonzo expression on in vitro derived TH1 and TH2 cells. Chronically activated TH1 and TH2 cells were generated from human CD4$^+$ umbilical vein lymphocytes by two cycles of in vitro activation with appropriate cytokines. The cells were analyzed by staining with isotype control mAb MOPC (IgG2b) (FIGS. 23A and 23B), mAb 4A11 (FIGS. 23C and 23D), mAb 7F3 (FIGS. 23E and 23F) or mAb 1G1, which binds the TH2 subset marker CCR4 (FIGS. 23G and 23H).

FIGS. 24A–24F are fluorescence histograms showing that Bonzo expression is augmented by repeated activation of in vitro derived TH1 cells. Cells which had been stimulated by one round of activation (FIGS. 24A–24C) or two rounds of activation (FIGS. 24D–24F) were stained with anti-Bonzo mAb 7F3 (FIGS. 24B and 24E), anti-CCR4 mAb mAb 1G1 (FIGS. 24A and 24D) or anti-CCR7 mAb 7H12 FIGS. 24C and 24F). TH1 cells expressed increased amounts of Bonzo after repeated activation (compare FIGS. 24B and 24E).

Figure 25A:
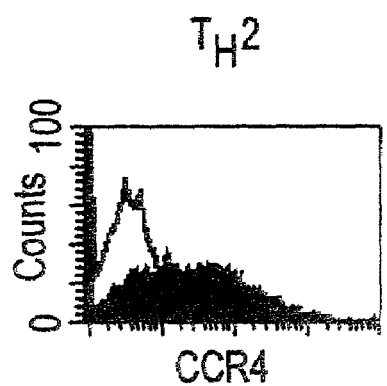
Figure 25D:
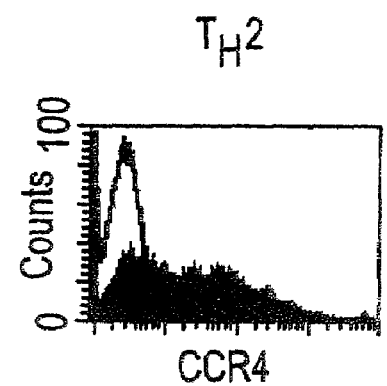
Figure 25B:
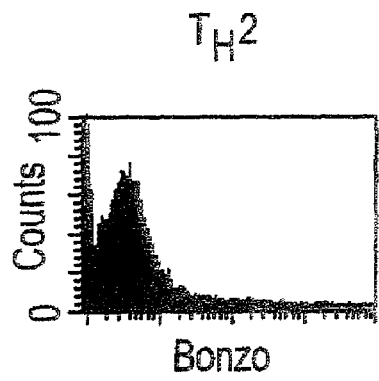
Figure 25E:
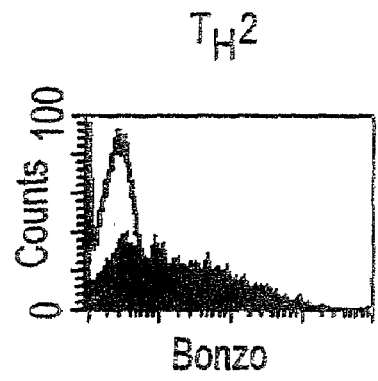
Figure 25C:
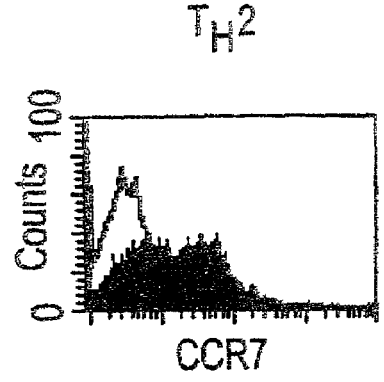
Figure 25F:
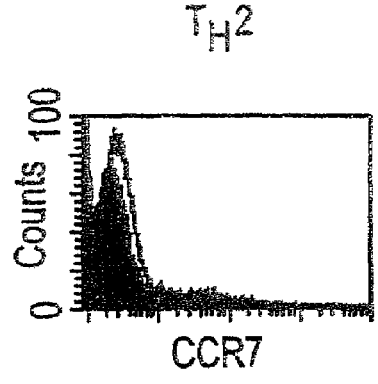

FIGS. 25A–25F are fluorescence histograms showing that Bonzo expression is augmented by repeated activation of in vitro derived TH2 cells. Cells which had been stimulated by one round of activation (FIGS. 25A–25C) or two rounds of activation (FIGS. 25D–25F) were stained with anti-Bonzo mAb 7F3 (FIGS. 25B and 25E), anti-CCR4 mAb mAb 1G1 (FIGS. 25A and 25D) or anti-CCR7 mAb 7H12 (FIGS. 25C and 25F). TH2 cells expressed increased amounts of Bonzo after repeated activation (compare FIGS. 25B and 25E).

Figure 26A:
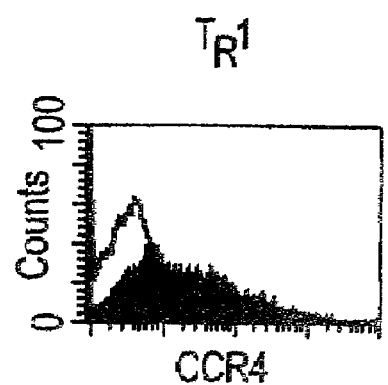
Figure 26D:
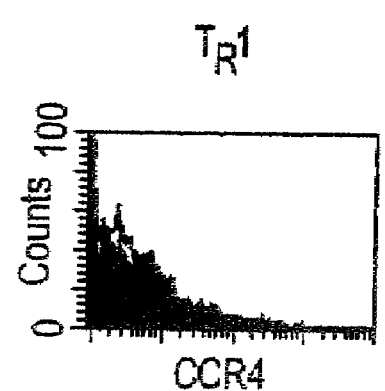
Figure 26B:
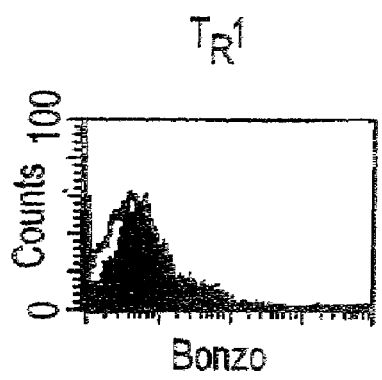
Figure 26E:
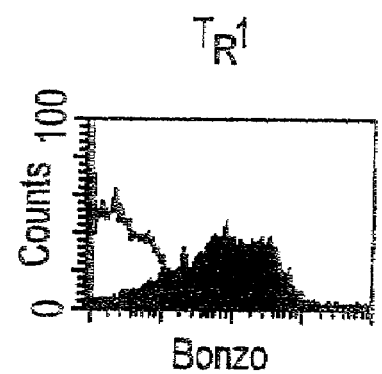
Figure 26C:
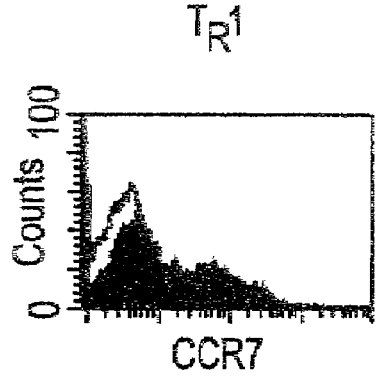
Figure 26F:
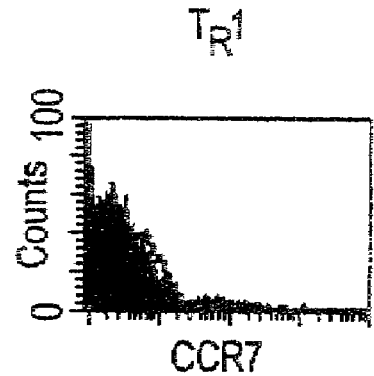

FIGS. 26A–26F are fluorescence histograms showing that Bonzo expression is augmented by repeated activation of in vitro derived TR1 cells. Cells which had been stimulated by one round of activation (FIGS. 26A–26C) or two rounds of activation (FIGS. 26D–26F) were stained with anti-Bonzo mAb 7F3 (FIGS. 26B and 26E), anti-CCR4 mAb mAb 1G1 (FIGS. 26A and 26D) or anti-CCR7 mAb 7H12 (FIGS. 26C and 26F). TR1 cells expressed increased amounts of Bonzo after repeated activation (compare FIGS. 26B and 26E).

Figure 27:
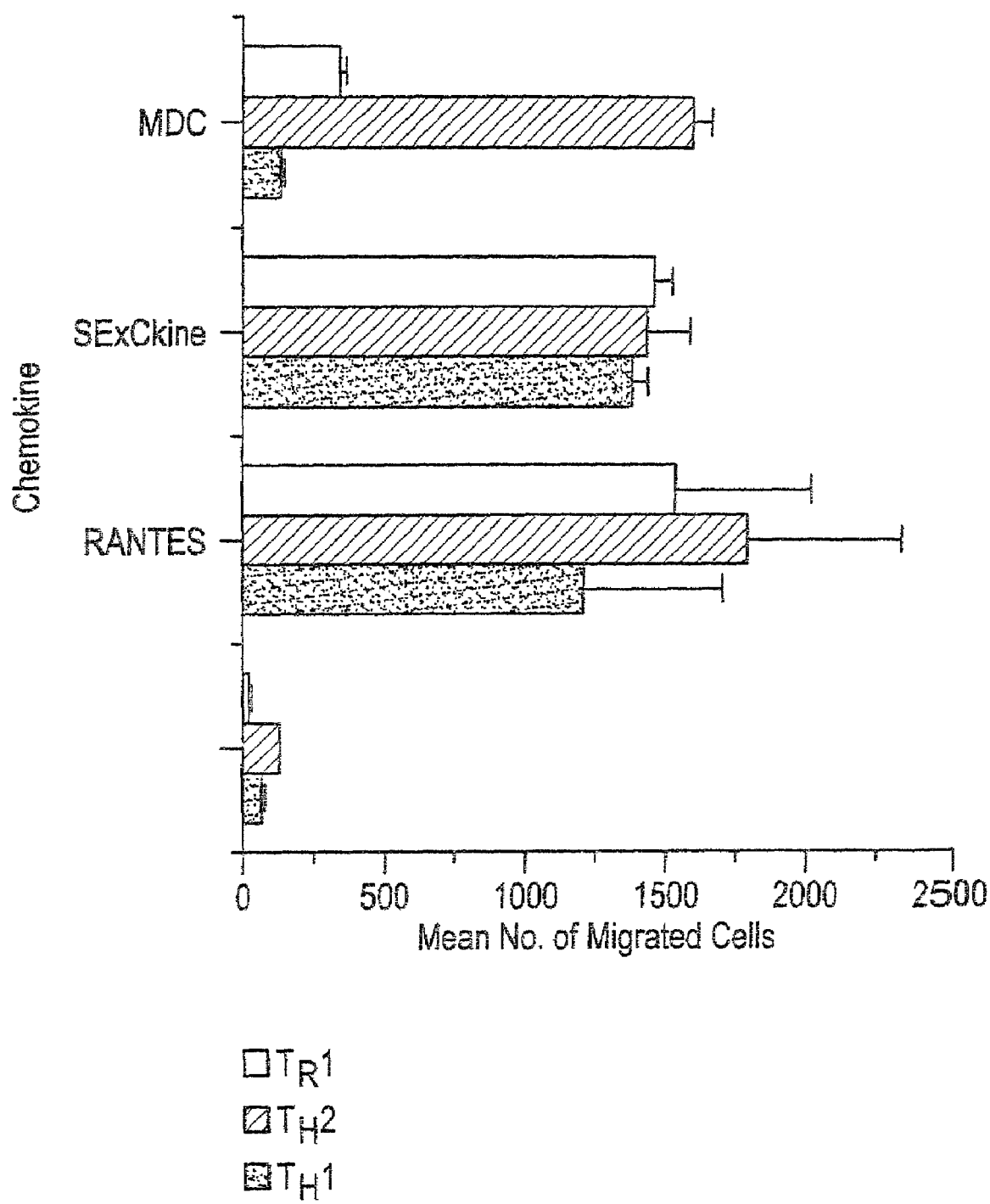

FIG. 27 is a histogram showing that chemotaxis of in vitro derived TH1, TH2 and TR1 cells was induced by SExCkine. Chemotaxis of the TH1, TH2 and TR1 cells was also induced by RANTES. However, only TH2 cells migrated significantly in cultures containing MDC. No chemotaxis was observed in cultures that did not contain chemokine (−).

Figure 28:
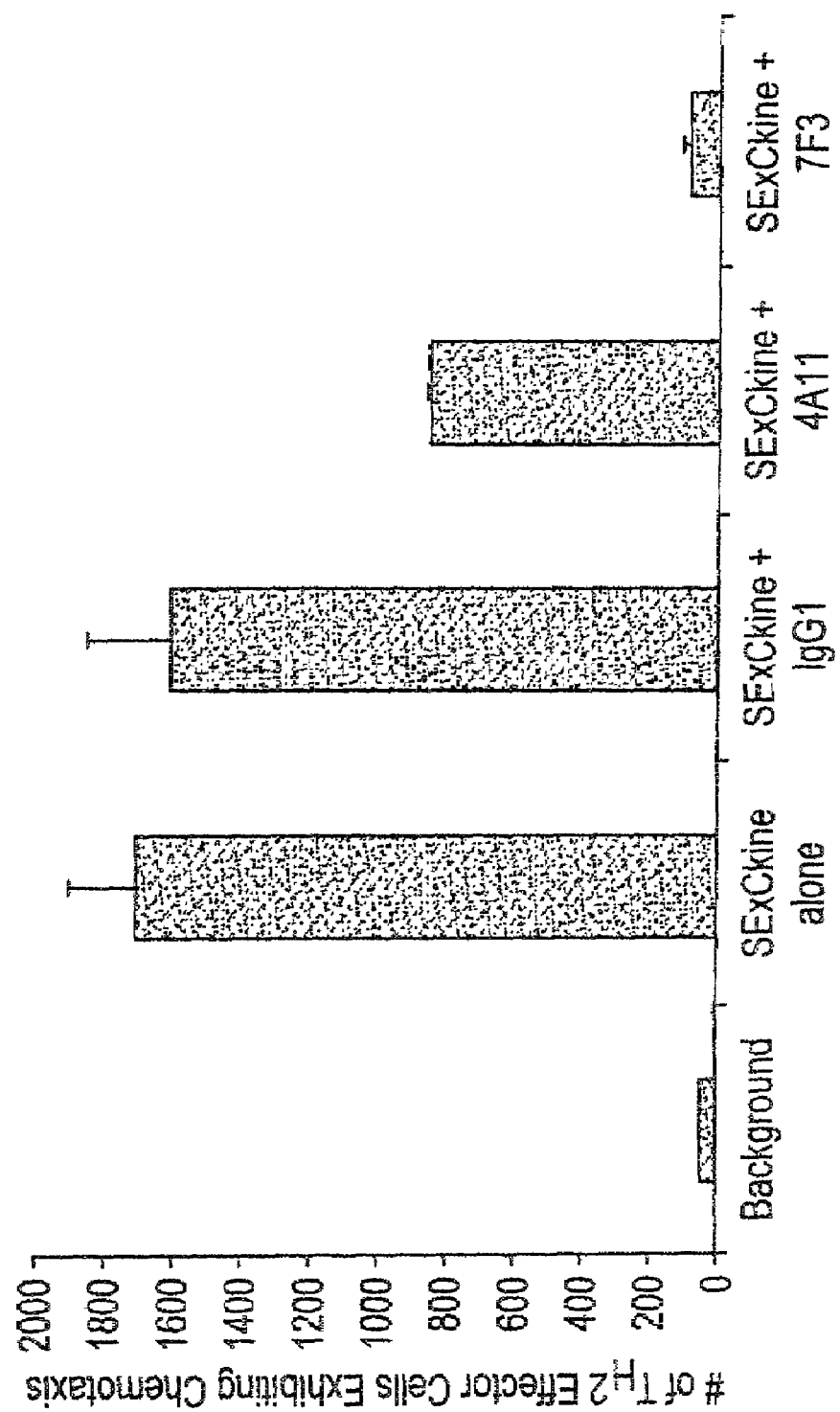

FIG. 28 is a histogram showing that SExCkine-induced chemotaxis of TH2 cells was inhibited by mAb 7F3 or mAb 4A11. TH2 cells were incubated with concentrated supernatant from murine hybridoma 7F3 which produces mAb 7F3, from murine hybridoma 4A11 which produces mAb 4A11, or from a murine hybridoma which produces an isotype control antibody (IgG1), prior to exposure to SExCkine. Background is the number of cells that migrated in wells containing assay media without chemokine.

Figure 29:
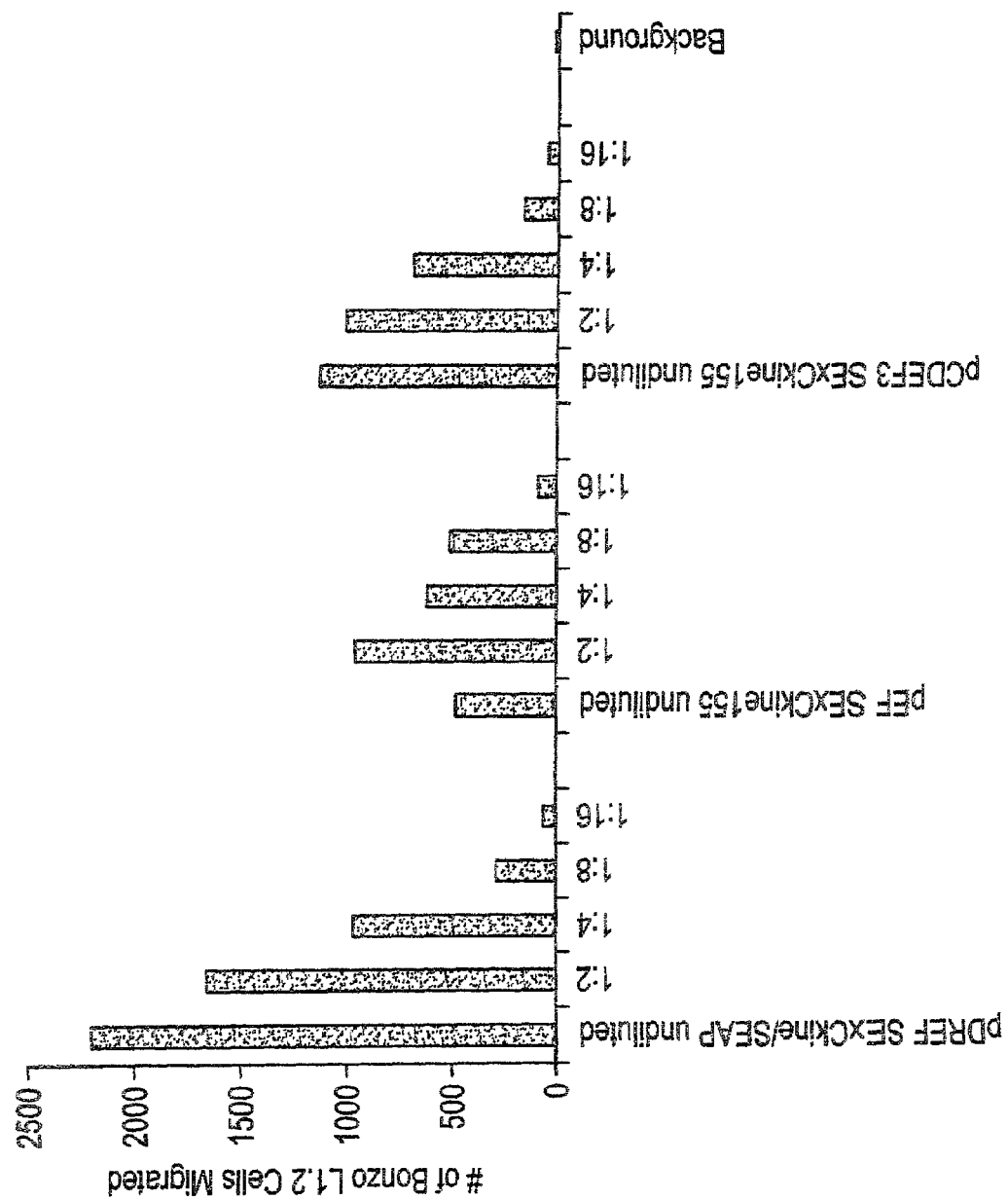

FIG. 29 is a histogram showing that chemotaxis of Bonzo/L1.2 cells is induced by amino-terminal fragments of human SExCkine. Chemotaxis was assessed in assays using Bonzo/L1.2 cells and conditioned culture supernatant from 293T cells transiently transfected with an expression vector encoding residues 1–199 of human SExCkine (SEQ ID NO:4) fused to human alkaline phosphatase (pDREF SExCkine/SEAP) or with a nucleic acid encoding residues 1–155 of human SExCkine (SEQ ID NO:4) cloned into expression vector pEF or pCDEF3. Bonzo/L1.2 cells were assayed for chemotactic response to undiluted culture supernatants of transiently transfected 293T cells or to various dilutions of the supernatants (1:2, 1:4, 1:8 and 1:16). Background migration was determined in cultures which contained assay media without chemokine.

Figure 30:
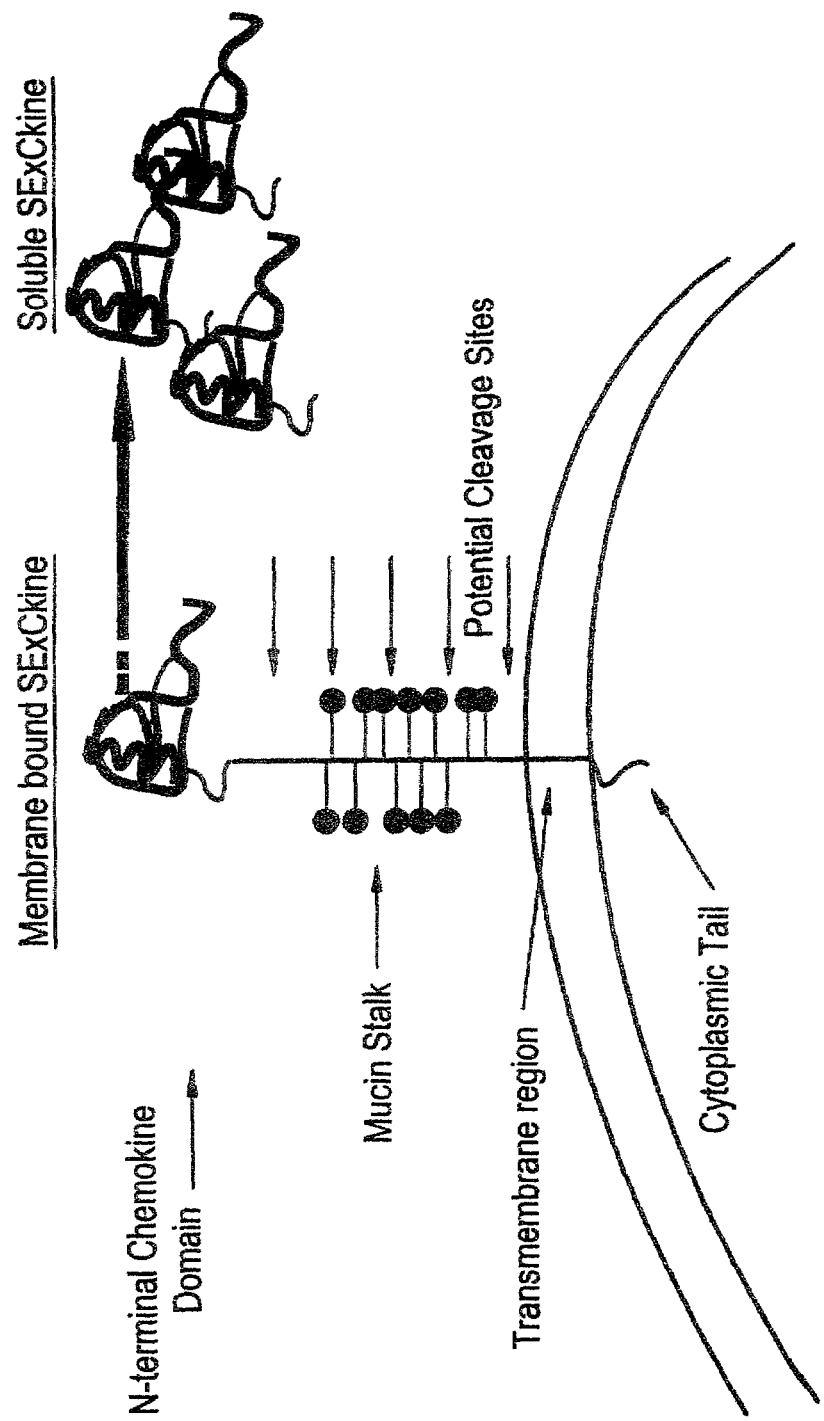

FIG. 30 illustrates the predicted structure of the transmembrane form of human SExCkine.

Figure 31:
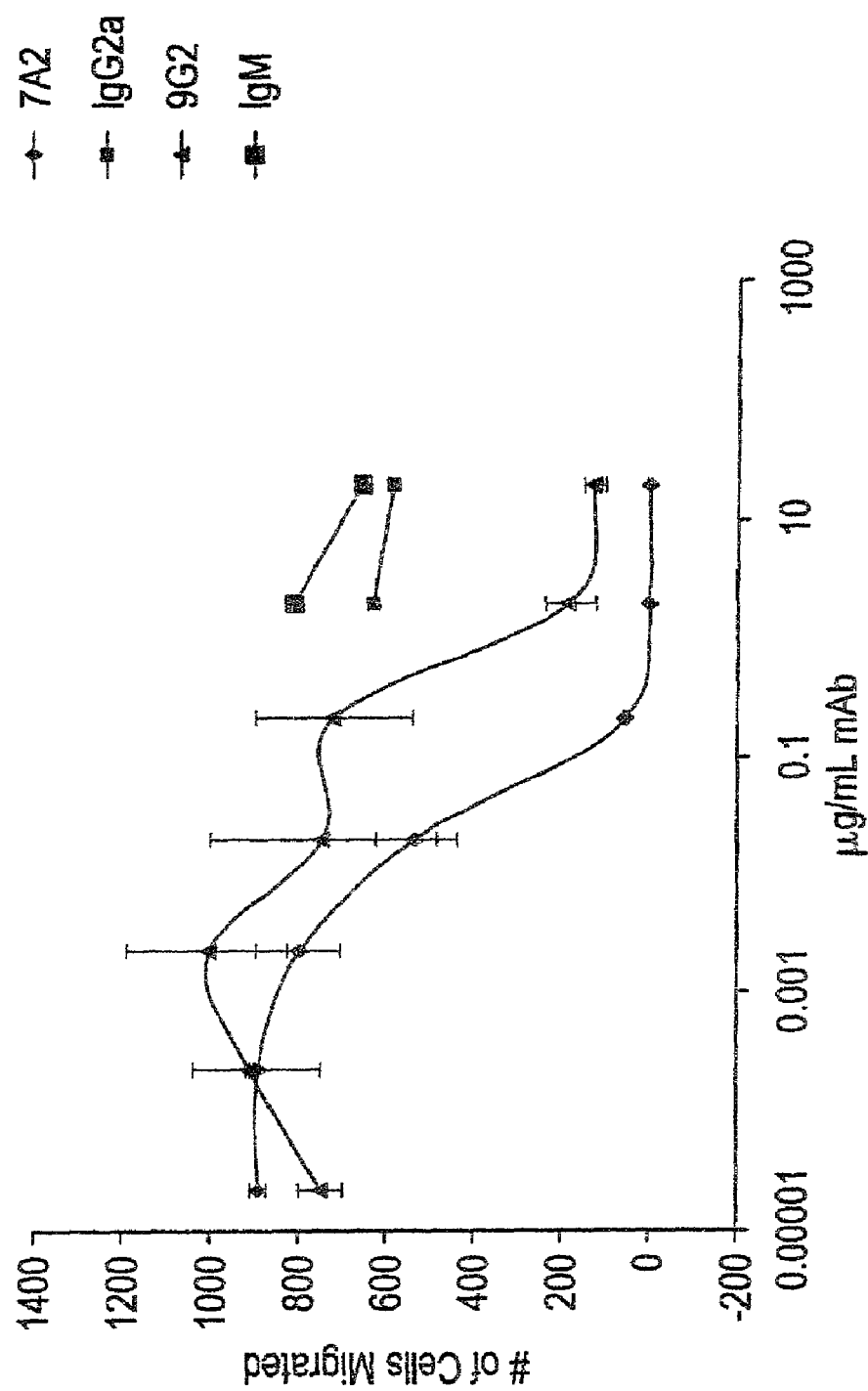

FIG. 31 is a graph showing dose dependent inhibition of SExCkine-induced chemotaxis of Bonzo/L1.2 cells by mAb 7A2 or mAb 9G2. Bonzo/L1.2 cells were incubated with concentrated supernatant from murine hybridoma 7A2 which produces mAb 7A2, from murine hybridoma 9G2 which produces mAb 9G2, or from a murine hybridoma which produces an isotype control antibody (IgG2a or IgM), prior to exposure to SExCkine.

Figure 32:
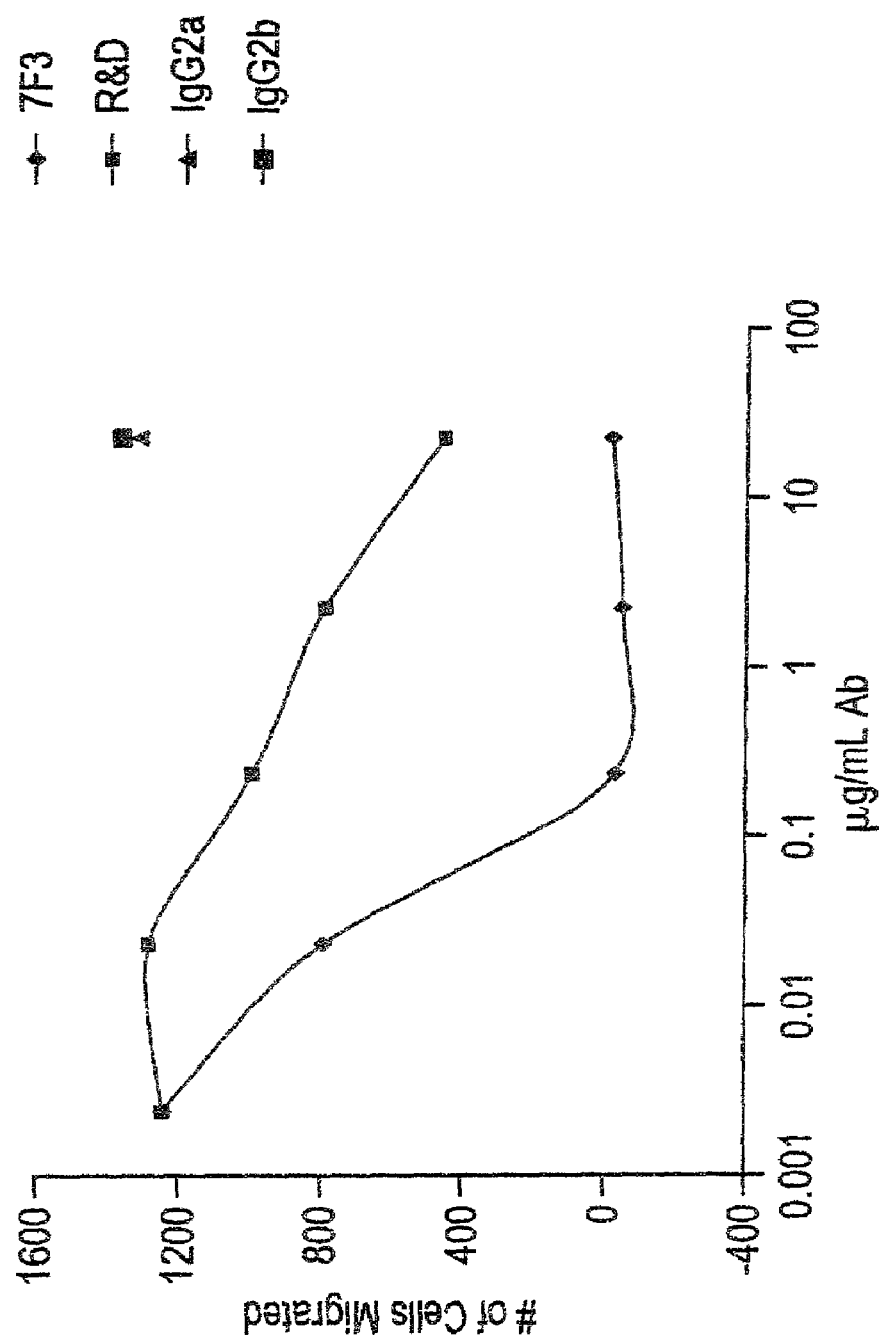

FIG. 32 is a graph illustrating dose dependent inhibition of SExCkine-induced chemotaxis of Bonzo/L1.2 cells by anti-Bonzo antibodies in an in vitro chemotaxis assay. Bonzo/L1.2 cells were incubated with purified mAb 7F3, with anti-human STRL33/Bonzo monoclonal antibody from R&D Systems, Minneapolis, Minn. (catalogue number MAB699) or isotype control antibodies (IgG2a or IgG2b), prior to exposure to SExCkine. The $IC_{50}$ for mAb 7F3 was determined to be 0.025 µg/mL, and the $IC_{50}$ for the antibody from R&D systems was determined to be 7.97 µg/mL.

DETAILED DESCRIPTION OF THE INVENTION

Chemokines and their receptors constitute an important component in the regulation of directed leukocyte migration. Chemokines are produced at sites of inflammation and attract various leukocytes bearing the corresponding receptors. While the spectrum of chemokines expressed at the inflammatory site can differentially attract certain inflammatory cells, selectivity and variation in chemokine receptor expression on leukocytes provides further regulation to ensure appropriate cell recruitment in response to particular inflammatory stimuli. As the number of identified and characterized chemokine receptors continues to grow, it is becoming increasingly clear that cells selectively express several receptors which may identify, mark, or otherwise characterize functional subsets of leukocytes such as $T_H1$, $T_H2$ and $T_R1$, naive and memory, activated and quiescent T cells. Because several characterized and/or orphan chemokine receptors can be co-expressed on individual cells, it has been difficult to validate the role of specific receptors in the initiation and progression of disease or, for that matter, in normal immune function.

As described herein, a study of the orphan chemokine receptor Bonzo (also referred to as STRL33 (Liao, F. et al., *J. Exp. Med.*, 185:2015–2023 (1997), TYMSTR (Loetscher, M. et al., *Current Biology*, 7:652–660 (1997) and HBMBU14 (Elshourbagy et al., U.S. Pat. No. 5,824,504; EP 0 834 563 A2)) was conducted. In the course of the study, a chemokine which binds and activates Bonzo was isolated. This chemokine is referred to herein as SExCkine (also referred to as chemokine alpha-5 (WO 99/27078)). Antibodies which bind human Bonzo (e.g., mAb 4A11, mAb 7A2, mAb 7F3, mAb 9G2) were produced and used to analyze the expression and function of the receptor on various types of leukocytes. The receptor was found to be expressed on small populations of both CD4$^+$ and CD8$^+$ T cells and on CD16⁺/CD56⁺ NK cells, but was not found on CD19⁺/CD20⁺ B cells or CD14⁺ monocytes. The receptor is expressed by both skin homing (CLA⁺) and mucosal homing (α4β7$^{hi}$ and (αE⁺) CD4⁺ lymphocytes. Bonzo is expressed predominantly on the memory subset of lymphocytes (CD45RO$^{hi}$), however, some expression was detected on naive (CD45RA$^{hi}$) cells. Bonzo expression was increased on activated cells (e.g., in vitro derived CD3 blasts, $T_H1$, $T_H2$, $T_R1$ and lymphokine-activated killer cells (LAK)).

The invention relates to the chemokine receptor Bonzo and to agents (e.g., ligands, antibodies, antagonists, agonists) which bind to the receptor. In one aspect, the invention relates to methods for detecting or identifying an agent (i.e., molecule or compound) which can bind to a mammalian Bonzo or a ligand-binding variant thereof.

Binding Assays

As used herein "mammalian Bonzo" refers to naturally occurring or endogenous mammalian Bonzo proteins and to proteins having an amino acid sequence which is the same as that of a naturally occurring or endogenous corresponding mammalian Bonzo protein (e.g., recombinant proteins, synthetic proteins (i.e., produced using the methods of synthetic organic chemistry)). Accordingly, as defined herein, the term includes mature receptor protein, polymorphic or allelic variants, and other isoforms of a mammalian Bonzo (e.g., produced by alternative splicing or other cellular processes), and modified or unmodified forms of the foregoing (e.g., lipidated, glycosylated, unglycosylated). Naturally occurring or endogenous mammalian Bonzo proteins include wild type proteins such as mature Bonzo, polymorphic or allelic variants and other isoforms which occur naturally in mammals (e.g., humans, non-human primates). Such proteins can be recovered or isolated from a source which naturally produces mammalian Bonzo, for example. These proteins and mammalian Bonzo proteins having the same amino acid sequence as a naturally occurring or endogenous corresponding mammalian Bonzo, are referred to by the name of the corresponding mammal. For example, where the corresponding mammal is a human, the protein is designated as a human Bonzo protein (e.g., a recombinant human Bonzo produced in a suitable host cell).

"Functional variants" of mammalian Bonzo proteins include functional fragments, functional mutant proteins, and/or functional fusion proteins which can be produce using suitable methods (e.g., mutagenesis (e.g., chemical mutagenesis, radiation mutagenesis), recombinant DNA techniques). A "functional variant" is a protein or polypeptide which has at least one function characteristic of a mammalian Bonzo protein as described herein, such as a binding activity, a signaling activity and/or ability to stimulate a cellular response. Preferred functional variants can bind a ligand (i.e., one or more ligands, such as SExCkine).

Generally, fragments or portions of mammalian Bonzo proteins include those having a deletion (i.e., one or more deletions) of an amino acid (i.e., one or more amino acids) relative to the mature mammalian Bonzo protein (such as N-terminal, C-terminal or internal deletions). Fragments or portions in which only contiguous amino acids have been deleted or in which non-contiguous amino acids have been deleted relative to mature mammalian Bonzo protein are also envisioned.

Mutant mammalian Bonzo proteins include natural or artificial variants of a mammalian Bonzo protein differing by the addition, deletion and/or substitution of one or more contiguous or non-contiguous amino acid residues (e.g., receptor chimeras). Such mutations can occur at one or more sites on a protein, for example a conserved region or nonconserved region (compared to other chemokine receptors or G-protein coupled receptors), extracellular region, cytoplasmic region, or transmembrane region.

Fusion proteins encompass polypeptides comprising a mammalian Bonzo (e.g., human Bonzo) or a variant thereof as a first moiety, linked via a covalent bond (e.g., a peptide bond) to a second moiety not occurring in the mammalian Bonzo as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag (e.g., hemagglutinin (HA)), a binding domain) as the first moiety, and a second moiety comprising a linker sequence and human Bonzo or a portion thereof. Additional (e.g., third, fourth) moieties can be present as appropriate.

In one embodiment, a functional variant of mammalian Bonzo (e.g., a ligand binding variant) shares at least about 80% amino acid sequence similarity with said mammalian Bonzo, preferably at least about 90% amino acid sequence similarity, and more preferably at least about 95% amino acid sequence similarity with said mammalian Bonzo. In another embodiment, a functional fusion protein comprises a first moiety which shares at least about 85% sequence similarity with a mammalian Bonzo, preferably at least about 90% sequence similarity, and more preferably at least about 95% sequence similarity with a mammalian Bonzo (e.g., a human Bonzo (e.g., SEQ ID NO:2)). In another embodiment, a functional mammalian Bonzo protein or functional variant of a mammalian Bonzo protein shares at least about 80% amino acid sequence similarity, preferably at least about 90% amino acid sequence similarity, and more preferably at least about 95% amino acid sequence similarity with a naturally occurring human Bonzo (e.g., SEQ ID NO:2). Amino acid sequence similarity can be determined using a suitable sequence alignment algorithm, such as the Lasergene system (DNASTAR, Inc., Madison, Wis.), using the Clustal method with the PAM 250 residue weight table, a gap penalty of 10, a gap length penalty of 10 and default parameters (pairwise alignment parameters: ktuple=1, gap penalty=3, window=4 and diagonals saved=5). In one embodiment, a mammalian Bonzo or portion thereof is encoded by a nucleic acid sequence which is different from a naturally-occurring nucleic acid sequence, but which, due to the degeneracy of the genetic code, encodes mammalian Bonzo or a portion thereof.

A composition comprising a mammalian Bonzo or functional variant thereof can be used in a binding assay to detect and/or identify agents that can bind to the receptor. Compositions suitable for use in a binding assay include, for example, cells which naturally express a mammalian Bonzo or functional variant thereof, such as Bonzo⁺ memory lymphocytes, CD3⁺CD56⁺CD8⁺Bonzo⁺ cytotoxic effector cells, lymphokine-activated killer (LAK) cells, cytokine-induced killer (CIK) cells, anti-CD3 generated lymphoblasts, cell lines and recombinant cells comprising an exogenous nucleic acid sequence which encodes a mammalian Bonzo or functional variant thereof. Compositions suitable for use in a binding assay also include, membrane preparations which comprise a mammalian Bonzo or functional variant thereof Such membrane preparations can contain natural (e.g., plasma membrane) or synthetic membranes. Preferably, the membrane preparation is a membrane fraction of a cell that expresses a mammalian Bonzo or a functional variant thereof.

In one embodiment, the method of detecting or identifying an agent that binds to a mammalian Bonzo is a competitive binding assay in which the ability of a test agent to inhibit the binding of a reference agent (e.g., a ligand, an antibody) is assessed. For example, the reference agent can be labeled with a suitable label as described herein, and the amount of labeled reference agent required to saturate the Bonzo present in the assay can be determined. A saturating amount of labeled reference agent and various amounts of a test agent can be contacted with a composition comprising a mammalian Bonzo or functional variant thereof under conditions suitable for binding, and complex formation determined. In this type of assay, a decrease in the amount of complex formed between the labeled reference agent and Bonzo or functional variant thereof indicates that the test agent binds to Bonzo.

The formation of a complex between the reference agent and the Bonzo or functional variant thereof can be detected or measured directly or indirectly using any suitable method. For example, the reference agent can be labeled with a suitable label and the formation of a complex can be determined by detection of the label. The specificity of the complex can be determined using a suitable control such as excess unlabeled reference agent or label alone. Labels suitable for use in detection of a complex between an agent and a mammalian Bonzo or functional variant thereof include, for example, a radioisotope, an epitope label (tag), an affinity label (e.g., biotin, avidin), a spin label, an enzyme, a fluorescent group or a chemiluminescent group. When labels are not employed, complex formation can be determined by surface plasmon resonance or other suitable methods.

The capacity of the test agent to inhibit the formation of a complex between the reference agent and a mammalian Bonzo can be reported as the concentration of test agent required for 50% inhibition ($IC_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian Bonzo or a functional variant thereof, for example, a chemokine ligand of Bonzo or an antibody. In one embodiment, neither the reference agent nor the test agent is platelet factor 4 or a Bonzo-binding variant (e.g., fragment) thereof. In a preferred embodiment, the reference agent is a mammalian SexCkine or a receptor-binding variant thereof.

As used herein "mammalian SExCkine" refers to naturally occurring or endogenous mammalian SExCkine proteins (e.g., SEQ ID NO:4, SEQ ID NO:6) and to proteins having an amino acid sequence which is the same as that of a naturally occurring or endogenous corresponding mammalian SExCkine protein (e.g., recombinant proteins, synthetic proteins (i.e., produced using the methods of synthetic organic chemistry)). Accordingly, as defined herein, the term includes mature protein, polymorphic or allelic variants, and other isoforms of a mammalian SExCkine (e.g., produced by alternative splicing, proteolytic processing or other cellular processes), and modified or unmodified forms of the foregoing (e.g., lipidated, glycosylated (e.g., with glycosaminoglycans), unglycosylated,). Naturally occurring or endogenous mammalian SExCkine proteins include wild type proteins such as transmembrane SExCkine and soluble SExCkine, polymorphic or allelic variants and other isoforms which occur naturally in mammals (e.g., humans, non-human primates). Such proteins can be recovered or isolated from a source which naturally produces mammalian SExCkine, for example. These proteins and mammalian SExCkine proteins having the same amino acid sequence as a naturally occurring or endogenous corresponding mammalian SExCkine, are referred to by the name of the corresponding mammal. For example, where the corresponding mammal is a human, the protein is designated as a human SExCkine protein (e.g., a recombinant human SExCkine produced in a suitable host cell).

"Receptor-binding variants" of mammalian SExCkine proteins include receptor-binding fragments (e.g., proteolytic fragments), receptor-binding mutant proteins and receptor-binding fusion proteins which can be produce using suitable methods (e.g., mutagenesis (e.g., chemical mutagenesis, radiation mutagenesis), recombinant DNA techniques). A "receptor-binding variant" can be identified using a suitable receptor-binding assay such as a Bonzo-binding assay described herein.

Generally, fragments or portions of mammalian SExCkine proteins include those having a deletion (i.e., one or more deletions) of an amino acid (i.e., one or more amino acids) relative to the mature mammalian SExCkine protein (such as N-terminal, C-terminal or internal deletions). Fragments or portions in which only contiguous amino acids have been deleted or in which non-contiguous amino acids have been deleted relative to mature mammalian SExCkine protein are also envisioned.

Mutant mammalian SExCkine proteins include natural or artificial variants of a mammalian SExCkine protein differing by the addition, deletion and/or substitution of one or more contiguous or non-contiguous amino acid residues (e.g., receptor chimeras). Such mutations can occur at one or more sites on a protein, for example a conserved region or nonconserved region (compared to other chemokines), extracellular region, cytoplasmic region, or transmembrane region.

Fusion proteins encompass polypeptides comprising a mammalian SExCkine (e.g., human SExCkine) or a receptor-binding variant thereof as a first moiety, linked via a covalent bond (e.g., a peptide bond) to a second moiety not occurring in the mammalian SExCkine or variant as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) as the first moiety, and a second moiety comprising a linker sequence and human SExCkine or a portion thereof. Additional (e.g., third, fourth) moieties can be present as appropriate.

Receptor-binding variants of SExCkine include, for example, polypeptides which have the amino acid sequence of residues 1–202, 30–202, 1–155, 30–155, 1–117 or 30–117 of human SExCkine (e.g., SEQ ID NO:4). Additional receptor-binding variants of mammalian SExCkine (e.g., human SExCkine) can be polypeptides of from about 10 to about 128 amino acid residues or from about 40 to about 80 amino acid residues which comprise the amino acid sequence of a portion of the extracellular region of mammalian SExCkine (e.g., residues 30–202 of SEQ ID NO:4). For example, a synthetic peptide consisting of amino acid residues 30 (Asn) to 95 (Ser) of human SExCkine (SEQ ID NO:4) has been synthesized. This sixty-six amino acid peptide bound Bonzo and induced migration of Bonzo/L1.2 cells in a chemotaxis assay.

Receptor-binding variants of mammalian SExCkine also include proteins and polypeptides in which one or more naturally occurring amino acid residues are conservatively substituted. A conservative amino acid substitution refers to the replacement of a first amino acid by a second amino acid that has chemical and/or physical properties (e.g., charge, structure, polarity, hydrophobicity/hydrophilicity) which are similar to those of the first amino acid. Groups of amino acids with similar chemical and/or physical properties include, for example, those with hydrophilic side chains (e.g., asparagine, glutamine, serine, threonine, tyrosine, lysine, arginine, histidine, aspartate, glutamate), hydrophobic side chains (e.g., alanine, valine, leucine, isoleucine, proline, phenylalanine, tryptophan, methionine, cysteine, glycine), acidic side chains (e.g., aspartate, glutamate), basic side chains (e.g., lysine, arginine, histidine), aromatic side chains (e.g., phenylalanine, tryptophan, histidine, tyrosine) and nucleophilic side chains (e.g., cysteine, serine, threonine).

In one embodiment, the receptor-binding variant of mammalian SExCkine shares at least about 85% sequence similarity with a corresponding portion of a naturally occurring mammalian SExCkine (e.g., SEQ ID NO:4, SEQ ID NO:6), preferably at least about 90% sequence similarity, and more preferably at least about 95% sequence similarity with a corresponding portion of a naturally occurring mammalian SExCkine. Amino acid sequence similarity can be identified by aligning the amino acid sequence of the receptor binding variant with the amino acid sequence of mammalian SExCkine (e.g., SEQ ID NO:4, SEQ ID NO:6) using a suitable sequence alignment algorithm, such as the Lasergene system (DNASTAR, Inc., Madison, Wis.), as described herein. Variants can be prepared using any suitable methods, (e.g., solid phase peptide synthesis, by expression of nucleic acids encoding the variant), and tested for receptor binding.

The invention also relates to a method of identifying or isolating an agent (i.e., molecule or compound) which can be used in therapy, as described herein. In one embodiment, the agent is identified or isolated in a competitive binding assay as described above. In another embodiment, cells which express a mammalian Bonzo or a functional variant thereof are maintained under conditions appropriate for expression of receptor. The cells are contacted with an agent (e.g., ligand, antagonist, agonist) under conditions suitable for binding (e.g., in a suitable binding buffer), and the formation of a complex between the agent and said mammalian Bonzo or functional variant thereof is detected or measured using suitable techniques. For example, the agent can be labeled as described herein and the amount of label present in an agent-Bonzo complex can be determined. The extent of complex formation can be determined relative to a suitable control (e.g., compared with background determined in the absence of agent, compared with binding of a second agent (i.e., a standard, an isotype control), compared with binding of agent to cells that do not express Bonzo).

Thus, the invention relates to a method of identifying or isolating an agent for use in treating a subject having an inflammatory disease. In another embodiment, the method is a method of identifying or isolating an agent for use in inhibiting a cellular response to ligand binding to Bonzo$^+$ leukocytes. In another embodiment, the method is a method of identifying or isolating an agent for use in modulating a Bonzo-mediated function in a subject.

A variety of agents, such as proteins (e.g., antibodies), peptides, peptidomimetics, small organic molecules, nucleic acids and the like, can be tested for Bonzo binding. According to the method of the present invention, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds (e.g., a ligand, inhibitor, promoter) in a test sample can also be determined according to these methods.

Agents which bind to a mammalian Bonzo and which are useful in the therapeutic methods described herein can be identified, for example, by screening libraries or collections of molecules, such as, the Chemical Repository of the National Cancer Institute, in assays described herein or using other suitable methods. Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In another embodiment, the reference and test agents employed in the method are not viruses or viral proteins (e.g., viral envelope proteins). In another embodiment, the collection of agents tested according to the methods of the invention does not comprise chemokines or mutants or analogues thereof.

Functional Assays

Functional assays can be used to detect and identify agonists (promotors) and antagonists (inhibitors) of a mammalian Bonzo receptor. An agent can be studied in one or more suitable functional assays to determine if said agent can modulate (inhibit (reduce or prevent) or promote) one or more functions of Bonzo. For example, an agent can be tested in an extracellular acidification assay, calcium flux assay, ligand binding assay, chemotaxis assay or assay which monitors degranulation or inflammatory mediator release (see, for example, Hesselgesser et al., *J. Biol. Chem.* 273(25):15687–15692 (1998) and WO 98/02151).

For example, an agent which binds to a mammalian Bonzo or functional variant thereof can be tested in a leukocyte chemotaxis assay using suitable cells. Suitable cells include, for example, cell lines, recombinant cells or isolated cells which express a mammalian Bonzo and undergo Bonzo ligand-induced (e.g., SExCkine-induced) chemotaxis. In one example, Bonzo-expressing recombinant L1.2 cells (see Campbell, et al. *J Cell Biol*, 134:255–266 (1996) regarding L1.2 cells), can be used in a modification of a transendothelial migration assay (Carr, M. W., et al. T. A., *Proc. Natl Acad Sci, USA*, (91):3652 (1994)). The endothelial cells used in this assay are preferably the endothelial cell line, ECV 304, which can be obtained from the American Type Culture Collection (Manassas, Va.). Endothelial cells can be cultured on 6.5 mm diameter Transwell culture inserts (Costar Corp., Cambridge, Mass.) with 3.0

µm pore size. Culture media for the ECV 304 cells can consist of M199+10% FCS, L-glutamine, and antibiotics. The assay media can consist of equal parts RPMI 1640 and M199 with 0.5% BSA. Two hours before the assay, $2 \times 10^5$ ECV 304 cells can be plated onto each insert of the 24 well Transwell chemotaxis plate and incubated at 37° C. Chemotactic factor such as SExCkine can be added to the 24-well tissue culture plates in a final volume of 600 µL. Endothelial-coated Transwells can be inserted into each well and $10^6$ cells of the leukocyte type being studied can be added to the top chamber in a final volume of 100 µL of assay medium. The plate can then be incubated at 37° C. in 5% $CO_2$/95% air for 1–2 hours. The cells that migrate to the bottom chamber during incubation can be counted, for example using flow cytometry. To count cells by flow cytometry, 500 µL of the cell suspension from the lower chamber can be placed in a tube and relative counts can obtained for a set period of time, for example, 30 seconds. This counting method is highly reproducible and allows gating on the leukocytes and the exclusion of debris or other cell types from the analysis. Alternatively, cells can be counted with a microscope. Assays to evaluate agents that can inhibit or promote chemotaxis can be performed in the same way as control experiment described above, except that agent solutions, in assay media containing up to 1% of DMSO co-solvent, can be added to both the top and bottom chambers prior to addition of the cells. The capacity of an agent to inhibit or promote chemotaxis can be determined by comparing the number of cell that migrate to the bottom chamber in wells which contain the agent, to the number of cells which migrate to the bottom chamber in control wells. Control wells can contain equivalent amounts of DMSO, but no agent.

An agent can also be assessed by monitoring cellular responses induced by active receptor, using suitable cells which express a mammalian Bonzo or a functional variant thereof. For instance, exocytosis (e.g., degranulation of cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods (see e.g., Taub, D. D. et al., *J. Immunol.*, 155: 3877–3888 (1995), regarding assays for release of granule-derived serine esterases; Loetscher et al., *J. Immunol.*, 156: 322–327 (1996), regarding assays for enzyme and granzyme release; Rot, A. et al., *J. Exp. Med.*, 176: 1489–1495 (1992) regarding respiratory burst; Bischoff, S. C. et al., *Eur. J. Immunol.*, 23: 761–767 (1993) and Baggliolini, M. and C. A. Dahinden, *Immunology Today*, 15: 127–133 (1994)). A variety of functional assays which employ recombinant cells which express a mammalian Bonzo or functional variant thereof can be employed. For example, assays in which expression of an endogenous or exogenous reporter gene (e.g., β-galactosidase, green fluorescent protein) is induced upon ligand binding to a mammalian Bonzo or variant expressed by recombinant cells ( e.g., recombinant bacteria, recombinant yeast, recombinant mammalian cells) can be used.

In one embodiment, an agent that can inhibit or promote a function of Bonzo is identified by monitoring the release of an enzyme upon degranulation or exocytosis by a cell capable of this function. Cells expressing a mammalian Bonzo or a functional variant thereof can be maintained in a suitable medium under suitable conditions, and degranulation can be induced. The cells are contacted with an agent to be tested, and enzyme release can be assessed. The release of an enzyme into the medium can be detected or measured using a suitable assay, such as an immunological assay, or biochemical assay for enzyme activity.

The medium can be assayed directly, by introducing components of the assay (e.g., substrate, co-factors, antibody) into the medium (e.g., before, simultaneously with or after the cells and agent are combined). The assay can also be performed on medium which has been separated from the cells or further processed (e.g., fractionated) prior to assay. For example, convenient assays are available for enzymes, such as serine esterases (see e.g., Taub, D. D. et al., *J. Immunol.*, 155: 3877–3888 (1995) regarding release of granule-derived serine esterases).

In another embodiment, cells expressing a mammalian Bonzo or a functional variant thereof are combined with a ligand of Bonzo (e.g., SExCkine), an agent to be tested is added before, after or simultaneous therewith, and $Ca^{2+}$ flux is assessed. Inhibition of ligand-induced $Ca^{2+}$ flux is indicative that the agent is an inhibitor or antagonist of mammalian Bonzo function.

Engagement of the chemokine receptors of a lymphocyte can cause integrin activation, and induction of adherence to adhesion molecules expressed in vasculature or the perivascular space. Cellular adherence can be monitored by methods known in the art or other suitable methods. In one embodiment, a ligand, inhibitor and/or promoter of Bonzo function is identified by monitoring cellular adherence by a cell capable of adhesion. For example, an agent to be tested can be combined with (a) cells expressing a mammalian Bonzo or a functional variant thereof (preferably nonadherent cells which when transfected with receptor and stimulated with agonists (e.g., ligand) acquire adhesive ability), (b) a composition comprising a suitable adhesion molecule (e.g., a substrate such as a culture well coated with an adhesion molecule, such as fibronectin), and (c) a ligand or promoter (e.g., SExCkine), and maintained under conditions suitable for ligand- or promoter-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signaling, and/or cellular responses. In another embodiment, an agent to be tested can be combined with cells expressing a mammalian Bonzo or a functional variant thereof and a composition comprising a suitable adhesion molecule under conditions suitable for ligand- or promoter-induced adhesion, and adhesion is monitored. Increased adhesion relative to a suitable control is indicative of the presence of a ligand and/or promoter.

The binding assays and functional assays described above can be used, alone or in combination with each other or other suitable methods, to detect or identify agents which bind a mammalian Bonzo protein and/or modulators (antagonists, agonists) of a Bonzo protein function. The in vitro methods of the present invention can be adapted for high-throughput screening in which large numbers of samples are processed (e.g., a 96-well format). Cells expressing a mammalian Bonzo (e.g., human Bonzo) or a functional variant thereof at levels suitable for high-throughput screening can be used, and thus, are particularly valuable in the identification and/or isolation of agents which bind Bonzo, and modulators of Bonzo function. Expression of Bonzo or a variant thereof can be monitored in a variety of ways. For instance, expression can be monitored using antibodies of the present invention which bind receptor or a portion thereof or using a Bonzo ligand (e.g., SExCkine, platelet factor 4). Also, commercially available antibodies can be used to detect expression of an antigen- or epitope-tagged fusion protein comprising a receptor protein or polypeptide (e.g., FLAG tagged receptors), and cells expressing the Bonzo or functional variant at the desired level can be selected (e.g., by flow cytometry).

Antibodies and Antibody Producing Cells

The invention relates to antibodies which bind to mammalian Bonzo and to antibodies which bind to mammalian SExCkine. Preferred antibodies of the invention can bind to Bonzo or SExCkine and thereby inhibit the binding of ligand to receptor. The antibody of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments of antibodies which bind to a mammalian Bonzo, and antigen-binding fragments of antibodies which bind to a mammalian SExCkine. For example, antibody fragments capable of binding to a mammalian Bonzo or SExCkine or portions thereof, including, but not limited to Fv, Fab, Fab' and F(ab')$_2$ fragments are encompassed by the invention. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455–1460 (1992), regarding primatized antibody, and Ladner et al., U.S. Pat. No. 4,946,778 and Bird, R. E. et al., Science, 242: 423–426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851–856 (1993); Daugherty, B. L. et al., Nucleic Acids Res., 19(9): 2471–2476 (1991); and Lewis, A. P. and J. S. Crowe, Gene, 101: 297–302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for mammalian (e.g., human) Bonzo or mammalian (e.g., human) SExCkine can be raised against an appropriate immunogen, such as isolated and/or recombinant human Bonzo or portions thereof (including synthetic molecules, such as synthetic peptides) or isolated and/or recombinant human SExCkine or portions thereof (including synthetic molecules, such as synthetic peptides). Antibodies can also be raised by immunizing a suitable host (e.g., mouse) with cells that express Bonzo, such as activated T cells. In addition, cells expressing a recombinant mammalian Bonzo or SExCkine, such as transfected cells, can be used as immunogens or in a screen for antibody which binds thereto (See e.g., Chuntharapai et al., J. Immunol., 152: 1783–1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies (see e.g., Jakobovits et al., Proc. Natl. Acad. Sci. USA, 90: 2551–2555 (1993); Jakobovits et al., Nature, 362: 255–258 (1993); Lonberg et al., U.S. Pat. No. 5,545,806; Surani et al., U.S. Pat. No. 5,545,807; Lonberg et al., WO97/13852).

In one embodiment, the antibody or antigen-binding fragment thereof has specificity for a mammalian Bonzo, preferably a naturally occurring or endogenous human Bonzo. In another embodiment, the antibody is an IgG or antigen-binding fragment of an IgG. In another embodiment, the antibody or antigen-binding fragment can bind to a mammalian Bonzo and inhibit (reduce or prevent) one or more functions of the receptor. In another embodiment, the antibody is a human antibody or an antigen-binding fragment thereof. In another embodiment, the antibody is a humanized antibody or an antigen-binding fragment thereof. In a preferred embodiment, the antibody or antigen-binding fragment can inhibit binding of a ligand (i.e., one or more ligands) to the receptor, and/or one or more functions mediated by Bonzo in response to ligand binding.

In a particular embodiment, an antibody or antigen-binding fragment of the invention can inhibit the binding of a mammalian ligand (e.g., human SExCkine) to mammalian (e.g., human) Bonzo and/or one or more functions (e.g., cellular response) mediated by Bonzo in response to ligand binding. Inhibition of a cellular response to binding of ligand to Bonzo can be assessed in a suitable in vitro assay. Preferably, the antibody or antigen-binding fragment of the invention can inhibit a cellular response to binding of ligand to Bonzo in an in vitro assay with an $IC_{50}$ of less than about 10 µg/mL. Also preferred are antibodies and antigen-binding fragments which inhibit a ligand-induced (e.g., SExCkine-induced) cellular response in an in vitro chemotaxis assay with an $IC_{50}$ of less than about 8 µg/mL, or less than about 7 µg/mL, or less than about 5 µg/mL, or less than about 1 µg/mL. Particularly preferred antibodies and antigen-binding fragments which inhibit a ligand-induced (e.g., SExCkine-induced) cellular response in an in vitro assay with an $IC_{50}$ of less than about 0.5 µg/mL or less than about 0.1 µg/mL. In one embodiment, the antibody or antigen-binding fragment can inhibit ligand-induced (e.g., SExCkine-induced) chemotaxis of Bonzo$^+$ cells (e.g., Bonzo/L1.2 cells) in an in vitro chemotaxis assay, such as the assay described herein. In another embodiment, the antibody or antigen-binding fragment can inhibit a ligand-induced (e.g., SExCkine-induced) cellular response in an in vitro assay (e.g., chemotaxis assay) with an $IC_{50}$ that is lower than the $IC_{50}$ of the anti-human STRL33/Bonzo monoclonal antibody available from R&D Systems, Minneapolis, Minn. (catalogue number MAB699). In one embodiment, the $IC_{50}$ of the antibody or antigen-binding fragment of the invention is lower than the $IC_{50}$ of the anti-human STRL33/Bonzo monoclonal antibody available from R&D Systems (catalogue number MAB699) by a factor of about 2 or more. For example, the $IC_{50}$ of the antibody or antigen-binding fragment of the invention can be lower than the $IC_{50}$ of the anti-human STRL33/Bonzo monoclonal antibody available from R&D Systems (catalogue number MAB699) by a factor of about 2, 3, 4, 5, 8, 10, 50, 100, 500, or 1000.

Other functions which can be mediated by Bonzo in response to ligand binding (e.g., SExCkine) include, for example, signal transduction (e.g., GDP/GTP exchange by Bonzo associated G proteins, transient increase in the concentration of cytosolic free calcium $[Ca^{2+}]_i$) and Bonzo-mediated processes and cellular responses (e.g., proliferation, migration, chemotaxis, secretion, degranulation, inflammatory mediator release (such as release of bioactive lipids such as leukotrienes (e.g., leukotriene $C_4$)), respiratory burst).

As described herein, antibodies designated "mAb 4A11", "mAb 7A2", "mAb 7F3" and "mAb 9G2" which bind human Bonzo have been produced.

mAb 4A11 can be produced by murine hybridoma 4A11, also referred to as murine hybridoma LS212-4A11-30-8, which was deposited on Nov. 24, 1999, on behalf of LeukoSite, Inc., 215 First Street, Cambridge, Mass. 02142, U.S.A. (now Millennium Pharmaceuticals, Inc., 75 Sidney Street, Cambridge, Mass. 02139, U.S.A.), at the American Type Culture Collection, 10801 University Boulevard, Manassas, Va. 20110, U.S.A., under Accession No. PTA-991. The invention relates to murine hybridoma 4A11, to the antibody it produces and to nucleic acids encoding the antibody.

mAb 7A2 can be produced by murine hybridoma 7A2, also referred to as murine hybridoma LS212-7A2-32-1, which was deposited on Nov. 24, 1999, on behalf of LeukoSite, Inc., 215 First Street, Cambridge, Mass. 02142, U.S.A. (now Millennium Pharmaceuticals, Inc., 75 Sidney Street, Cambridge, Mass. 02139, U.S.A.), at the American Type Culture Collection, 10801 University Boulevard, Manassas, Va. 20110, U.S.A., under Accession No. PTA-992. The invention relates to murine hybridoma 7A2, to the antibody it produces, and to nucleic acids encoding the antibody.

mAb 7F3 can be produced by murine hybridoma 7F3, also referred to as murine hybridoma LS212-7F3-8-7, which was deposited on Nov. 24, 1999, on behalf of LeukoSite, Inc., 215 First Street, Cambridge, Mass. 02142, U.S.A. (now Millennium Pharmaceuticals, Inc., 75 Sidney Street, Cambridge, Mass. 02139, U.S.A.), at the American Type Culture Collection, 10801 University Boulevard, Manassas, Va. 20110, U.S.A., under Accession No. PTA-990. The invention relates to murine hybridoma 7F3, to the antibody it produces, and to nucleic acids encoding the antibody.

mAb 9G2 can be produced by murine hybridoma 9G2, also referred to as murine hybridoma LS212-9G2-7-2. The invention relates to murine hybridoma 9G2, to the antibody it produces, and to nucleic acids encoding the antibody.

In another embodiment, the anti-Bonzo antibody of the invention is mAb 4A11, mAb 7A2, mAb 7F3, mAb 9G2 or an antigen-binding fragment of any of the forgoing. Preferred among these are mAb 4A11, mAb 7A2, mAb 7F3 or antigen-binding fragments thereof. In another embodiment, the binding of the antibody or antigen-binding fragment to mammalian (e.g., human) Bonzo can be inhibited by mAb 4A11, mAb 7A2 or mAb 7F3. Such inhibition can be the result of competition for the same or similar epitope or steric interference (e.g., where antibodies bind overlapping epitopes or adjacent epitopes). Inhibition by mAb 4A11, mAb 7A2 or mAb 7F3 can also be due to a change in the conformation of Bonzo that is induced upon antibody binding to the receptor.

In still another embodiment, the antibody or antigen-binding fragment of the invention has the same or similar epitopic specificity as mAb 4A11, mAb 7A2, mAb 7F3 or mAb 9G2. Antibodies with an epitopic specificity which is the same as or similar to that of mAb 4A11, mAb 7A2, mAb 7F3 or mAb 9G2 can be identified by a variety of suitable methods. For example, an antibody with the same or similar epitopic specificity as e.g., mAb 4A11 can be identified based upon the ability to compete with mAb 4A11 for binding to human Bonzo. In another example, the binding of e.g., 4A11 and the binding of an antibody with the same or similar epitopic specificity for human Bonzo can be inhibited by a single peptide (e.g., natural peptide, synthetic peptide). The peptide can comprise about nine to about fifty amino acids. Preferably, the peptide comprises about nine to about twenty-six amino acids. In still another example, an antibody with the same or similar epitopic specificity as mAb 4A11, mAb 7A2, mAb 7F3 or mAb 9G2 can be identified using chimeric receptors (see e.g., Rucker et al., Cell 87:437–446 (1996)).

The invention also relates to a bispecific antibody, or functional fragment thereof (e.g., F(ab')$_2$), which binds to a mammalian Bonzo and at least one other antigen (e.g., tumor antigen, viral antigen). In a particular embodiment, the bispecific antibody, or functional fragment thereof has the same or similar epitopic specificity as mAb 4A11, mAb 7A2, mAb 7F3 or mAb 9G2 and at least one other antibody. Bispecific antibodies can be secreted by triomas and hybrid hybridomsa. Generally, triomas are formed by fusion of a hybridoma and a lymphocyte (e.g., antibody secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen binding sites which recognize different antigens. The supernatants of triomas and hybrid hybridomas can be assayed for bispecific antibody using a suitable assay (e.g., ELISA), and bispecific antibodies can be purified using conventional methods. (see, e.g., U.S. Pat. No. 5,959,084 (Ring et al.) U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In another embodiment, the antibody or antigen-binding fragment thereof has specificity for a mammalian SExCkine, preferably a naturally occurring or endogenous human SExCkine. Such antibodies and antigen-binding fragments can be produced by a variety of suitable methods, such as those described herein. In one embodiment, the anti-SExCkine antibody can be raised against an appropriate immunogen, such as an isolated soluble and/or recombinant SExCkine or portions thereof (including synthetic molecules, such as synthetic peptides). Antibodies can also be raised by immunizing a suitable animal (e.g., mouse) with cells which express the transmembrane form of SExCkine. In another embodiment, the antibody is an IgG or antigen-binding fragment of an IgG. In another embodiment, the antibody is a human antibody or an antigen-binding fragment thereof. In another embodiment, the antibody is a humanized antibody or an antigen-binding fragment thereof. In a preferred embodiment, the antibody or antigen-binding fragment can bind to a mammalian sexcikine and inhibit (reduce or prevent) the binding of the chemokine to receptor (e.g., Bonzo), and thereby inhibit one or more functions mediated by receptor in response to SExCkine binding. For example, the anti-SExCkine antibody can inhibit SExCkine-induced chemotaxis of Bonzo$^+$ cells. Other functions which can be mediated by SExCkine binding to receptor (e.g., Bonzo) include, for example, signal transduction (e.g., GDP/GTP exchange by receptor associated G proteins, transient increase in the concentration of cytosolic free calcium $[Ca^{2+}]_i$) and receptor-mediated processes and cellular responses (e.g., proliferation, migration, chemotaxis, secretion, degranulation, inflammatory mediator release (such as release of bioactive lipids such as leukotrienes (e.g., leukotriene C$_4$)), respiratory burst).

The invention also relates to a bispecific antibody, or functional fragment thereof (e.g., F(ab')$_2$), which binds to a mammalian SExCkine and at least one other antigen (see, e.g., U.S. Pat. No. 5,959,084 (Ring et al.) U.S. Pat. No. 5,141,736 (Iwasa et al.), U.S. Pat. Nos. 4,444,878, 5,292, 668, 5,523,210 (all to Paulus et al.) and U.S. Pat. No. 5,496,549 (Yamazaki et al.)).

As used herein the term "specific antibody" or "specific" when referring to an antibody-antigen interaction is used to indicate that the antibody can selectively bind to a mammalian Bonzo or a mammalian SExCkine, rather than to indicate that the antibody can bind to only one antigen. For example, an antibody may bind to one or several antigens with low affinity and bind to human Bonzo with a higher affinity. Such an antibody is considered to be specific for human Bonzo because when used (e.g., in therapeutic or diagnostic application) at a suitable concentration, the antibody can selectively bind to human Bonzo. The concentration of antibody required to provide selectivity for mammalian Bonzo or mammalian SExCkine (e.g., a concentration which reduces or eliminates low affinity binding) can be readily determined by suitable methods, such as titration.

In another aspect, the invention relates to an isolated cell which produces an antibody or an antigen-binding fragment of the invention. In a preferred embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-Bonzo or anti-SExCkine immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225, 539)). For instance, clones comprising a sequence encoding a rearranged anti-Bonzo light and/or heavy chain can be isolated (e.g., by PCR) or cDNA libraries can be prepared from mRNA isolated from the cell lines, and cDNA clones encoding an anti-Bonzo immunoglobulin chain(s) can be isolated. Thus, nucleic acids encoding the heavy and/or light chains of the antibodies or portions thereof can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell.

The antibody of the invention can be produced by any suitable method, for example, by collecting serum from an animal (e.g., mouse, human, transgenic mouse) which has been immunized with a mammalian Bonzo or a mammalian SExCkine. In another example, a suitable antibody producing cell (e.g., hybridoma, heterohybridoma, lymphoblastoid cell, recombinant cell) can be maintained, either in vitro or in vivo, under conditions suitable for expression (e.g., in the presence of inducer, suitable media supplemented with appropriate salts, growth factors, antibiotic, nutritional supplements), whereby the antibody or antigen-binding fragment is produced. If desired, the antibody or antigen-binding fragment can be recovered and/or isolated (e.g., from the host cells, culture medium) and purified to the desired degree. Recovery and purification of the antibody can be achieved using suitable methods, such as, centrifugation, filtration, column chromatography (e.g., ion-exchange, gel filtration, hydrophobic-interaction, affinity), preparative native electrophoresis, precipitation and ultrafiltration. It will be appreciated that the method of production encompasses expression in a host cell of a transgenic animal (see e.g., WO 92/03918, GenPharm International, published Mar. 19, 1992).

As described herein, preferred antibodies of the invention can bind to mammalian Bonzo or mammalian SExCkine and thereby inhibit the binding of ligand to receptor. A variety of suitable methods, such as the assays described herein, can be used to assess inhibition of binding of a ligand (e.g., SExCkine) to a receptor (e.g., Bonzo) and/or function associated with binding of ligand to receptor.

The invention also includes antibodies and antigen-binding fragments thereof which can bind to mammalian Bonzo but which do not inhibit the binding of ligand to receptor.

Targeting Molecules

The invention also relates to targeting molecules which can effectuate the interaction of a Bonzo$^+$ cell with a target cell. The targeting molecule includes a first binding moiety which can bind mammalian Bonzo, and a second binding moiety which can bind a molecule expressed on the surface of a target cell. Preferred target cells include tumor cells and virus infected cells. A variety of molecules which are expressed at higher levels or uniquely on tumor cells (e.g., tumor antigens, such as Lewis Y, HER-2/neu, disialoganglioside G3, carcinoembrionic antigen, CD30) and/or virus infected cells (e.g., viral antigens, such as influenza virus hemagglutinin, Epstein-Barr virus LMP-1, hepatitis C virus E2 glycoprotein, HIV gp160, HIV gp 120) are known in the art. The targeting molecule can contain any suitable binding second moiety which binds to a molecule expressed on a desired target cell (see, for example Ring, U.S. Pat. No. 5,948,647, the entire teachings of which are incorporated herein by reference). Suitable binding moieties include, for example, proteins and peptides (including post-translationally modified forms e.g., glycosylated, phosphorylated, lipidated), sugars, lipids, peptidomimetics, small organic molecules, nucleic acids and other agents which bind mammalian Bonzo or a molecule expressed on the surface of a target cell. Suitable binding moieties can be identified using any suitable method, such as the binding assays described herein.

The first binding moiety can be, for example, and antibody which binds mammalian Bonzo or antigen-binding fragment thereof (e.g., Fab, Fv, Fab', F(ab')$_2$), a Bonzo ligand (e.g., mammalian SExCkine, mammalian platelet factor 4) or Bonzo-binding variant of a ligand. The second binding moiety can be, for example, an antibody or antigen-binding fragment thereof which binds to a molecule expressed on the target cell or antigen binding fragment thereof. Where the targeting molecule comprises a first binding moiety which is an anti-Bonzo antibody or antigen-binding fragment thereof, it is preferred that said anti-Bonzo antibody does not inhibit binding of ligand to Bonzo.

The first binding moiety can be directly or indirectly bonded to the second binding moiety through a variety of suitable linkages. For example, when the first binding moiety and the second binding moiety are both proteins or peptides, the moieties can be part of a contiguous polypeptide (i.e., a fusion protein). Where the targeting molecule is a fusion protein, the first and second binding moieties can be arranged on the polypeptide in any suitable configuration. The first and second binding moieties can be indirectly bonded through a (i.e., one or more) peptide linker, or bonded directly to each other through a peptide bond. For example, when the targeting molecule comprises an Fv and a Bonzo ligand, the amino acid sequence of the ligand can be fused to the amino-terminus or the carboxyl terminus of the Fv. The sequence encoding the ligand can also serve as a spacer or be inserted into a spacer which connects the variable regions (heavy chain variable region, light chain variable region) of the Fv.

Where the binding moieties are not part of a contiguous polypeptide they can be directly bonded by a chemical bond formed by reaction of a functional group (or activated derivative thereof) on the first moiety with a second functional group (or activated derivative thereof) on the second moiety. For example, two thiols can react to form a disulfide bond and an amine can react with a carboxylic acid or acyl halide to form an amide. A variety of other suitable reactions which can be used are known in the art (see, for example, Hermanson, G. T., *Bioconjugate Techniques,* Academic Press: San Diego, Calif. (1996)). The binding moieties can be indirectly bonded through a suitable linker (e.g., a peptide linker). Generally, a linker contains two reactive groups which can react to form bonds with the first binding moiety and/or the second binding moiety. Linkers which contain two different reactive groups (e.g., a heterobifunctional linker) can be used to selectively conjugate the first binding moiety to the second binding moiety. Many linkers which are suitable for forming conjugates between proteins, nucleic acids, peptides, vitamins, sugars, lipids, small organic molecules and other suitable agents are known (see, for example, U.S. Pat. Nos. 5,856,571, 5,880,270; Hermanson, G. T., *Bioconjugate Techniques,* Academic Press: San Diego, Calif. (1996)).

Preferably, the independent activities of the binding moieties (e.g., binding activities, chemoattractant activity) of the targeting molecule are not significantly different from the activities of the binding moieties as separate molecular entities. For example, where the first binding moiety is an antibody or antigen-binding fragment that binds Bonzo, the targeting molecule can bind to Bonzo with an affinity which is within a factor of about 1000, preferably within a factor of 100, more preferably within a factor of 10 or substantially the same as the affinity of the free antibody or antigen-binding fragment. Similarly, where the first binding moiety is a Bonzo ligand (e.g., human SExCkine, human platelet factor 4), the targeting molecule can induce chemotaxis of Bonzo$^+$ cells (e.g., Bonzo/L1.2 cells) with an effective dose 50 ($EC_{50}$) that is within a factor of about 1000, preferably within a factor of 100, more preferably within a factor of 10 or substantially the same as the $EC_{50}$ of the free ligand (e.g. human SExCkine, human platelet factor 4). Target molecules with these preferred characteristics can be prepared using any suitable method. For example, a variety of linkers of differing length and with different reactive groups can be bonded to mammalian SExCkine and the resulting products can be assayed in a chemotaxis assay as described herein. Compounds which display a suitable amount of chemoattractant activity can then be reacted with, for example, an antibody or antigen-binding fragment thereof which binds a tumor antigen (e.g., HER-2/neu). The resulting targeting molecule can then be assayed for binding to tumor antigen (e.g., by ELISA) and for chemoattractant activity. In one embodiment, the targeting molecule is a bispecific antibody or bispecific antigen-binding fragment thereof (e.g., F(ab')$_2$) which has specificity for mammalian Bonzo and a molecule expressed on a target cell (e.g., tumor antigen, viral antigen).

In another embodiment, the targeting molecule is an immunoconjugate wherein a Bonzo ligand (e.g., mammalian SExCkine, mammalian platelet factor 4) or receptor-binding variant thereof is bonded to an antibody or antigen-binding fragment thereof which binds to a target cell (e.g., a tumor antigen expressed on target cell, a viral antigen expressed on target cell) through a linker. The linker can form a bond with specific sites on the antibody and/or ligand, for example, the linker can be bonded to the side chain of cysteinyl residues, the side chain of lysine residues, the side chains of aspartyl or glutamyl residues.

In another embodiment, the targeting molecule is a fusion protein comprising a Bonzo ligand (e.g., mammalian SExCkine, mammalian platelet factor 4) or receptor-binding variant thereof and an antibody or antigen-binding fragment thereof (e.g., Fab, Fab', F(ab)'$_2$, Fv) which binds to a target cell (e.g., a tumor antigen expressed on target cell, a viral antigen expressed on target cell). Preferably, the Bonzo ligand is the extracellular region of mammalian SExCkine (e.g., human SExCkine) or a receptor-binding variant thereof. Several suitable methods for preparing fusion proteins are known in the art, for example, the fusion protein can be prepared using the methods described in U.S. Pat. Nos. 5,767,260, 5,824,782 and 5,889,157, or other suitable methods. The entire teachings of U.S. Pat. Nos. 5,767,260, 5,824,782 and 5,889,157 are incorporated herein by reference.

In one embodiment, the targeting molecule is a fusion protein comprising a first moiety which shares at least about 85% sequence similarity with a corresponding portion of a naturally occurring mammalian Bonzo ligand (e.g., human SExCkine (e.g., SEQ ID NO:4, SEQ ID NO:6), human platelet factor four (e.g., amino acid residues 32–100 of SEQ ID NO:8)), preferably at least about 90% sequence similarity, and more preferably at least about 95% sequence similarity with a corresponding portion of a naturally occurring mammalian Bonzo ligand. Amino acid sequence similarity can be identified using a suitable sequence alignment algorithm, such as the Lasergene system (DNASTAR, Inc., Madison, Wis.), as described herein. Variants can be prepared using any suitable methods, (e.g., solid phase peptide synthesis, by expression of nucleic acids encoding the variant), and tested for receptor binding.

Nucleic Acids, Constructs and Vectors

The invention also relates to isolated and/or recombinant nucleic acids which encode a targeting molecule of the invention. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid encodes a fusion protein wherein a Bonzo ligand (e.g., mammalian SExCkine, mammalian platelet factor 4) or a receptor-binding variant thereof is bonded (directly or through a peptide linker) to an antibody or antigen-binding fragment thereof which binds target cell. Preferably, the nucleic acid encodes a fusion protein wherein the extracellular domain of human SExCkine or a receptor-binding variant thereof is bonded (directly or through a peptide linker) to an antibody or antigen-binding fragment thereof which binds a tumor antigen expressed on the surface of a human cell or a viral antigen expressed on the surface of a human cell.

The invention also relates to recombinant cells which can produce a targeting molecule (e.g., fusion protein). Recombinant cells can be produced using a variety of suitable methods. For example, a nucleic acid encoding all or part of the coding sequence for the desired fusion protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome. Suitable expression vectors for the expression of a nucleic acid encoding all or part of the coding sequence of the desired fusion protein are also available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for targeting to the secretory pathway in a selected host cell (e.g., of mammalian origin or from a heterologous mammalian or non-mammalian species). In a construct, a signal sequence can be provided by the vector, the insert nucleic acid, or other source. Sequences present at a site of integration can also provide these elements.

A promoter can be provided for expression in a suitable host cell. Promoters can be constitutive or inducible. For example, a promoter can be operably linked to a nucleic acid encoding the fusion protein, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

The invention also relates to a method of producing a targeting molecule. For example, a nucleic acid encoding a targeting molecule fusion protein, or a construct comprising such nucleic acid, can be introduced into a suitable host cell by a method appropriate to the host cell selected (e.g., transformation, transfection, electroporation, infection), such that the nucleic acid is operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded targeting molecule can be isolated (e.g., from the host cells, medium, milk). It will be appreciated that the method encompasses expression in a host cell of a transgenic animal (see e.g., WO 92/03918, GenPharm International, published Mar. 19, 1992).

Models of Inflammation

In vivo models of inflammation are available which can be used to assess the efficacy of antibodies (anti-Bonzo, anti-SExCkine), antigen-binding fragments and targeting molecules of the invention, as well as agents identified by the methods described herein as in vivo therapeutics. For example, leukocyte infiltration upon intradermal injection of a Bonzo ligand (e.g., SExCkine, platelet factor 4) and an antibody or antigen-binding fragment thereof reactive with mammalian Bonzo into a suitable animal, such as rabbit, mouse, rat, guinea pig or primate (e.g., rhesus macaque) can be monitored (see e.g., Van Damme, J. et al., *J. Exp. Med.,* 176: 59–65 (1992); Zachariae, C. O. C. et al., *J. Exp. Med.* 171: 2177–2182 (1990); Jose, P. J. et al., *J. Exp. Med.* 179. 881–887 (1994)). In one embodiment, skin biopsies are assessed histologically for infiltration of leukocytes (e.g., Bonzo$^+$ T cells). In another embodiment, labeled cells (e.g., stably transfected cells expressing a mammalian Bonzo, labeled with $^{111}$In for example) capable of chemotaxis and extravasation are administered to the animal. For example, an antibody or agent to be assessed which binds a mammalian Bonzo can be administered, either before, simultaneously with or after a Bonzo ligand or agonist (e.g., SexCkine) is administered to the test animal. A decrease of the extent of infiltration in the presence of antibody or agent as compared with the extent of infiltration in the absence of said antibody or agent is indicative of inhibition.

As described herein, Bonzo is expressed on chronically stimulated lymphocytes (e.g., chronically stimulated T cell subsets (e.g., $T_H1$, $T_H2$, $T_R1$, LAK, CIK). Thus, animal models of inflammatory diseases can be used to assess the therapeutic efficacy of Bonzo modulating agents. A variety of in vivo models of inflammatory diseases are available, which can be used to assess the effects of ligands, inhibitors, promoters or targeting molecules in vivo as therapeutic agents, including a sheep model for asthma (see e.g., Weg, V. B. et al., *J. Exp. Med.,* 177: 561 (1993), the teachings of which are incorporated herein by reference), a rat delayed type hypersensitivity model (Rand, M. L. et al., *Am. J. Pathol.,* 148: 855–864 (1996), the teachings of which are incorporated herein by reference), or other suitable models. Additional suitable models include, models of mucosal inflammatory diseases (e.g., respiratory tract, urogenital tract, alimentary canal and associated organs and tissues (e.g., pancreas, liver, gall bladder)). For example, the antibodies and antigen binding fragments of the invention, as well as agents identified by the methods described herein, can be studied in the cotton-top tamarin model of inflammatory bowel disease (Podolsky, D. K., et al., *J. Clin. Invest.* 92:372–380 (1993)). The CD45RB$^{Hi}$/SCID model provides a mouse model with similarity to both Crohn's disease and ulcerative colitis (Powrie, F. et al., *Immunity,* 1:553–562 (1994)). Therapeutic efficacy in this model can be assessed, for example, by using parameters such as inhibition of recruitment of $^{111}$In-labeled cells to the colon and reduction in the number of CD4$^+$ T lymphocytes in the lamina propria of the large intestine after administration (e.g., intravenous (i.v.), intraperitoneally (i.p.) and per oral (p.o.)) of an agent. Knockout mice which develop intestinal lesions similar to those of human inflammatory bowel disease have also been described (Strober, W. and Ehrhardt, R. O., *Cell,* 75: 203–205 (1993)), and NOD mice provide an animal model of insulin-dependent diabetes mellitus.

Well established animal models for multiple sclerosis (e.g., experimental autoimmune encephalitis in rodents (e.g., mice, rats)), cancers and infectious diseases which can be used to assess the therapeutic efficacy of targeting molecules and Bonzo modulating agents are available. For example, anti-tumor activity of targeting molecules and Bonzo agonists can be evaluated in MCA26 colon carcinoma liver tumor model, in SCID mice injected with human gastric tumor cell line MKN-45, in mice (C3H/HeN) injected with CL-62 melanoma cells, mice injected with HOPE2 metastatic melanoma cells or other suitable models (see, for example, Pham-Nguyen, K. B., et al., *Int. J. Cancer,* 81:813–819 (1999); Senba, T., et al., *Anticancer Res.,* 18:17–24 (1998), Thibault, C., et al., *Int. J. Cancer,* 67:232–237 (1996), Hariharan, K., et al., *Int. J. Oncol.,* 12:1229–1235 (1998)). Animal models which closely resemble human disease, such as viral infection (HIV, EBV, hepatitis C virus) and cancer (e.g., lymphoid tumors) in SCID-hu mice can be used (see, for example, Seydel K. B. et al., *Gastroenterology,* 115:1446–1453 (1998), Bristol, G. C. et al., *Methods,* 12:343–347 (1997), Jansen, B. et al., *Int. J. Cancer,* 67:821–825 (1996), McCune, J. M., et al., *Curr. Top. Microbiol. Immunol.,* 152:183–193 (1989)).

Diagnostic Applications

The Bonzo binding agents described herein (e.g., antibodies of the present invention, SExCkine) have application in procedures in which Bonzo can be detected on the surface of cells. The receptor provides a marker of the leukocyte cell types in which it is expressed. For example, antibodies raised against a mammalian Bonzo protein or peptide, such as the anti-Bonzo antibodies described herein (e.g., mAb 4A11, mAb 7A2, mAb 7F3, mAb 9G2), can be used to detect and/or quantify cells expressing a mammalian Bonzo. In one embodiment, the antibodies can be used to sort cells which express Bonzo from among a mixture of cells (e.g., to isolate cytotoxic "anti-tumor" cells, such as Bonzo$^+$CD3$^+$ CD56$^+$ T cells). Suitable methods for counting and/or sorting cells can be used for this purpose (e.g., flow cytometry, fluorescence activated cell sorting). If desired, sorted cells can be expanded by culture under conditions suitable for expansion of cytotoxic effector cell. Culture conditions which are suitable for expanding cytotoxic effector cells, including CD3$^+$CD56$^+$ cells, are known in the art (see, for example, Lu, P. H. et al., *J. Immunol.,* 153:1687–1696 (1994); Jin, Y. et al., *Human Immunology,* 59:352–362 (1998)). In another embodiment, Bonzo$^+$ cells are identified by the ability to bind SExCkine or a receptor-binding variant thereof. Cell counts can be used in the diagnosis of diseases or conditions in which an increase or decrease in leukocyte cell types (e.g., leukocytes which home to the mucosa) is observed.

Furthermore, Bonzo binding agents described herein (e.g., antibodies of the present invention, SExCkine) can be used to detect or measure expression of Bonzo. For example, antibodies of the present invention can be used to detect or measure a mammalian Bonzo in a biological sample (e.g., cells, tissues or body fluids from an individual such as blood, serum, leukocytes (e.g., activated T lymphocytes), bronchoalveolar lavage fluid, saliva, bowel fluid, biopsy specimens). For example, a sample (e.g., tissue and/or fluid) can be obtained from an individual and a suitable assay can be used to assess the presence or amount of Bonzo protein. Suitable assays include immunological and immunochemical methods such as flow cytometry (e.g., FACS analysis) and immunosorbent assays, including enzyme-linked immunosorbent assays (ELISA), radioimmunoassay (RIA), chemiluminescence assays, immuno-blot (e.g., western blot), immunocytochemistry and immunohistology. Generally, a sample and antibody or antigen-binding fragment of the present invention are combined under conditions suitable for the formation a complex between Bonzo and the antibody or antigen-binding fragment thereof, and the formation of said complex is assessed (directly or indirectly).

The presence of an increased level of Bonzo reactivity in a sample (e.g., a tissue sample) obtained from an individual can be indicative of inflammation and/or leukocyte (e.g., activated T cell) infiltration and/or accumulation associated with an inflammatory disease or condition, such as an inflammatory bowel disease, allograft rejection, delayed type hypersensitivity reaction, or an infection such as a viral or bacterial infection. The presence of a decreased level of Bonzo reactivity in the circulation (e.g., on the surface of circulating lymphocytes) can also be indicative of leukocyte infiltration and/or accumulation at inflammatory sites. The level of expression of a mammalian Bonzo protein or variant can also be used to correlate increased or decreased expression of a mammalian Bonzo protein with a particular disease or condition, and in the diagnosis of a disease or condition in which increased or decreased expression of a mammalian Bonzo protein occurs (e.g., increased or decreased relative to a suitable control, such as the level of expression in a normal individual). Similarly, the course of therapy can be monitored by assessing Bonzo immunoreactivity in a sample from a subject. For example, antibodies of the present invention can be used to monitor the number of cells expressing Bonzo in a sample (e.g., blood, tissue) from a subject being treated with an anti-inflammatory or immunomodulating agent (e.g., immunosuppressive agent, such as cyclosporin A; immunostimulant, such as IL-2).

Kits for use in detecting the presence of a mammalian Bonzo protein in a biological sample can also be prepared. Such kits can include an agent which binds to a mammalian Bonzo receptor or portion of said receptor (e.g.,antibody or functional fragment thereof, ligand (e.g., SExCkine)), as well as one or more ancillary reagents suitable for detecting the presence of a complex between the antibody or fragment and Bonzo or portion thereof. The antibody compositions of the present invention can be provided in lyophilized form, either alone or in combination with additional antibodies specific for other epitopes. The antibodies or antigen-binding fragments thereof, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-Bonzo antibody or antigen-binding fragment is employed, such antibody or fragment can be provided in the kit, for instance in a separate vial or container. The second antibody or antigen-binding fragment, if present, is typically labeled, and can be formulated in an analogous manner with the antibody formulations described above. The components (e.g., anti-Bonzo antibody or antigen-binding fragment thereof, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Similarly, the present invention also relates to a method of detecting and/or quantifying expression of a mammalian Bonzo receptor or a portion of the receptor by a cell, in which a composition comprising a cell or fraction thereof (e.g., membrane fraction) is contacted with an antibody or functional fragment thereof (e.g., mAb 4A11, mAb 7A2, mAb 7F3, mAb 9G2) which binds to a mammalian Bonzo or portion of the receptor under conditions appropriate for binding of the antibody or fragment thereto, and binding is monitored. Detection of the antibody or antigen-binding fragment, indicative of the formation of a complex between said antibody or fragment and a mammalian Bonzo or a portion thereof, indicates the presence of the receptor. Binding of antibody to the cell can be determined using any suitable method. The method can be used to detect expression of Bonzo on cells from a subject (e.g., in a sample, such as a body fluid, such as blood, saliva or other suitable sample). The level of expression of Bonzo on the surface of cells (e.g., leukocytes) can also be determined, for instance, by flow cytometry, and the level of expression (e.g., staining intensity) can be correlated with disease susceptibility, progression or risk.

The anti-SExCkine antibodies and antigen-binding fragments thereof described herein have application in procedures in which SExCkine can be detected on the surface of cells or in solution (e.g., in plasma, serum, culture supernatant). The protein provides a marker for cell types in which SExCkine is expressed. For example, antibodies raised against a mammalian SExCkine protein or peptide, can be used to detect and/or quantify cells expressing a mammalian SExCkine. In one embodiment, the antibodies can be used to sort cells which express SExCkine from among a mixture of cells (e.g., cells expressing transmembrane SExCkine, cells expressing intracellular SExCkine). Suitable methods for counting and/or sorting cells can be used for this purpose (e.g., flow cytometry, fluorescence activated cell sorting). If desired, sorted cells can be expanded by culture under conditions suitable for expansion. Cell counts can be used in the diagnosis of diseases or conditions in which an increase or decrease in SExCkine expression is observed.

Furthermore, anti-SExCkine antibodies and antigen-binding fragments thereof described herein can be used to detect or measure expression of SExCkine. For example, antibodies of the present invention can be used to detect or measure a mammalian SExCkine in a biological sample (e.g., cells, tissues or body fluids from an individual such as blood, serum, leukocytes (e.g., activated T lymphocytes), bronchoalveolar lavage fluid, saliva, bowel fluid, biopsy specimens). For example, a sample (e.g., tissue and/or fluid) can be obtained from an individual and a suitable assay can be used to assess the presence or amount of SExCkine protein. Suitable assays include immunological and immunochemical methods such as flow cytometry (e.g., FACS analysis) and immunosorbent assays, including enzyme-linked immunosorbent assays (ELISA), radioimmunoassay (RIA), chemiluminescence assays, immuno-blot (e.g., western blot), immunocytochemistry and immunohistology. Generally, a sample and antibody or antigen-binding fragment of the present invention are combined under conditions suitable for the formation of a complex between SExCkine and said antibody or fragment, and the formation of said complex is assessed (directly or indirectly).

The presence of an increased level of SExCkine reactivity in a sample (e.g., blood, serum, tissue) obtained from an individual can be indicative of inflammation and/or leukocyte (e.g., activated T cell) infiltration and/or accumulation associated with an inflammatory disease or condition, such as an inflammatory bowel disease, allograft rejection, delayed type hypersensitivity reaction, or an infection such as a viral or bacterial infection. The level of expression of a mammalian SExCkine protein or variant can also be used to correlate increased or decreased expression of a mammalian SExCkine protein with a particular disease or condition, and in the diagnosis of a disease or condition in which increased or decreased expression of a mammalian SExCkine protein occurs (e.g., increased or decreased relative to a suitable control, such as the level of expression in a normal individual). Similarly, the course of therapy can be monitored by assessing SExCkine immunoreactivity in a sample from a subject. For example, antibodies of the present invention can be used to monitor the amount of SExCkine in a sample (e.g., blood, serum, tissue) from a subject being treated with an anti-inflammatory or immunomodulating agent (e.g., immunosuppressive agent, such as cyclosporin A; immunostimulant, such as IL-2).

Kits for use in detecting the presence of a mammalian SExCkine protein in a biological sample can also be prepared. Such kits can include an antibody or functional fragment thereof which binds to a mammalian SExCkine or portion thereof, as well as one or more ancillary reagents suitable for detecting the presence of a complex between the antibody or fragment and SExCkine or portion thereof. The antibody compositions of the present invention can be provided in lyophilized form, either alone or in combination with additional antibodies specific for other epitopes. The antibodies or antigen-binding fragments, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-SExCkine antibody or antigen-binding fragment is employed, such antibody or fragment can be provided in the kit, for instance in a separate vial or container. The second antibody or antigen-binding fragment, if present, is typically labeled, and can be formulated in an analogous manner with the antibody formulations described above. The components (e.g., anti-SExCkine antibody or antigen-binding fragment thereof, ancillary reagent) of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Similarly, the present invention also relates to a method of detecting and/or quantifying expression of a mammalian SExCkine or a portion thereof by a cell, in which a composition comprising a cell or fraction thereof (e.g., membrane fraction, saponin permeabilized cell) is contacted with an antibody or functional fragment thereof which binds to a mammalian SExCkine or portion thereof under conditions appropriate for binding of the antibody or fragment thereto, and binding is monitored. Detection of the antibody or antigen-binding fragment, indicative of the formation of a complex between said antibody or fragment and a mammalian SExCkine or a portion thereof, indicates the presence of the receptor. Binding of antibody to SExCkine can be determined using any suitable method. The method can be used to detect expression (e.g., on the plasma membrane, intracellular) of SExCkine by cells from a subject (e.g., in a sample, such as a body fluid, such as blood, saliva or other suitable sample). (See, for example, Kallas, E. G., et al., *J. Infect. Dis.*, 179:1124–1131 (1999), regarding intracellular staining of cells to detect secreted proteins.) The level of expression of SExCkine (e.g., staining intensity) can be correlated with disease susceptibility, progression or risk.

Methods of Therapy

Modulation of mammalian Bonzo function according to the present invention, through the inhibition or promotion of at least one function characteristic of a mammalian Bonzo protein, provides an effective and selective way of inhibiting or promoting receptor-mediated functions. Once lymphocytes are recruited to a site, other leukocyte types, such as monocytes, may be recruited by secondary signals. Thus, agents which can modulate Bonzo function, including ligands, inhibitors and/or promoters, such as those identified as described herein, can be used to modulate leukocyte function (e.g., leukocyte infiltration including recruitment and/or accumulation).

In one aspect, the present invention provides a method of modulating (inhibiting or promoting) an inflammatory response in a subject in need of such therapy, comprising administering an effective amount of an agent which inhibits or promotes mammalian Bonzo function to an individual in need of such therapy. In one embodiment, an effective amount of an agent which inhibits one or more functions of a mammalian Bonzo protein (e.g., a human Bonzo) is administered to a subject to inhibit (i.e., reduce or prevent) inflammation. For example, antibodies of the present invention, including antibodies and antigen-binding fragments thereof which bind Bonzo and inhibit binding of ligand to receptor (e.g., mAb 4A11, mAb 7A2, mAb 7F3), and antibodies and antigen-binding fragments thereof which bind SExCkine and inhibit binding of SExCkine to Bonzo, can be used in the method. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a inflamed mucous membrane (e.g., colon, small intestine)) can be inhibited according to the present method. In another embodiment, an effective amount of an agent which inhibits one or more functions of a mammalian Bonzo protein (e.g., a human Bonzo) is administered to a subject to inhibit (i.e., reduce or prevent) Bonzo-mediated homing of leukocytes.

Thus, the invention relates to a method of treating a subject having an inflammatory disease, comprising administering an effective amount of an antagonist of Bonzo function. In a particular embodiment, the subject has an inflammatory bowel disease, such as Crohn's disease or colitis.

The invention also relates to a method of inhibiting Bonzo-mediated homing of leukocytes in a subject, comprising administering an effective amount of an antagonist of Bonzo function, for example, the homing of leukocytes to mucosal sites can be inhibited.

In one embodiment, an agent (e.g., receptor agonist) which promotes one or more functions of a mammalian Bonzo protein (e.g., a human Bonzo) is administered to induce (trigger or enhance) the recruitment of cells to a desired site or to induce an inflammatory response, such as leukocyte emigration, chemotaxis, exocytosis (e.g., of enzymes) or inflammatory mediator release, resulting in the beneficial stimulation of inflammatory processes. For example, T cells including $CD3^+CD56^+$ cells can be recruited to combat infections (e.g., viral, bacterial, fungal) or tumors.

In another embodiment, a targeting molecule, as described herein, is administered to effectuate or promote the interaction of a $Bonzo^+$ cell (e.g., $Bonzo^+$ CIK cell) with a target cell (e.g., a cell infected with a virus, tumor cell). For example, a targeting molecule can be administered to promote the interaction of $Bonzo^+$ cytotoxic/cytolytic cells (e.g., cytotoxic T cells, $CD3^+CD56^+$ cells, NK cells, CIK, LAK) with tumor cells and/or virus infected cells, resulting in the beneficial targeting of cytotoxic/cytolytic activity. Accordingly, a targeting molecule (e.g., a bispecific anti-Bonzo X anti-tumor antigen antibody) can be administered to treat a subject having a tumor or infection (e.g., viral infection). Targeting molecules can also be administered to recruit $Bonzo^+$ cytotoxic/cytolytic cells and/or augment cytotoxic/cytolytic effector function in a subject, for example, as a component of a vaccine.

In a another embodiment, the invention relates to a method of promoting Bonzo mediated homing of leukocytes in a subject, comprising administering an effective amount of a promoter (e.g., agonist) of Bonzo function.

Agents which can inhibit the binding of SExCkine to receptor (e.g., Bonzo), including antibodies, such as those identified as described herein, can be used to modulate leukocyte function (e.g., leukocyte infiltration including recruitment and/or accumulation).

In one aspect, the present invention provides a method of modulating (inhibiting or promoting) an inflammatory response in a subject in need of such therapy, comprising administering an effective amount of an antibody which inhibits binding of SExCkine to receptor (e.g., Bonzo) to an individual in need of such therapy. In one embodiment, an effective amount of an antibody which inhibits binding of mammalian SExCkine to mammalian Bonzo protein (e.g., a human Bonzo) is administered to a subject to inhibit (i.e., reduce or prevent) inflammation. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a inflamed mucus membrane (e.g., colon, small intestine)) can be inhibited according to the present method. In another embodiment, an effective amount of an antibody which inhibits binding of mammalian SExCkine to mammalian Bonzo protein (e.g., a human Bonzo) is administered to a subject to inhibit (i.e., reduce or prevent) SExCkine-induced homing of leukocytes.

In another embodiment, $Bonzo^+$ cells are sorted (e.g., from the peripheral blood isolated from a subject) to prepare a population of cells enriched in cytotoxic effector cells (e.g., $Bonzo^+CD3^+CD56^+$ cells, $Bonzo^+CD56^+NK$ cells). For example, peripheral blood cells can be contacted with an anti-Bonzo antibody under conditions suitable for binding of antibody to Bonzo expressed on the surface of cells. The cells to which the anti-Bonzo antibody is bound can be isolated using any suitable method. For example, direct or indirect fluorescence activated cell sorting or direct or indirect magnetic sorting can be used. The sorted cells can be administered to a subject in need thereof, or the population of sorted cells can be expanded and/or differentiated by culture under suitable conditions. For example, LAK cells or CIK cells can be generated and/or expanded. The expanded cells can also be administered to a subject in need of cytotoxic effector cells (e.g., a subject which has a tumor, a subject which has a viral infection). Preferably, autologous cytotoxic effector cells are administered. Culture conditions which are suitable for expanding cytotoxic effector cells, including $CD3^+CD56^+$cells, CIK and LAK cells, are known in the art (see, for example, Lu, P. H. et al., *J. Immunol.*, 153:1687–1696 (1994); Jin, Y. et al., *Human Immunology*, 59:352–362 (1998)).

The term "subject" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic (including prophylactic) purposes. In a particularly preferred embodiment, the inflammatory disease or condition is a T cell-mediated disease or condition.

Diseases or conditions, including chronic diseases, of humans or other species which can be treated with inhibitors of Bonzo function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, autoimmune thyroiditis, Behcet's disease;

graft rejection (e.g., in transplantation), including allograft rejection or graft-versus-host disease;

viral infection, particularly infection by simian immunodeficiency virus (SIV) or human immunodeficiency virus (HIV);

other diseases or conditions in which undesirable inflammatory responses are to be inhibited can be treated, including, but not limited to, atherosclerosis (e.g., transplant accelerated atherosclerosis), restenosis, cytokine-induced toxicity, myositis (including polymyositis, dermatomyositis).

Diseases or conditions of humans or other species which can be treated with promoters (e.g., an agonist) of Bonzo function or targeting molecules, include, but are not limited to:

cancers, for example, solid tumors and/or those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes.

Modes of Administration

According to the method, one or more agents can be administered to the subject by an appropriate route, either alone or in combination with another drug. An effective amount of an agent (e.g., a molecule which inhibits ligand binding, an anti-Bonzo antibody or antigen-binding fragment thereof, a targeting molecule) is administered. An effective amount is an amount sufficient to achieve the desired therapeutic or prophylactic effect, under the conditions of administration, such as an amount sufficient to promote the interaction of a Bonzo$^+$ cell with a target cell, or an amount sufficient for inhibition or promotion of Bonzo receptor function, and thereby, inhibition or promotion, respectively, of a Bonzo-mediated process (e.g., an inflammatory response). The agents can be administered in a single dose or multiple doses. The dosage can be determined by methods known in the art and is dependent, for example, upon the particular agent chosen, the subject's age, sensitivity and tolerance to drugs, and overall well-being. Suitable dosages for antibodies and targeting molecules can be from about 0.01 mg/kg to about 100 mg/kg body weight per treatment.

A variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (e.g., Bonzo antagonist) chosen, and the particular condition (e.g., disease) being treated, however, oral or parenteral administration is generally preferred.

The agent can be administered as a neutral compound or as a salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent can be administered to the individual as part of a pharmaceutical composition for modulation of Bonzo function comprising an inhibitor or promotor of Bonzo function and a pharmaceutically acceptable carrier. Formulation will vary according to the route of administration selected (e.g., solution, emulsion, capsule). Suitable pharmaceutical carriers can contain inert ingredients which do not interact with the promoter (agonist) or inhibitor (antagonist) of Bonzo function. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The present invention will now be illustrated by the following Examples, which are not intended to be limiting in any way.

EXAMPLE

Methods and Materials

Construction of Recombinant Cells Expressing Bonzo

DNA encoding Bonzo was obtained by polymerase chain reaction (PCR) using human genomic DNA as template with a synthetic 5'-oligonucleotide primer (ttt gga tcc atg tat ccc tat gac gtg ccc gac tat gct gca gag cat gat tac cat gaa gac tat ggg, SEQ ID NO: 9) and a 3'-oligonucleotide primer (ttt gcggccgc cta taa ctg gaa cat gct ggt ggc ctc, SEQ ID NO:10) which contained flanking BamHI and NotI restriction sites, respectively. The 5'-oligonucleotide primer was designed to produce a DNA encoding Bonzo that contains an N-terminal Hemagglutinin (HA) epitope (CYPYDVPDYASL; SEQ ID NO: 11). The PCR contained 0.2 µM primers (total), 0.39 µg human genomic DNA, 0.2 mM dNTPs, 3.75 U PFU polymerase. Cycling parameters were: 95° C. for 5 minutes, followed by 30 cycles of 95° C. for 30 seconds, 55° C. for 1 minute and 72° C. for 1.5 minutes, then 72° C. for 10 minutes. The PCR fragment was subcloned into the BamHI and NotI sites of pCDEF/IRES. pCDEF/IRES was prepared by inserting the MluI-NotI fragment from pCDEF3 (Goldman, L. A., et al., *Biotechniques,* 21:1013–1015 (1996)) into the MluI-NotI sites of pIRESneo (Clontech) which contains a bicistronic fragment to facilitate the selection of high expressors. An EF1 promoter drove expression of the cDNA inserted into pCDEF/IRES. The resulting construct was transfected into the L1.2 cell line (a murine pre-B lymphoma).

The murine pre-B lymphoma cell line L1.2 was obtained from Dr. Eugene Butcher (Stanford University) and maintained in RPMI-1640 supplemented with 10% bovine serum. 20 µg of linearized plasmid was used to transfect the cell line as follows. L1.2 cells were washed twice in HBSS and resuspended in 0.8 ml of the same. The plasmid DNA was mixed with the cells and incubated for 10 minutes at room temperature then transferred to a 0.4 cm electroporation cuvette and a single pulse applied at 250 V, 960 µF. The electroporation was followed by a 10 minute incubation at room temperature. G418 was added to a final concentration of 0.8 mg/ml 48 hr post-transfection and the cells plated in 96 well plates at 25,000 cells/well. After 2–3 weeks under drug selection, cells expressing high levels of Bonzo were selected by staining with anti-HA.11 mAb (Babco, Berkely, Calif.) and subcloned. The resulting stable transfectants were used to immunize mice.

Generation of Anti-Bonzo Hybridomas

MAbs reactive with Bonzo were generated by immunizing mice with Bonzo/L1.2 cells. Six female mice (C57BL6) were immunized by intraperitoneal injection of about $10^7$ cells in phosphate buffered saline. The mice received six injections at three week intervals. The Bonzo/L1.2 cells used for the first 2–3 injections were treated with mitomycin C to prevent tumor growth. A final (seventh) injection was administered intravenously. Four days after the final injection, the animals were sacrificed, the spleens were removed, and splenocytes were fused with SP2/0 cells and selected in media containing hypoxanthine, aminopterine and thymine (HAT media) as described (Coligan, J. E. et al., *Current Protocols in Immunology,* John Wiley and Sons, New York (1992)). About 3000 to about 5000 hybridomas were screened for each fusion. Four hybridomas that secreted anti-Bonzo mAbs were isolated and are presented in Table 1. The hybridomas can be maintained under standard culture conditions (humidified incubator, 37° C., 5% $CO_2$) in the following culture media: Dulbecco's modified Eagle medium (DMEM) containing 10% fetal bovine serum, 2 mM L-glutamine, 1 mM sodium pyruvate and 100 ng/mL interleukin 6. Penicillin (50 U/mL) and streptomycin (50 µg/mL) can be added to the culture media if desired.

TABLE 1

| hybridoma | antibody | isotype | inhibited binding of SExCkine to Bonzo |
|---|---|---|---|
| Murine hybridoma 4A11 | mAb 4A11 | IgG2b | yes |
| Murine hybridoma 7A2 | mAb 7A2 | IgG2a | yes |
| Murine hybridoma 7F3 | mAb 7F3 | IgG2a | yes |
| Murine hybridoma 9G2 | mAb 9G2 | IgM | partial | mAb Specificity and Immunofluorescent Stanining

The reactivity of the mAbs was assessed by staining (indirect immunofluorescence and flow cytometry) human PBMC isolated by Lymphoprep™ (Nycomed) density gradient centrifugation of venous blood collected from volunteer donors, and numerous transfected L1.2 cells that expressed chemokine receptors (CCR1, CCR2, CCR3, CCR4, CCR5, CCR6, CCR7, CCR8, CXCR1, CXCR2, CXCR3, CXCR4, CXCR5, GPR5, V28 and GPR9-6) or orphan G-protein-coupled receptors (Bob, LyGPR, AF014958 (AF, CRAM), APJ and RDC). Nucleotide sequences encoding these receptors are deposited in Genbank under the accession numbers presented in Table 2. For staining, transfected cells or PBMC were washed once with phosphate buffered saline (PBS) and resuspended in PBS containing 5% human serum and 0.1% sodium azide (staining buffer). *Cells were then incubated with* 50 µL of hybridoma culture supernatant or isotype matched control mAbs MOPC 141 (IgG2b), UPC 10 (IgG2a) or TEPC 183 (IgM) (isotype control mAbs were used at 1 µg/mL and were purchased from Sigma Chemical Co., St. Louis, Mo.) for 20 minutes at 4° C. Then, the cells were washed with staining buffer and resuspended in 50 µL FITC-conjugated, affinity purified F(ab')2 goat anti-mouse IgG (Jackson ImmunoResearch Laboratories) diluted 1:200 in staining buffer. The resuspended cells were incubated for 20 minutes at 4° C., and then washed once in staining buffer and analyzed on the FACScan® (Beckton-Dickenson).

TABLE 2

| Receptor | Accession number |
|---|---|
| CCR1 | L09230 |
| CCR2 | U03882 |
| CCR3 | U49727 |
| CCR4 | X85740 |
| CCR5 | X91492 |
| CCR6 | U45984 |
| CCR7 | L31581 |
| CCR8 | U62556 |
| GPR-9-6 (CCR9) | U45982 |
| CXCR1 | M68932 |
| CXCR2 | M73969 |
| CXCR3 | X95876 |
| CXCR4 | A45747 |
| CXCR5 | X68149 |
| Bob (GPR15) | U34806 |
| LyGPR | X98510 |
| AF014958 (CRAM) | AF014958 |
| V28 (Cx3CR1) | U20350 |
| APJ | U03462 |
| GPR5 | P46094 |
| RDC | M64749 |

Chemotaxis Assay

Primary cells (in vitro derived TH cells, LAK cells, CIK cells) or Bonzo/L1.2 cells were used in chemotaxis assays.

Assays Using CIK Cells, TH1 Cells or TH2 Cells

Endothelial cells (ECV 304, American Type Culture Collection, Manassas, Va.) were cultured on 6.5 mm diameter Transwell culture inserts (Costar Corp., Cambridge, Mass.) with 3.0 µm pore size. The culture media consisted of M199+10% FCS, L-glutamine, and antibiotics. The assay media consisted of equal parts RPMI 1640 and M199 with 0.5% BSA. The day before the assay, $2 \times 10^5$ ECV 304 cells were plated onto each insert of the 24 well Transwell chemotaxis plate and the plate was incubated at 37° C. (In some instances, ECV 304 cells were plated on the inserts up to a week before the assay.) SExCkine was added to the 24-well tissue culture plates in a final volume of 600 µL. Endothelial-coated Transwells were then inserted into each well and $10^6$ cells of the leukocyte type being studied were added to the top chamber in a final volume of 100 µL of assay medium. The plate was incubated at 37° C. in 5% $CO_2$/95% air for 1–2 hours. The cells that migrated to the lower chamber were then removed, placed in FACS tubes and counted on a FACScan (Becton-Dickinson) using the acquisition phase at 30 second intervals. Forward angle and side scatter gates were set to exclude debris.

For antibody inhibition studies, the leukocytes being studied were incubated with concentrated hybridoma supernatant containing anti-Bonzo mAbs, purified anti-Bonzo mAbs at varying concentrations or isotype matched control antibodies for about 20 minutes at 37° C. prior to being added to the top chamber of the transwell.

Assays Using Bonzo/L1.2 Cells

Two days prior to the assay, the Bonzo/L1.2 cells were split to a density of $0.3 \times 10^6$/mL. On the day of the assay the transfected Bonzo/L1.2 cells were centrifuged and resuspended at a density of $1 \times 10^7$/mL in an assay buffer which consisted of DMEM supplemented with 10% bovine calf serum. The assay was conducted essentially as described above, except no endothelial cells were used.

Preparation of Chronically Activated $T_H1$ and $T_H2$ Lymphocytes

As previously described (Somasse, T., et al., *J. Exp. Med.*, 184:473–483 (1996)), six-well Falcon plates were coated overnight with 10 μg/ml anti-CD28 and 2 μg/ml OKT3, and then washed twice with PBS. Umbilical cord blood CD4$^+$ lymphocytes (Poietic Systems, German Town, Md.) were cultured at $10^5$–$10^6$ cells/ml in DMEM with 10% FCS and IL-2 (4 ng/ml). IL-12 (5 ng/ml) and anti-IL-4 (1 μg/ml) were used to direct to $T_H1$, while IL-4 (5 ng/ml) and anti-IFN gamma (1 μg/ml) were used to direct to $T_H2$. After 4–5 days, the activated $T_H1$ and $T_H2$ lymphocytes were washed once in DMEM and cultured for 4–7 days in DMEM with 10% FCS and IL-2 (1 ng/ml). Following this, the activated $T_H1$ and $T_H2$ lymphocytes were re-stimulated for 5 days with anti-CD28/OKT3 and cytokines as described above, but with the addition of anti-CD95L (1 μg/ml) to prevent apoptosis. After 4–5 days the $T_H1$ and $T_H2$ lymphocytes were washed and then cultured again with IL-2 for 4 days. Activated $T_H1$ and $T_H2$ lymphocytes were maintained in this way for a maximum of three cycles.

Preparation of CD3 Blasts

CD3 blasts were generated using anti-CD3 antibody (OKT3, Pharmingen) and maintained in medium supplemented with recombinant human IL-2 as described (Wu, L., et al., *J. Exp. Med.*, 185:1681–1692 (1997)). Briefly, $2 \times 10^6$ PBMC/mL in RPMI-1640 plus 10% FCS were added to tissue culture plates coated with OKT3 (5 μg/mL). After 4–6 days of culture, blasts were removed to fresh media supplemented with recombinant human IL-2 (100 U/mL, Hoffman-LaRoche, Nutley, N.J.).

Preparation of LAK and CIK Cells

PBMC were resuspended in complete RPMI (cRPMI) containing 10% FCS (Hyclone Labs, Logan, Utah), penicillin (50 U/mL), streptomycin (50 μg/mL), L-glutamine (2 mM ), 2-mercaptoethanol (50 μM). Adherent cells were removed by to two rounds of adherence to plastic at 37° C. LAK cells were prepared by culturing the resulting non-adherent cells in cRPMI supplemented with IL-2 (5 ng/mL) for 3–6 days. CIK cells were prepared by culturing the resulting non-adherent cells in cRPMI supplemented with IFNγ (1000 U/mL) for 24 hours. Then, IL-2 (final concentration 5 ng/mL) and anti-CD3 mAb OKT3 (final concentration 25 ng/mL) were added, and the cells were cultured for an additional 2–3 weeks. The resulting CIK cells were subcultured every 3 days in fresh cRPMI supplemented with IL-2 (5 ng/mL).

Preparation of TR1 Cells

TR1 cells were prepared by stimulating umbilical cord blood CD4$^+$ lymphocytes in the presence of IL-10. (See, for example, Groux, et al., *Nature*, 389:737–742 (1997))

Northern Blot Analysis

Human multiple tissue northern blots I and II and a cancer cell line blot (Clontech) were used to analyzed expression of the gene encoding the Bonzo ligand. cDNA probes were labeled with $\alpha^{32}$P-dCTP by priming with random hexamers. A 400 bp fragment representing most of the chemokine domain of SExCkine cDNA cloned in pCDEF3 (from the 5' EcoR1 site (within vector pCDEF3) to an EcoRV site of a cDNA encoding human SExCkine (SEQ ID NO:3)) was used as the hybridization probe for all blots. Hybridization was performed at 68° C. for 1 hour in ExpressHyb (Clontech) with denatured probe at a concentration of $1 \times 10^6$ CPM/mL. Blots were then washed for 20 minutes in 2×SSC/ 0.05% SDS at room temperature followed by high stringency washes at 50° C., 60° C., or 65° C. in 0.1×SSC/0.1% SDS for 20 minutes per wash and exposed to Kodak XAR film with an intensifying screen.

Construction of Recombinant SExCkine His Tagged and Alkaline Phosphatase Expression Plasmids Fusion proteins consisting of amino terminal regions of SExCkine fused to a C-terminal Histadine (His) were made in pEF-His or pEF1/V5-His A from Invitrogen (Carlsbad, Calif.) and fusion proteins consisting of N-terminal SExCkine regions fused to human alkaline phosphates with a C-terminal His tag were made in the pDERF-SEAP vector (Yoshie, O., et al.,. *J. Leukoc. Biol.*, 62(5):634–644 (1997)).

The alkaline phosphates fusion was produced by amplifying human SExCkine cDNA (SEQ ID NO:3) by PCR using a 5' synthetic oligonucleotide primer that contained a SalI site (5' cgcgtcgacagccgagatgggacgggacttg3', SEQ ID NO:12) and a 3' synthetic oligonucleotide primer that contained a XbaI site (5' ggtctagatgtcctggctgtgggacca3', SEQ ID NO:13). The 5' primer (SEQ ID NO:12) annealed to nucleotides 15–29 of SEQ ID NO:3 and encodes a protein beginning at the initiating Met (amino acid residue 1 of SEQ ID NO:4) and the 3' primer (SEQ ID NO:13) annealed to nucleotides 602–622 of SEQ ID NO:3. The PCR was run for 30 cycles (95° C. (30 seconds), 55° C. (30 seconds), 72° C. (1 minute)).

Similarly, a region encoding the entire extracellular domain of SExCkine was made by PCR using a synthetic 5' primer that contained a BamHI site (5' gag gat cca tgg gac ggg act tg3', SEQ ID NO:14) and a synthetic 3' primer that contained an XbaI site (5' cct cta gat gat gtc ctg gct gtg gga c3', SEQ ID NO:15). The 5' primer (SEQ ID NO:14) annealed to nucleotides 15–29 of SEQ ID NO:3 and encodes a protein beginning at the initiating Met (amino acid residue 1 of SEQ ID NO:4) and the 3' primer (SEQ ID NO:15) annealed to nucleotides 604–622 of SEQ ID NO:3. The DNA product was subcloned into the pEF-His vector as described below.

Additional constructs encoding fragments of the extracellular domain of SexCkine were made by PCR using a 5' primer (SEQ ID NO:14) and synthetic primer KHLL 3' (5' ggt cta gaa agt aaa tgc ttc tgg tgg gc 3', SEQ ID NO:16) or synthetic primer LMS 3' (5' cct cta gag ctc atc aat tcc tga acc c 3', SEQ ID NO:17) or synthetic primer 155 3' (5' ggt cta gac tgg gag ggt ggg gcg ctg ag 3', SEQ ID NO:18). Primer KHLL 3' annealed to nucleotides 345–364 of SEQ ID NO:3, and the product of the amplification reaction encoded residues 1 to 117 of SexCkine (SEQ ID NO:4). Primer LMS 3' annealed to nucleotides 280–300 of SEQ ID NO:3, and the product of the amplification reaction encoded residues 1 to 95 of SexCkine (SEQ ID NO:4). Primer 155 3' annealed to nucleotides 457–477 of SEQ ID NO:3, and the product of the amplification reaction encoded residues 1 to 155 of SExCkine (SEQ ID NO:4). Primers KHLL 3', LMS 3' and 155 3' each contained an XbaI restriction site.

The PCR inserts were purified (Qiagen PCR purification kit), run on a 1% agarose gel and the fragment sizes were confirmed next to a 1 kb ladder. The PCR inserts and vectors (pDREF-SEAP, pEF-His, pEF1/V5-His A) were cut with the appropriate enzymes (SalI and XbaI, BamHI and XbaI). The inserts were ligated to the appropriate vector using 25 ng cut vector, 75 ng cut insert, 2 μL ligase buffer, 1 μL ligase and 5 μL H$_2$O for a final volume of 10 μL. The ligation reaction was incubated at 15° C. overnight (about 14 hours). The ligation was transformed into DH10B cells which were plated on selective media (LB amp). Plasmids were purified from transformants and constructs containing the inserted PCR fragment were identified by restriction analysis.

Transfection and Assays of Recombinant SExCkine Proteins

Thirty 10 cm plates (Beckton Dickinson) were seeded with 1×10$^6$ 293T cells in DMEM+10% FCS. The next day the 293T cells were transfected by adding 10 μg SExCkine/SEAP DNA to 790 μL opti-MEM (800 μL total) and mixing it with a solution of 60 μL LiptofectAMINE™ 2000 in 740 μL opti-MEM (800 μL total). The mixture was incubated at room temperature for 30 min, an additional 6.4 mL of opti-MEM was added to the mixture, and the mixture was added to the plates containing 293T cells with. The plates were incubated at 37° C. for 3 hours, then 8.0 mL DMEM+20% FCS was added. 24 hours later the transfection mixture was removed, the plates were washed with 1×PBS, and 10 μL of serum free DMEM were added. The Plates were then incubated for 3 days. The media (culture supernatant) was removed and filtered (500 mL filter bottle) to remove cellular debris. The harvested media was assayed for chemotactic activity using Bonzo/L1.2 cells essentially as described above. In addition, dilution curves were generated using supernatant diluted in media in a range of undiluted to 1:16 to assess general activity.

Purification of Recombinant SExCkine-Alkaline Phosphatase Fusion Protein

A 0.79 cm$^2$×5 cm column (Biorad, Hercules, Calif.) was packed with 1 mL of anti-alkaline phosphatase agarose (Sigma #A2080). The agarose was washed with 10 mL 1×PBS and the protein eluted with 10 μL 50 mM sodium citrate, pH 3.2 (elution buffer was allowed to settle at the bottom of the column for 1 hour before elution). 10×1 mL elution fraction were collected and the protein concentration of each was determined by the Bradford assay (10 μL of each elution assayed). 50 μL of Tris base (pH 10.8) was added to each elution to neutralize the elution buffer. Elution fractions containing the fusion protein were identified by Western blot (4–20% Tris glycine gel, blocked with 5% milk) using an anti-His antibody (Qiagen).

Alkaline phosphatase activity in the elution fractions was determined by spotting a nitrocellulose blot with 5 μL of elution fractions 1 and 2, 5 μl Tris buffer as a negative control, and 5 μL original culture supernatant as a positive control. The blot was blocked for 2 hours in 5% milk and developed using an alkaline phosphatase detection kit (10 mL buffer, 100 μL reagent A, 100 μL reagent B; BioRad).

Chemotactic activity was determined as described using 1×10$^6$ transfected L1.2 expressing Bonzo and 0.5 nM, 5 nM, and 25 nM purified SExCkine/SEAP (concentrations based on results of Bradford assay).

Results and Discussion

Figure 3:
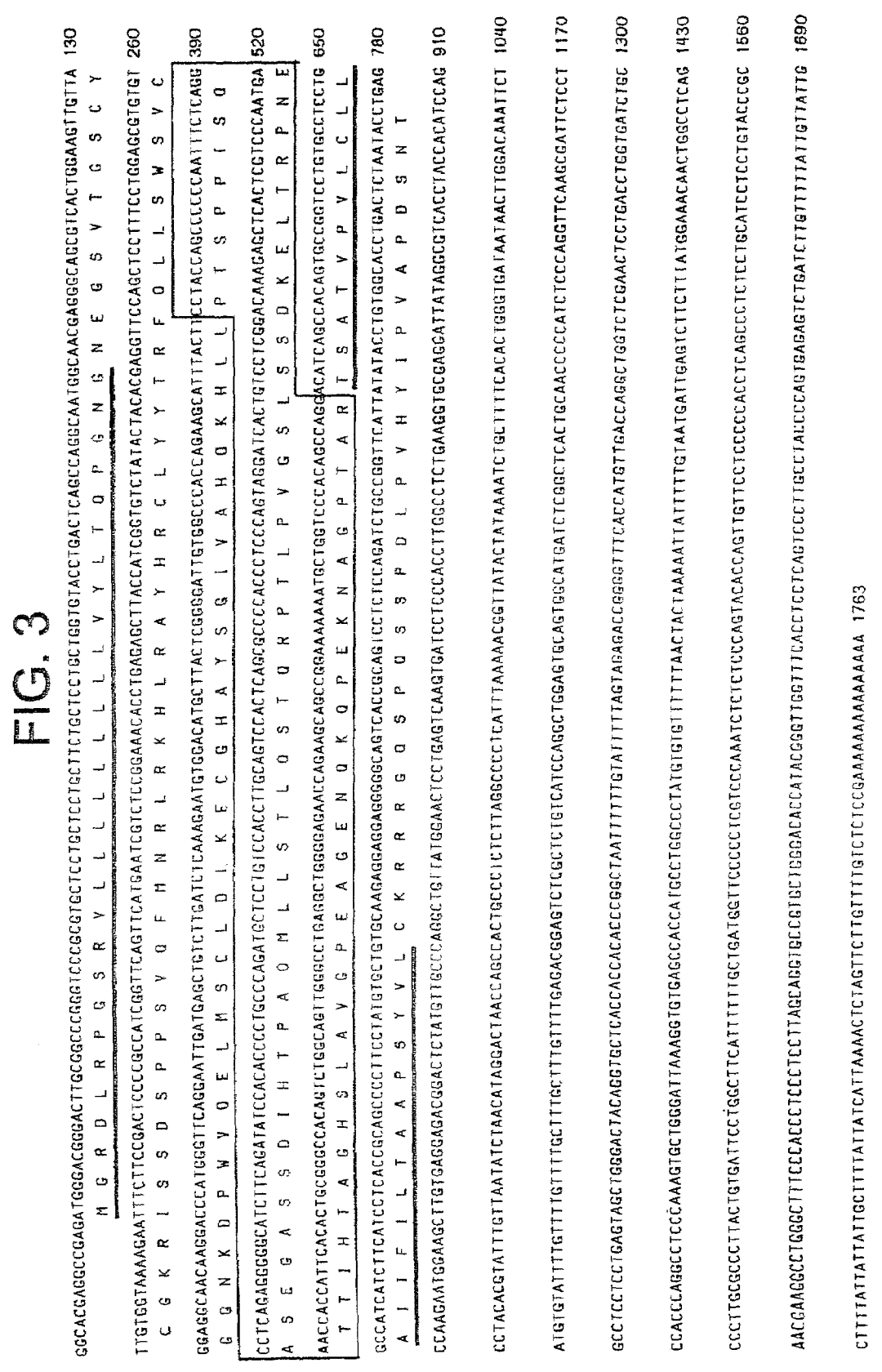

During the course of this study a natural ligand for Bonzo, that induced chemotaxis of Bonzo/L1.2 cells, was identified. This ligand is referred to herein as SExCkine (Spleen Extracted Chemokine, SEQ ID NO:4). SExCkine is a CXC chemokine based upon the positions of conserved cysteine residues. However, the SExCkine protein includes an N-terminal chemokine domain, a membrane-proximal mucin domain, a transmembrane region and a cytoplasmic tail (FIG. 3, FIG. 30). Thus, SExCkine is structurally similar to the CX3C chemokine fractalkine (Bazan, J. F., et al., Nature 385(6617):640–644 (1997)). The primary structure indicates that SExCkine can be expressed on the cell membrane (as an integral membrane protein). Chemoattractant activity was found in the supernatant of 293T cells transfected with a cDNA (SEQ ID NO:3) encoding the fall length protein (FIG. 7). Thus, at least some SExCkine is processed (e.g., by cleavage) to form a soluble chemokine.

Multiple transcripts which hybridized with a SExCkine cDNA probe were detected in many tissues, including, spleen, thymus, prostate, testis, ovary, small intestine, colon, peripheral blood leukocytes, pancreas, kidney, liver, lung, placenta, brain and heart, and several cancer cell lines, including melanoma, lung carcinoma, colorectal adenocarcinoma, Burkitt's Lymphoma, lymphoblastic leukemia, Hela cells and promelocytic leukemia HL60, by Northern blot analysis. High expression of a 1.8 kb transcript which corresponds in size to isolated cDNA encoding human SExCkine (SEQ ID NO:3) was seen in spleen, peripheral blood leukocytes, prostate, testis and ovary. The nature of other hybridizing transcripts, which can be partially processed molecules or molecules with a similar nucleotide sequence, is under investigation.

A panel of antibodies which bind human Bonzo were produced by immunizing mice with transfected L1.2 cells that expressed high levels of Bonzo. The antibodies specifically bound to Bonzo expressed on the surface of Bonzo/L1.2 cells (FIGS. 8A–8D) but did not bind to transfected L1.2 cells which expressed CCR1, CCR2, CCR3, CCR4, CCR5, CCR6, CCR7, CCR8, CXCR1, CXCR2, CXCR3, CXCR4, CXCR5, GPR5, V28, GPR9-6, Bob, LyGPR, AF, APJ or RDC (FIGS. 9A–9G). The antibodies, (e.g., mAbs 4A11, 7A2 and 7F3) inhibited the binding of SExCkine to Bonzo (FIG. 10, FIG. 31, Table 1). Staining studies revealed that Bonzo is expressed on small populations of CD4$^+$ and CD8$^+$ T cells as well as on CD16$^+$/CD56$^+$ NK cells. However, no expression of Bonzo was observed on CD19$^+$/CD20$^+$ B cells or on CD14$^+$ monocytes (FIGS. 11A–11H). Multi-color staining studies were performed to analyzed the co-expression of Bonzo and other cell surface proteins (FIGS. 12A–12D, 13A–13J, 14A–14H, 15A–15C, 16A–16D). These studies revealed that Bonzo is expressed predominantly on CD45RO$^{hi}$ memory lymphocytes. Furthermore, Bonzo expression was detected on both skin homing (CLA$^+$) and gut homing α4β7$^+$ and αE$^+$) CD4$^+$ lymphocytes (FIGS. 12A–12D). Bonzo was co-expressed with CCR1, CCR2, CCR5, CCR6, CXCR1, CXCR2 or CXCR3 on lymphocytes (FIGS. 13A–13J).

Bonzo expression was detected on the surface of a rare population of potent "anti-tumor" cytotoxic effector cells which are CD3$^+$CD56$^+$CD8$^+$ (FIGS. 16A–16D). These cells include lymphokine activated killer cells (LAK) and cytokine-induced killer cells (CIK). Chemotaxis of both LAK (FIG. 18) and CIK (FIG. 21) cells was induced by SExCkine, and in the case of CIK cells, the chemotaxis was completely inhibited by mAb 7F3 (FIG. 21). Further studies revealed that Bonzo is expressed on other subsets of chronically activated lymphocytes. In fact, staining of CD3 blasts was characterized by an increase in cell surface Bonzo expression over time (FIG. 22). Similar activation-induced expression was observed on in vitro derived TH1, TH2 and TR1 lymphocytes (FIGS. 24B and 24E, 25B and 25E, 26B and 26E). The increase in Bonzo expression on these in vitro derived cells paralelled their ability to chemotax to conditioned supernatant from SExCkine transfected 293T cells (FIGS. 27 and 28). Furthermore, SExCkine-induced chemotaxis of in vitro derived TH2 cells was inhibited by the anti-Bonzo mAb 7F3 (FIG. 28).

Recombinant proteins consisting of the entire extracellular domain (or fragments thereof) of SExCkine fused to either a C-terminal His tag or to human placental alkaline phosphatase (i.e., carboxyl terminal residue of SExCkine moiety bonded to amino terminal residue of alkaline phosphatase moiety) were produced. One of the proteins contained the entire predicted extracellular domain of SExCkine (truncated after T202) fused to alkaline phosphates (pDEF SExCkine/SEAP), others consisted of the extracellular domain of SExCkine truncated in the middle of the mucin domain (after V155) and cloned into vector pEF or pCDEF3. These proteins were produced by transient expression in 293T cells and tested for chemoattractant activity in chemotaxis assays. The chemoattractant activity of the truncated recombinant proteins was about equivalent to that of SExCkine produced by expression of the full length cDNA (SEQ ID NO:3) (FIG. 29).

In a further study, a synthetic peptide consisting of amino acid residues 30 (Asn) to 95 (Ser) of SExCkine (SEQ ID NO:4) was produced. This peptide also induced chemotaxis of Bonzo/L1.2 cells. These data demonstrate that fragments of the amino terminal region of SExCkine (e.g., peptides derived from the extracellular domaine of SExCkine (SEQ ID NO:4)) can bind Bonzo and induce chemotaxis of Bonzo$^+$ cells.

This study demonstrates that recombinant SExCkine and recombinant proteins encoding parts of the amino terminal portion of SExCkine can be used in conjunction with Bonzo (e.g., a cell expression Bonzo) in receptor binding assays and functional assays to screen for potential agonists and antagonists of Bonzo. Considering that Bonzo is highly expressed on all classes of chronically stimulated T cell subsets, antagonists of the receptor (e.g., mAbs 4A11, 7A2 and 7F3) can be administered to treat chronic inflammatory diseases. Furthermore, agonists of Bonzo (e.g., SExCkine) can be administered to recruit killer T cell subsets to, for example, solid tumors or sites of infection.

While this invention has been particularly shown and described with references to preferred embodiments thereof, it will be understood by those skilled in the art that various changes in form and details may be made therein without departing from the scope of the invention encompassed by the appended claims.

What is claimed is:

1. An antibody or antigen-binding fragment thereof that binds mammalian Bonzo and inhibits the binding of a ligand to said Bonzo, wherein said ligand is selected from the group consisting of:
   i) a ligand having the amino acid sequence of SEQ ID NO:4;
   ii) a ligand consisting of an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
   iii) a ligand having the amino acid sequence of SEQ ID NO:6;
   iv) a ligand having the amino acid sequence of SEQ ID NO:8; and
   v) a ligand having the amino acid sequence of amino acid residues 32–101 of SEQ ID NO:8.

2. The antibody or antigen-binding fragment of claim 1, wherein said mammalian Bonzo is human Bonzo.

3. The antibody or antigen-binding fragment of claim 1, wherein said ligand is selected from the group consisting of:
   i) a ligand having the amino acid sequence of SEQ ID NO:4;
   ii) a ligand consisting of an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4; and
   iii) a ligand having the amino acid sequence of SEQ ID NO:6.

4. The antibody or antigen-binding fragment of claim 1, wherein said antibody or antigen-binding fragment:
  i) inhibits chemotaxis induced upon binding of said ligand to said Bonzo; and/or
  ii) inhibits a transient increase in the concentration of cytosolic free calcium ($[Ca^{2+}]_i$) induced upon binding of said ligand to said Bonzo.

5. The antibody or antigen-binding fragment of claim 1, wherein said antibody or antigen-binding fragment inhibits chemotaxis induced upon binding of said ligand to said Bonzo.

6. The antibody or antigen-binding fragment of claim 1, wherein said antibody or antigen-binding fragment inhibits chemotaxis induced upon binding of said ligand to said Bonzo in an in vitro chemotaxis assay with an $IC_{50}$ of less than 7 µg/mL, wherein said ligand consists of amino acid residues 30–254 of SEQ ID NO:4.

7. The antibody or antigen-binding fragment of claim 1, wherein said antibody or antigen-binding fragment inhibits chemotaxis induced upon binding of said ligand to said Bonzo in an in vitro chemotaxis assay with an $IC_{50}$ of less than 5 µg/mL, wherein said ligand consists of amino acid residues 30–254 of SEQ ID NO:4.

8. The antibody or antigen-binding fragment of claim 1, wherein said antibody or antigen-binding fragment inhibits chemotaxis induced upon binding of said ligand to said Bonzo in an in vitro chemotaxis assay with an $IC_{50}$ of less than 1 µg/mL, wherein said ligand consists of amino acid residues 30–254 of SEQ ID NO:4.

9. The antibody or antigen-binding fragment of claim 1, wherein said antibody or antigen-binding fragment inhibits a transient increase in the concentration of cytosolic free calcium ($[Ca^{2+}]_i$) induced upon binding of said ligand to said Bonzo.

10. The antibody or antigen-binding fragment of claim 1, wherein said antibody or antigen-binding fragment has the epitopic specificity of an antibody selected from the group consisting of:
  1) mAb 4A11, the antibody produced by the hybridoma cell line deposited as ATCC Accession Number PTA-991;
  2) mAb 7A2, the antibody produced by the hybridoma cell line deposited as ATCC Accession Number PTA-992; and
  3) mAb 7F3, the antibody produced by the hybridoma cell line deposited as ATCC Accession Number PTA-990.

11. The antibody or antigen-binding fragment of claim 1, wherein said antibody or antigen-binding fragment has the epitopic specificity of mAb 7F3, the antibody produced by the hybridoma cell line deposited as ATCC Accession Number PTA-990.

12. The antibody or antigen-binding fragment of claim 1, wherein said antibody or antigen-binding fragment has the epitopic specificity of mAb 4A11, the antibody produced by the hybridoma cell line deposited as ATCC Accession Number PTA-991.

13. The antibody or antigen-binding fragment of claim 1, wherein said antibody or antigen-binding fragment has the epitopic specificity of mAb 7A2, the antibody produced by the hybridoma cell line deposited as ATCC Accession Number PTA-992.

14. The antibody or antigen-binding fragment of claim 1, wherein the binding of said antibody or said antigen-binding fragment to said Bonzo is inhibited by an antibody selected from the group consisting of:
  1) mAb 4A11, the antibody produced by the hybridoma cell line deposited as ATCC Accession Number PTA-991;
  2) mAb 7A2, the antibody produced by the hybridoma cell line deposited as ATCC Accession Number PTA-992; and
  3) mAb 7F3, the antibody produced by the hybridoma cell line deposited as ATCC Accession Number PTA-990.

15. The antibody or antigen-binding fragment of claim 1, wherein the binding of said antibody or antigen-binding fragment to said Bonzo is inhibited by mAb 7F3 the antibody produced by the hybridoma cell line deposited as ATCC Accession Number PTA-990.

16. The antibody or antigen-binding fragment of claim 1, wherein the binding of said antibody or antigen-binding fragment to said Bonzo is inhibited by mAb 4A11, the antibody produced by the hybridoma cell line deposited as ATCC Accession Number PTA-991.

17. The antibody or antigen-binding fragment of claim 1, wherein the binding of said antibody or antigen-binding fragment to said Bonzo is inhibited by mAb 7A2, the antibody produced by the hybridoma cell line deposited as ATCC Accession Number PTA-992.

18. An antibody or antigen-binding fragment thereof that binds to mammalian Bonzo expressed on the membrane of a cell and inhibits a ligand-induced cellular response, wherein:
  1) said ligand-induced cellular response is selected from the group consisting of:
    a) chemotaxis; and
    b) a transient increase in the concentration of cytosolic free calcium ($[Ca^{2+}]_i$);
  and
  2) said ligand is selected from the group consisting of:
    i) a ligand having the amino acid sequence of SEQ ID NO:4;
    ii) a ligand consisting of an amino acid sequence that is a fragment of SEQ ID NO:4, wherein said fragment is selected from the group consisting of:
      a) amino acid residues 30–254 of SEQ ID NO:4;
      b) amino acid residues 1–202 of SEQ ID NO:4;
      c) amino acid residues 30–202 of SEQ ID NO:4;
      d) amino acid residues 1–155 of SEQ ID NO:4;
      e) amino acid residues 30–155 of SEQ ID NO:4;
      f) amino acid residues 1–117 of SEQ ID NO:4;
      g) amino acid residues 30–117 of SEQ ID NO:4; and
      h) amino acid residues 30–95 of SEQ ID NO:4;
    iii) a ligand having the amino acid sequence of SEQ ID NO:6;
    iv) a ligand having the amino acid sequence of SEQ ID NO:8; and
    v) a ligand having the amino acid sequence of amino acid residues 32–101 of SEQ ID NO:8.

19. The antibody or antigen-binding fragment of claim 18, wherein said mammalian Bonzo is human Bonzo.

20. The antibody or antigen-binding fragment of claim 18, wherein said ligand is selected from the group consisting of:
  i) a ligand having the amino acid sequence of SEQ ID NO:4;
  ii) a ligand consisting of an amino acid sequence that is a fragment of SEQ ID NO:4, wherein said fragment is selected from the group consisting of:
    a) amino acid residues 30–254 of SEQ ID NO:4;
    b) amino acid residues 1–202 of SEQ ID NO:4;
    c) amino acid residues 30–202 of SEQ ID NO:4;

d) amino acid residues 1–155 of SEQ ID NO:4;
e) amino acid residues 30–155 of SEQ ID NO:4;
f) amino acid residues 1–117 of SEQ ID NO:4;
g) amino acid residues 30–117 of SEQ ID NO:4; and
h) amino acid residues 30–95 of SEQ ID NO:4; and
iii) a ligand having the amino acid sequence of SEQ ID NO:6.

21. The antibody or antigen-binding fragment of claim 18, wherein said ligand-induced cellular response is chemotaxis.

22. The antibody or antigen-binding fragment of claim 18, wherein:
i) said ligand-induced cellular response is chemotaxis, and said antibody or antigen-binding fragment inhibits said chemotaxis in an in vitro chemotaxis assay with an $IC_{50}$ of less than 7 µg/mL; and
ii) said ligand consists of amino acid residues 30–254 of SEQ ID NO:4.

23. The antibody or antigen-binding fragment of claim 18, wherein:
i) said ligand-induced cellular response is chemotaxis, and said antibody or antigen-binding fragment inhibits said chemotaxis in an in vitro chemotaxis assay with an $IC_{50}$ of less than 5 µg/mL; and
ii) said ligand consists of amino acid residues 30–254 of SEQ ID NO:4.

24. The antibody or antigen-binding fragment of claim 18, wherein:
i) said ligand-induced cellular response is chemotaxis, and said antibody or antigen-binding fragment inhibits said chemotaxis in an in vitro chemotaxis assay with an $IC_{50}$ of less than 1 µg/mL; and
ii) said ligand consists of amino acid residues 30–254 of SEQ ID NO:4.

25. The antibody or antigen-binding fragment of claim 18, wherein said ligand-induced cellular response is a transient increase in the concentration of cytosolic free calcium ($[Ca^{2+}]_i$).

26. The antibody or antigen-binding fragment of claim 18, wherein said antibody or antigen-binding fragment has the epitopic specificity of an antibody selected from the group consisting of:
1) mAb 4A11, the antibody produced by the hybridoma cell line deposited as ATCC Accession Number PTA-991;
2) mAb 7A2, the antibody produced by the hybridoma cell line deposited as ATCC Accession Number PTA-992; and
3) mAb 7F3, the antibody produced by the hybridoma cell line deposited as ATCC Accession Number PTA-990.

27. The antibody or antigen-binding fragment of claim 18, wherein said antibody or antigen-binding fragment has the epitopic specificity of mAb 7F3, the antibody produced by the hybridoma cell line deposited as ATCC Accession Number PTA-990.

28. The antibody or antigen-binding fragment of claim 18, wherein said antibody or antigen-binding fragment has the epitopic specificity of mAb 4A11, the antibody produced by the hybridoma cell line deposited as ATCC Accession Number PTA-991.

29. The antibody or antigen-binding fragment of claim 18, wherein said antibody or antigen-binding fragment has the epitopic specificity of mAb 7A2, the antibody produced by the hybridoma cell line deposited as ATCC Accession Number PTA-992.

30. The antibody or antigen-binding fragment of claim 18, wherein the binding of said antibody or said antigen-binding fragment to said Bonzo is inhibited by an antibody selected from the group consisting of:
1) mAb 4A11, the antibody produced by the hybridoma cell line deposited as ATCC Accession Number PTA-991;
2) mAb 7A2, the antibody produced by the hybridoma cell line deposited as ATCC Accession Number PTA-992; and
3) mAb 7F3, the antibody produced by the hybridoma cell line deposited as ATCC Accession Number PTA-990.

31. The antibody or antigen-binding fragment of claim 18, wherein the binding of said antibody or antigen-binding fragment to said Bonzo is inhibited by mAb 7F3, the antibody produced by the hybridoma cell line deposited as ATCC Accession Number PTA-990.

32. The antibody or antigen-binding fragment of claim 18, wherein the binding of said antibody or antigen-binding fragment to said Bonzo is inhibited by mAb 4A11, the antibody produced by the hybridoma cell line deposited as ATCC Accession Number PTA-991.

33. The antibody or antigen-binding fragment of claim 18, wherein the binding of said antibody or antigen-binding fragment to said Bonzo is inhibited by mAb 7A2, the antibody produced by the hybridoma cell line deposited as ATCC Accession Number PTA-992.

34. An isolated cell that produces an antibody or antigen-binding fragment thereof that binds to mammalian Bonzo and inhibits the binding of a ligand to said Bonzo, wherein said ligand is selected from the group consisting of:
i) a ligand having the amino acid sequence of SEQ ID NO:4;
ii) a ligand consisting of an amino acid sequence that is a fragment of SEQ ID NO:4, wherein said fragment is selected from the group consisting of:
a) amino acid residues 30–254 of SEQ ID NO:4;
b) amino acid residues 1–202 of SEQ ID NO:4;
c) amino acid residues 30–202 of SEQ ID NO:4;
d) amino acid residues 1–155 of SEQ ID NO:4;
e) amino acid residues 30–155 of SEQ ID NO:4;
f) amino acid residues 1–117 of SEQ ID NO:4;
g) amino acid residues 30–117 of SEQ ID NO:4; and
h) amino acid residues 30–95 of SEQ ID NO:4;
iii) a ligand having the amino acid sequence of SEQ ID NO:6;
iv) a ligand having the amino acid sequence of SEQ ID NO:8; and
v) a ligand having the amino acid sequence of amino acid residues 32–101 of SEQ ID NO:8.

35. The isolated cell of claim 34, wherein said mammalian Bonzo is human Bonzo.

36. The isolated cell of claim 34, wherein said ligand is selected from the group consisting of:
i) a ligand having the amino acid sequence of SEQ ID NO:4;
ii) a ligand consisting of an amino acid sequence that is a fragment of SEQ ID NO:4, wherein said fragment is selected from the group consisting of:
a) amino acid residues 30–254 of SEQ ID NO:4;
b) amino acid residues 1–202 of SEQ ID NO:4;
c) amino acid residues 30–202 of SEQ ID NO:4;
d) amino acid residues 1–155 of SEQ ID NO:4;
e) amino acid residues 30–155 of SEQ ID NO:4;
f) amino acid residues 1–117 of SEQ ID NO:4;
g) amino acid residues 30–117 of SEQ ID NO:4; and
h) amino acid residues 30–95 of SEQ ID NO:4; and iii) a ligand having the amino acid sequence of SEQ ID NO:6.

37. The isolated cell of claim 34, wherein said antibody or antigen-binding fragment:
   i) inhibits chemotaxis induced upon binding of said ligand to said Bonzo; and/or
   ii) inhibits a transient increase in the concentration of cytosolic free calcium ($[Ca^{2+}]_i$) induced upon binding of said ligand to said Bonzo.

38. The isolated cell of claim 34, wherein said antibody or antigen-binding fragment inhibits chemotaxis induced upon binding of said ligand to said Bonzo.

39. The isolated cell of claim 34, wherein said antibody or antigen-binding fragment inhibits chemotaxis induced upon binding of said ligand to said Bonzo in an in vitro chemotaxis assay with an $IC_{50}$ of less than 7 µg/mL, wherein said ligand consists of amino acid residues 30–254 of SEQ ID NO:4.

40. The isolated cell of claim 34, wherein said antibody or antigen-binding fragment inhibits chemotaxis induced upon binding of said ligand to said Bonzo in an in vitro chemotaxis assay with an $IC_{50}$ of less than 5 µg/mL, wherein said ligand consists of amino acid residues 30–254 of SEQ ID NO:4.

41. The isolated cell of claim 34, wherein said antibody or antigen-binding fragment inhibits chemotaxis induced upon binding of said ligand to said Bonzo in an in vitro chemotaxis assay with an $IC_{50}$ of less than 1 µg/mL, wherein said ligand consists of amino acid residues 30–254 of SEQ ID NO:4.

42. The isolated cell of claim 34, wherein said antibody or antigen-binding fragment inhibits a transient increase in the concentration of cytosolic free calcium ($[Ca^{2+}]_i$) induced upon binding of said ligand to said Bonzo.

43. The isolated cell of claim 34, wherein said antibody or said antigen-binding fragment has the epitopic specificity of an antibody selected from the group consisting of:
   1) mAb 4A11, the antibody produced by the hybridoma cell line deposited as ATCC Accession Number PTA-991;
   2) mAb 7A2, the antibody produced by the hybridoma cell line deposited as ATCC Accession Number PTA-992; and
   3) mAb 7F3, the antibody produced by the hybridoma cell line deposited as ATCC Accession Number PTA-990.

44. The isolated cell of claim 34, wherein said antibody or antigen-binding fragment has the epitopic specificity of mAb 7F3, the antibody produced by the hybridoma cell line deposited as ATCC Accession Number PTA-990.

45. The isolated cell of claim 34, wherein said antibody or antigen-binding fragment has the epitopic specificity of mAb 4A11, the antibody produced by the hybridoma cell line deposited as ATCC Accession Number PTA-991.

46. The isolated cell of claim 34, wherein said antibody or antigen-binding fragment has the epitopic specificity of mAb 7A2, the antibody produced by the hybridoma cell line deposited as ATCC Accession Number PTA-992.

47. The isolated cell of claim 34, wherein the binding of said antibody or antigen-binding fragment to said Bonzo is inhibited by an antibody selected from the group consisting of:
   1) mAb 4A11, the antibody produced by the hybridoma cell line deposited as ATCC Accession Number PTA-991;
   2) mAb 7A2, the antibody produced by the hybridoma cell line deposited as ATCC Accession Number PTA-992; and
   3) mAb 7F3, the antibody produced by the hybridoma cell line deposited as ATCC Accession Number PTA-990.

48. The isolated cell of claim 34, wherein the binding of said antibody or antigen-binding fragment to said Bonzo is inhibited by mAb 4A11, the antibody produced by the hybridoma cell line deposited as ATCC Accession Number PTA-991.

49. The isolated cell of claim 34, wherein the binding of said antibody or antigen-binding fragment to said Bonzo is inhibited by mAb 7A2, the antibody produced by the hybridoma cell line deposited as ATCC Accession Number PTA-992.

50. The isolated cell of claim 34, wherein the binding of said antibody or antigen-binding fragment to said Bonzo is inhibited by mAb 7F3, the antibody produced by the hybridoma cell line deposited as ATCC Accession Number PTA-990.

51. The isolated cell of claim 34, wherein said isolated cell is selected from the group consisting of an immortalized B cell, a hybridoma and a recombinant cell comprising one or more exogenous nucleic acid molecules that encode said antibody or antigen-binding fragment thereof.

52. An antibody produced by murine hybridoma 4A11, deposited as ATCC Accession Number PTA-991, or an antigen-binding fragment thereof.

53. An antibody produced by murine hybridoma 7A2, deposited as ATCC Accession Number PTA-992, or an antigen-binding fragment thereof.

54. An antibody produced by murine hybridoma 7F3, deposited as ATCC Accession Number PTA-990, or an antigen-binding fragment thereof.

55. Murine hybridoma 4A11, deposited as ATCC Accession Number PTA-991.

56. Murine hybridoma 7A2, deposited as ATCC Accession Number PTA-992.

57. Murine hybridoma 7F3, deposited as ATCC Accession Number PTA-990.

58. A test kit for use in detecting the presence of a mammalian Bonzo or a portion thereof in a biological sample comprising:
   a) an antibody or antigen-binding fragment thereof that binds to mammalian Bonzo and inhibits binding of a ligand to said mammalian Bonzo, wherein said ligand is selected from the group consisting of:
      i) a ligand having the amino acid sequence of SEQ ID NO:4;
      ii) a ligand consisting of an amino acid sequence that is a fragment of SEQ ID NO:4, wherein said fragment is selected from the group consisting of:
         a) amino acid residues 30–254 of SEQ ID NO:4;
         b) amino acid residues 1–202 of SEQ ID NO:4;
         c) amino acid residues 30–202 of SEQ ID NO:4;
         d) amino acid residues 1–155 of SEQ ID NO:4;
         e) amino acid residues 30–155 of SEQ ID NO:4;
         f) amino acid residues 1–117 of SEQ ID NO:4;
         g) amino acid residues 30–117 of SEQ ID NO:4; and
         h) amino acid residues 30–95 of SEQ ID NO:4;
      iii) a ligand having the amino acid sequence of SEQ ID NO:6;

iv) a ligand having the amino acid sequence of SEQ ID NO:8; and v) a ligand having the amino acid sequence of amino acid residues 32–101 of SEQ ID NO:8; and b) one or more ancillary reagents suitable for detecting the presence of a complex between said antibody or antigen-binding fragment and said mammalian Bonzo.

59. The test kit of claim 58 wherein said antibody or antigen-binding fragment is selected from the group consisting of:

a) mAb 4A11, the antibody produced by the hybridoma cell line deposited as ATCC Accession Number PTA-991;

b) mAb 7A2, the antibody produced by the hybridoma cell line deposited as ATCC Accession Number PTA-992;

c) mAb 7F3, the antibody produced by the hybridoma cell line deposited as ATCC Accession Number PTA-990;

d) an antibody that competes with mAb 4A11, mAb 7A2 or mAb 7F3 for binding to mammalian Bonzo; and e) an antigen-binding fragment of a), b), c) or d).

60. A method of detecting a mammalian Bonzo or portion thereof in a biological sample, comprising:

a) contacting a biological sample with an antibody or antigen-binding fragment thereof that binds to mammalian Bonzo and inhibits the binding of a ligand thereto, under conditions appropriate for binding of said antibody or antigen-binding fragment to said Bonzo or a portion thereof; and b) detecting binding of said antibody or antigen-binding fragment to said Bonzo or portion thereof;

wherein said ligand is selected from the group consisting of:

i) a ligand having the amino acid sequence of SEQ ID NO:4;

ii) a ligand consisting of an amino acid sequence that is a fragment of SEQ ID NO:4, wherein said fragment is selected from the group consisting of:
a) amino acid residues 30–254 of SEQ ID NO:4;
b) amino acid residues 1–202 of SEQ ID NO:4;
c) amino acid residues 30–202 of SEQ ID NO:4;
d) amino acid residues 1–155 of SEQ ID NO:4;
e) amino acid residues 30–155 of SEQ ID NO:4;
f) amino acid residues 1–117 of SEQ ID NO:4;
g) amino acid residues 30–117 of SEQ ID NO:4; and
h) amino acid residues 30–95 of SEQ ID NO:4;

iii) a ligand having the amino acid sequence of SEQ ID NO:6;

iv) a ligand having the amino acid sequence of SEQ ID NO:8; and v) a ligand having the amino acid sequence of amino acid residues 32–101 of SEQ ID NO:8, and wherein the binding of said antibody or antigen-binding fragment to said Bonzo or portion thereof indicates the presence of said Bonzo or portion thereof.

* * * * *

SEQUENCE LISTING

```
<160> NUMBER OF SEQ ID NOS: 18

<210> SEQ ID NO 1
<211> LENGTH: 1029
<212> TYPE: DNA
<213> ORGANISM: Homo sapiens

<400> SEQUENCE: 1
atggcagagc atgattacca tgaagactat gggttcagca gtttcaatga cagcagccag      60
gaggagcatc aagacttcct gcagttcagc aaggtctttc tgccctgcat gtacctggtg     120
gtgtttgtct gtggtctggt ggggaactct ctggtgctgg tcatatccat cttctaccat     180
aagttgcaga gcctgacgga tgtgttcctg gtgaacctac ccctggctga cctggtgttt     240
gtctgcactc tgcccttctg ggcctatgca ggcatccatg aatgggtgtt tggccaggtc     300
atgtgcaaga gcctactggg catctacact attaacttct acacgtccat gctcatcctc     360
acctgcatca ctgtggatcg tttcattgta gtggttaagg ccaccaaggc ctacaaccag     420
caagccaaga ggatgacctg gggcaaggtc accagcttgc tcatctgggt gatatccctg     480
ctggtttcct tgccccaaat tatctatggc aatgtcttta atctcgacaa gctcatatgt     540
ggttaccatg acgaggcaat ttccactgtg gttcttgcca cccagatgac actggggttc     600
ttcttgccac tgctcaccat gattgtctgc tattcagtca taatcaaaac actgcttcat     660
gctggaggct ccagaagca cagatctcta aagatcatct tcctggtgat ggctgtgttc     720
ctgctgaccc agatgccctt caacctcatg aagttcatcc gcagcacaca ctgggaatac     780
tatgccatga ccagctttca ctacaccatc atggtgacag aggccatcgc atacctgagg     840
gcctgcctta accctgtgct ctatgccttt gtcagcctga gtttcgaaa gaacttctgg     900 aaacttgtga aggacattgg ttgcctccct taccttgggg tctcacatca atggaaatct     960
```

```
tctgaggaca attccaagac tttttctgcc tcccacaatg tggaggccac cagcatgttc    1020
cagttatag                                                             1029
```

<210> SEQ ID NO 2
<211> LENGTH: 342
<212> TYPE: PRT
<213> ORGANISM: Homo sapiens

<400> SEQUENCE: 2

```
Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340
```

<210> SEQ ID NO 3
<211> LENGTH: 1763
<212> TYPE: DNA
<213> ORGANISM: Homo sapiens

<400> SEQUENCE: 3

```
ggcacgaggc cgagatggga cgggacttgc ggcccgggtc ccgcgtgctc ctgctcctgc      60
ttctgctcct gctggtgtac ctgactcagc caggcaatgg caacgagggc agcgtcactg     120
gaagttgtta ttgtggtaaa agaatttctt ccgactcccc gccatcggtt cagttcatga     180
atcgtctccg gaaacacctg agagcttacc atcggtgtct atactacacg aggttccagc     240
tcctttcctg gagcgtgtgt ggaggcaaca aggacccatg ggttcaggaa ttgatgagct     300
gtcttgatct caaagaatgt ggacatgctt actcggggat tgtggcccac cagaagcatt     360
tacttcctac cagcccccca atttctcagg cctcagaggg ggcatcttca gatatccaca     420
ccctgcccca gatgctcctg tccaccttgc agtccactca gcgccccacc ctcccagtag     480
gatcactgtc ctcggacaaa gagctcactc gtcccaatga accaccatt cacactgcgg      540
gccacagtct ggcagttggg cctgaggctg ggagaaccca aagcagccg aaaaaaatg       600
ctggtcccac agccaggaca tcagccacag tgccggtcct gtgcctcctg ccatcatct      660
tcatcctcac cgcagcccct tcctatgtgc tgtgcaagag gaggaggggg cagtcaccgc     720
agtcctctcc agatctgccg gttcattata tacctgtggc acctgactct aatacctgag     780
ccaagaatgg aagcttgtga ggagacggac tctatgttgc ccaggctgtt atggaactcc     840
tgagtcaagt gatcctccca ccttggcctc tgaaggtgcg aggattatag gcgtcaccta     900
ccacatccag cctacacgta tttgttaata tctaacatag gactaaccag ccactgccct     960
ctcttaggcc cctcatttaa aaacggttat actataaaat ctgcttttca cactgggtga    1020
taataacttg gacaaattct atgtgtattt tgttttgttt tgctttgctt tgttttgaga    1080
cggagtctcg ctctgtcatc caggctggag tgcagtggca tgatctcggc tcactgcaac    1140
ccccatctcc caggttcaag cgattctcct gcctcctcct gagtagctgg gactacaggt    1200
gctcaccacc acacccggct aatttttgt attttagta gagaccgggg tttcaccatg      1260
ttgaccaggc tggtctcgaa ctcctgacct ggtgatctgc ccacccaggc ctcccaaagt    1320
gctgggatta aggtgtgag ccaccatgcc tggccctatg tgtgtttttt aactactaaa     1380
aattattttt gtaatgattg agtcttcttt atggaaacaa ctggcctcag cccttgcgcc    1440
cttactgtga ttcctggctt catttttgc tgatggttcc ccctcgtccc aaatctctct     1500
cccagtacac cagttgttcc tcccccacct cagccctctc ctgcatcctc ctgtacccgc    1560
aacgaaggcc tgggctttcc caccctccct ccttagcagg tgccgtgctg ggacaccata    1620
cgggttggtt tcacctcctc agtcccttgc ctaccccagt gagagtctga tcttgttttt    1680
attgttattg cttttattat tattgctttt attatcatta aaactctagt tcttgttttg    1740
tctctccgaa aaaaaaaaa aaa                                             1763
```

<210> SEQ ID NO 4
<211> LENGTH: 254
<212> TYPE: PRT
<213> ORGANISM: Homo sapiens

<400> SEQUENCE: 4

```
Met Gly Arg Asp Leu Arg Pro Gly Ser Arg Val Leu Leu Leu Leu Leu
 1               5                  10                  15
```

```
Leu Leu Leu Leu Val Tyr Leu Thr Gln Pro Gly Asn Gly Asn Glu Gly
            20                  25                  30

Ser Val Thr Gly Ser Cys Tyr Cys Gly Lys Arg Ile Ser Ser Asp Ser
        35                  40                  45

Pro Pro Ser Val Gln Phe Met Asn Arg Leu Arg Lys His Leu Arg Ala
    50                  55                  60

Tyr His Arg Cys Leu Tyr Tyr Thr Arg Phe Gln Leu Leu Ser Trp Ser
65                  70                  75                  80

Val Cys Gly Gly Asn Lys Asp Pro Trp Val Gln Glu Leu Met Ser Cys
                85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Ile Ser Gln Ala Ser Glu
        115                 120                 125

Gly Ala Ser Ser Asp Ile His Thr Pro Ala Gln Met Leu Leu Ser Thr
    130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Val Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Pro Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250

<210> SEQ ID NO 5
<211> LENGTH: 2309
<212> TYPE: DNA
<213> ORGANISM: Homo sapiens

<400> SEQUENCE: 5
cggcgactct ctccaccggg ccgcccggga ggctcatgca gcgcggctgg gtcccgcggc      60
gcccggatcg gggaagtgaa agtgcctcgg aggaggaggg ccggtccggc agtgcagccg     120
cctcacaggt cggcggacgg gccaggcggg cggcctcctg aaccgaaccg aatcggctcc     180
tcgggccgtc gtcctcccgc ccctcctcgc ccgccgccgg agttttcttt cggtttcttc     240
caagattcct ggccttccct cgacggagcc gggcccagtg cggggcgcgca gggcgcggga     300 gctccacctc ctcggctttc cctgcgtcca gaggctggca tggcgcgggc cgagtactga     360
gcgcacggtc ggggcacagc agggccggtg ggtgcagctg gctcgcgcct cctctccggc     420
cgccgtctcc tccggtcccc ggcgaaagcc attgagacac cagctggacg tcacgcgccg     480
gagcatgtct gggagtcaga gcgaggtggc tccatccccg cagagtccgc ggagccccga     540
gatgggacgg gacttgcggc ccgggtcccg cgtgctcctg ctcctgcttc tgctcctgct     600
ggtgtacctg actcagccag gcaatggcaa cgagggcagc gtcactggaa gttgttattg     660
tggtaaaaga atttcttccg actccccgcc atcggttcag ttcatgaatc gtctccggaa     720
acacctgaga gcttaccatc ggtgtctata ctacacgagg ttccagctcc tttcctggag     780
```

-continued

```
cgtgtgtgga ggcaacaagg acccatgggt tcaggaattg atgagctgtc ttgatctcaa    840
agaatgtgga catgcttact cggggattgt ggcccaccag aagcatttac ttcctaccag    900 cccccaact tctcaggcct cagaggggggc atcttcagat atccacaccc ctgcccagat    960
gctcctgtcc accttgcagt ccactcagcg ccccaccctc ccagtaggat cactgtcctc   1020
ggacaaagag ctcactcgtc ccaatgaaac caccattcac actgcgggcc acagtctggc   1080
agttgggcct gaggctgggg agaaccagaa gcagccggaa aaaaatgctg gtcccacagc   1140
caggacatca gccacagtgc cggtcctgtg cctcctggcc atcatcttca tcctcaccgc   1200 agcccttttcc tatgtgctgt gcaagaggag gaggggggcag tcaccgcagt cctctccaga   1260
tctgccggtt cattatatac ctgtggcacc tgactctaat acctgagcca agaatggaag   1320
cttgtgagga gacggactct atgttgccca ggctgttatg gaactcctga gtcaagtgat   1380
cctcccacct tggcctctga aggtgcgagg attataggcg tcacctacca catccagcct   1440
acacgtattt gttaatatct aacataggac taaccagcca ctgccctctc ttaggccct   1500 catttaaaaa cggttatact ataaaatctg cttttcacac tgggtgataa aacttggac   1560 aaattctatg tgtattttgt tttgttttgc tttgctttgt tttgagacgg agtctcgctc   1620
tgtcatccag gctggagtgc agtggcatga tctcggctca ctgcaaccc catctcccag   1680 gttcaagcga ttctcctgcc tcctcctaag tagctgggac tacaggtgct caccaccaca   1740
cccggctaat ttttgtatt tttagtagag acggggtttc accatgttga ccaggctggt   1800
ctcgaactcc tgacctggtg atctgcccac ccaggcctcc caaagtgctg ggattaaagg   1860
tgtgagccac catgcctggc cctatgtgtg ttttttaact actaaaaatt attttttgtaa   1920 tgattgagtc ttctttatgg aaacaactgg cctcagccct tgcgcccta ctgtgattcc   1980 tggcttcatt ttttgctgat ggttcccct cgtcccaaat ctctctccca gtacaccagt   2040
tgttcctccc ccacctcagc cctctcctgc atcctcctgt acccgcaacg aaggcctggg   2100
ctttcccacc ctccctcctt agcaggtgcc gtgctgggac accatacggg ttggtttcac   2160
ctcctcagtc ccttgcctac cccagtgaga gtctgatctt gttttttattg ttattgcttt   2220 tattattatt gcttttatta tcattaaaac tctagttctt gttttgtctc tcaaaaaaaa   2280
aaaaaaaaaa aaaaaaaaaa aaaaaaaaa                                    2309
```

<210> SEQ ID NO 6
<211> LENGTH: 254
<212> TYPE: PRT
<213> ORGANISM: Homo sapiens

<400> SEQUENCE: 6

```
Met Gly Arg Asp Leu Arg Pro Gly Ser Arg Val Leu Leu Leu Leu Leu
 1               5                  10                  15

Leu Leu Leu Leu Val Tyr Leu Thr Gln Pro Gly Asn Gly Asn Glu Gly
            20                  25                  30

Ser Val Thr Gly Ser Cys Tyr Cys Gly Lys Arg Ile Ser Ser Asp Ser
        35                  40                  45

Pro Pro Ser Val Gln Phe Met Asn Arg Leu Arg Lys His Leu Arg Ala
    50                  55                  60

Tyr His Arg Cys Leu Tyr Tyr Thr Arg Phe Gln Leu Leu Ser Trp Ser
65                  70                  75                  80

Val Cys Gly Gly Asn Lys Asp Pro Trp Val Gln Glu Leu Met Ser Cys
                85                  90                  95

Leu Asp Leu Lys Glu Cys Gly His Ala Tyr Ser Gly Ile Val Ala His
```

```
                  100                 105                 110
Gln Lys His Leu Leu Pro Thr Ser Pro Pro Thr Ser Gln Ala Ser Glu
            115                 120                 125

Gly Ala Ser Ser Asp Ile His Thr Pro Ala Gln Met Leu Leu Ser Thr
        130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Val Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250
```

<210> SEQ ID NO 7
<211> LENGTH: 439
<212> TYPE: DNA
<213> ORGANISM: Homo sapiens

<400> SEQUENCE: 7

```
ccgcagcatg agctccgcag ccgggttctg cgcctcacgc cccgggctgc tgttcctggg      60
gttgctgctc ctgccacttg tggtcgcctt cgccagcgct gaagctgaag aagatgggga     120
cctgcagtgc ctgtgtgtga agaccacctc ccaggtccgt cccaggcaca tcaccagcct     180
ggaggtgatc aaggccggac cccactgccc cactgcccaa ctgatagcca cgctgaagaa     240
tggaaggaaa atttgcttgg acctgcaagc cccgctgtac aagaaaataa ttaagaaact     300
tttggagagt tagctactag ctgcctacgt gtgtgcattt gctatatagc atacttcttt     360
tttccagttt caatctaact gtgaaagaaa cttctgatat ttgtgttatc cttatgattt     420
taaataaaca aaataaatc                                                  439
```

<210> SEQ ID NO 8
<211> LENGTH: 101
<212> TYPE: PRT
<213> ORGANISM: Homo sapiens

<400> SEQUENCE: 8

```
Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95
```

```
Lys Leu Leu Glu Ser
            100

<210> SEQ ID NO 9
<211> LENGTH: 69
<212> TYPE: DNA
<213> ORGANISM: Artificial Sequence
<220> FEATURE:
<223> OTHER INFORMATION: Synthetic Oligonucleotide

<400> SEQUENCE: 9
tttggatcca tgtatcccta tgacgtgccc gactatgctg cagagcatga ttaccatgaa      60
gactatggg                                                              69

<210> SEQ ID NO 10
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 10
tttgcggccg cctataactg gaacatgctg gtggcctc                              38

<210> SEQ ID NO 11
<211> LENGTH: 12
<212> TYPE: PRT
<213> ORGANISM: Unknown
<220> FEATURE:
<223> OTHER INFORMATION: Hemagglutinin epitope

<400> SEQUENCE: 11

Cys Tyr Pro Tyr Asp Val Pro Asp Tyr Ala Ser Leu
 1               5                  10

<210> SEQ ID NO 12
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 12
cgcgtcgaca gccgagatgg gacgggactt g                                     31

<210> SEQ ID NO 13
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 13
ggtctagatg tcctggctgt gggacca                                          27

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 14
gaggatccat gggacgggac ttg                                              23
```

```
<210> SEQ ID NO 15
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 15
cctctagatg atgtcctggc tgtgggac                                      28

<210> SEQ ID NO 16
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 16
ggtctagaaa gtaaatgctt ctggtgggc                                     29

<210> SEQ ID NO 17
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 17
cctctagagc tcatcaattc ctgaaccc                                      28

<210> SEQ ID NO 18
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 18
ggtctagact gggagggtgg ggcgctgag                                     29
```